(12) United States Patent
Kool

(10) Patent No.: US 6,218,108 B1
(45) Date of Patent: Apr. 17, 2001

(54) NUCLEOSIDE ANALOGS WITH POLYCYCLIC AROMATIC GROUPS ATTACHED, METHODS OF SYNTHESIS AND USES THEREFOR

(75) Inventor: Eric T. Kool, Rochester, NY (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 08/857,721

(22) Filed: May 16, 1997

(51) Int. Cl.$^7$ ....................................................... C12Q 1/68
(52) U.S. Cl. ............................... 435/6; 536/1.11; 536/4.1; 536/17.2; 536/17.3; 536/17.4; 536/18.5; 536/18.6; 536/23.1; 536/25.3; 536/25.32; 536/25.34; 536/29.2
(58) Field of Search .................... 536/1.11, 4.1, 536/17.2, 17.3, 17.4, 29.2, 25.34, 18.5, 18.6, 23.1, 25.3, 25.32; 435/6

(56) References Cited

U.S. PATENT DOCUMENTS

| | | | |
|---|---|---|---|
| 4,656,260 | * | 4/1987 | Kato et al. ........................... 536/29.2 |
| 5,137,876 | * | 8/1992 | MacCoss et al. .................... 536/29.2 |

FOREIGN PATENT DOCUMENTS

| | | | |
|---|---|---|---|
| 4525101 | * | 6/1965 | (JP) ..................................... 536/29.2 |
| 1294674 | * | 4/1988 | (JP) ..................................... 536/29.2 |
| WO 95/05391 | * | 2/1995 | (WO) . |

OTHER PUBLICATIONS

Kool, et al. "Naphthalene, Phenanthrene, and Pyrene as DNA Base Analogues: Synthesis, Structure, and Fluorescene in DNA", J. Am Chem. Soc.: vol. 118: 7671–7678 (1996).*

Kool, et al. "Experimental Measurement of Aromatic Stacking Affinities in the Context of Duplex DNA", J.Am. Chem. Soc.: vol. 118: 8182–8183 (1996).*

Newton, et al. "The Production of PCR Products With 5' Single–Stranded Tails Using Primers That Incorporate Novel Phosphoramidite Intermediates", Nucleic Acids Research, vol. 21: 1155–1162 (1993).*

Letsinger, et al. "Synthesis and Properties of Oligonucleotides Bearing a Pendant Pyrene Group", Necleic Acids Research, vol. 16:169–172 (1985).*

Bischofberger, et al., "Synthesis of Novel Polycyclic Nucleoside Analogues, Incorporated into Oligodeoxynucleotides, and Interaction with Complementary Sequences", J. Am. Chem. Soc., vol. 111:3041–3046 (1989).*

Ren et al., J. Am. Chem. Soc., vol. 118, No. 33, p. 7671–7678.*

* cited by examiner

*Primary Examiner*—James O. Wilson
(74) *Attorney, Agent, or Firm*—Scully, Scott, Murphy & Presser

(57) ABSTRACT

The present invention provides fluorescent nucleosides carrying polycyclic aromatic hydrocarbons such as anthracene, phenanthrene, pyrene stilbene, tetracene or pentacene. The subject nucleosides may be synthesized using a C-glycosidic bond formation method employing organocadmium or organozinc derivatives of the aromatic compounds and coupling with a 1-α-chlororibose or deoxyribose synthon. The α-anomers of the coupling reaction may be epimerized to the β-anomers by acid-catalyzed equilibration. The fluorescent nucleosides act as DNA or RNA base analogs and can be incorporated into nucleic acids. Resultant fluorescently tagged nucleic acids are useful as probes for target nucleic acids in tissues, solutions or immobilized on membranes.

20 Claims, 25 Drawing Sheets

(1 of 25 Drawing Sheet(s) Filed in Color)

α-anomer

Irradiation at:

Hα: 0 enhancements
Hβ: 2 enhancements

β-anomer

Irradiation at:

Hα: 1 enhancement
Hβ: 1 enhancement

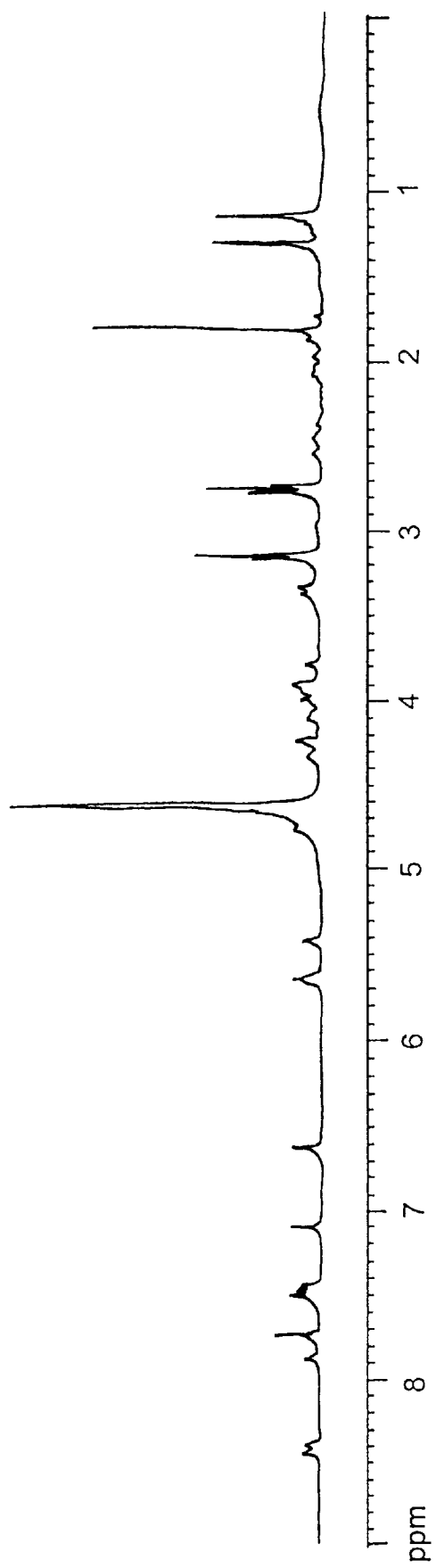

(1a: α-anomer)

(2a: α-anomer)

(3a: α-anomer)

(4a: α-anomer)

(5a: α-anomer)

(6a: α-anomer)

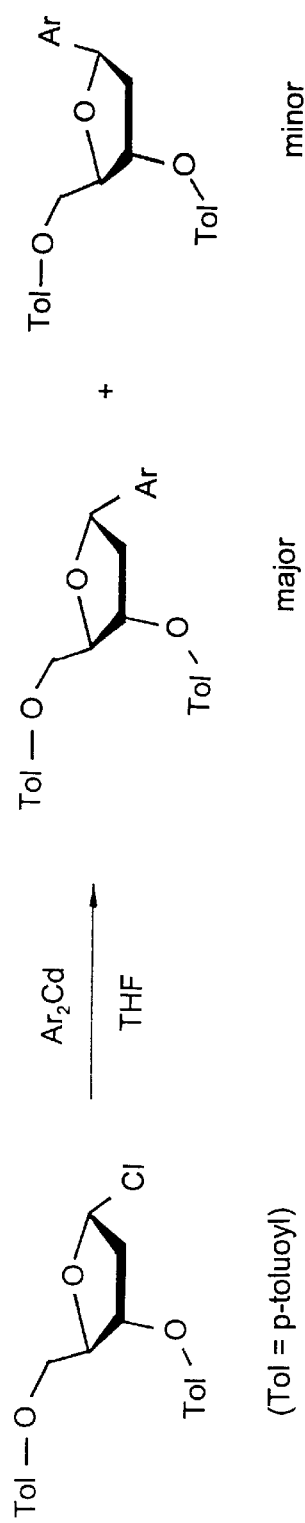
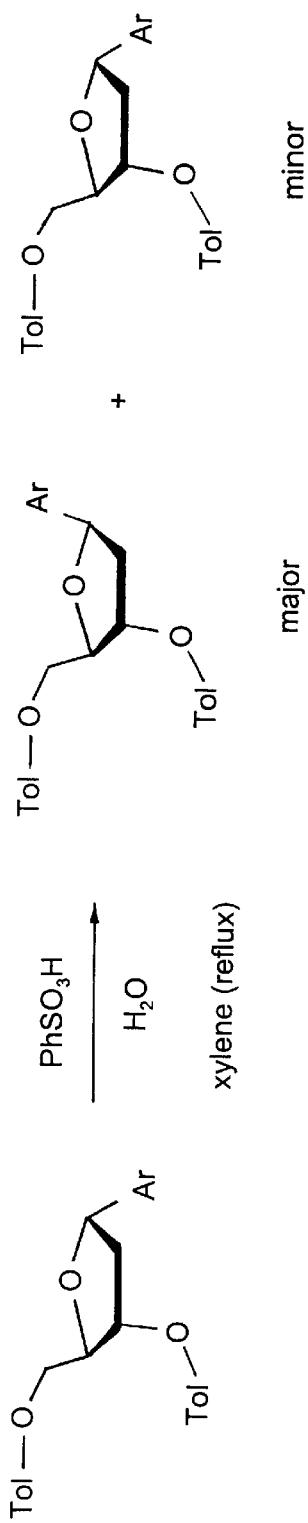
Figure 6

Emission spectra of oligonucleotides containig 1, 2, 3, and 5 fluoresceins (from commercially available phosphoramidite). Note strong quenching that occurs with multiple labels.

(P = α-PYRENE NUCLEOTIDE)

```
        T                                        P
       T CTTTTCTTCT  -3'                        T CTTTTCTTCT  -3'
P0     T    GAAAAGAAGA  -3'      P3A     P      GAAAAGAAGA  -3'
       T T CTTTTCTTCT  -5'              T P CTTTTCTTCT  -5'

T                                        P
       T CTTTTCTTCT  -3'                        P CTTTTCTTCT  -3'
P1     P    GAAAAGAAGA  -3'      P3A     P      GAAAAGAAGA  -3'
       T T CTTTTCTTCT  -5'              P P CTTTTCTTCT  -5'

T                                        T
       P CTTTTCTTCT  -3'                        T CTTTTCTTCT  -3'
P3     P    GAAAAGAAGA  -3'      P3END   T      GAAAAGAAGA  -3'
       P T CTTTTCTTCT  -5'              T T CTTTTCTTCTPPP-5'
```

Structures of complexes of triplex-forming oligonucleotides with the complementary target sequence 5'-dGAAAAGAAGA.

Figure 13

Emission intensities with multiple pyrenes

| α-pyrene sequences | relative intensity |
|---|---|
| pyrene nucleoside alone | 1.0 |

P1
$$\text{T}^{\text{T}}\text{CTTTTCTTCT -3'}$$
P
$$\text{T}_{\text{T}}\text{CTTTTCTTCT -5'}$$
10

P2
$$\text{T}^{\text{T}}\text{CTTTTCTTCT -3'}$$
P
$$\text{P}_{\text{T}}\text{CTTTTCTTCT -5'}$$
11

P3
$$\text{P}^{\text{T}}\text{CTTTTCTTCT -3'}$$
P
$$\text{P}_{\text{T}}\text{CTTTTCTTCT -5'}$$
18

P5
$$\text{P}^{\text{P}}\text{CTTTTCTTCT -3'}$$
P
$$\text{P}_{\text{P}}\text{CTTTTCTTCT -5'}$$
89

C6
$$_\text{P}\text{TCTTTTCTTCTTCTTTTCT}_\text{P}$$
$$^\text{P}_\text{P}\qquad\qquad\qquad\qquad\quad{}^\text{P}$$
$$\text{TCTTTTCTTCTTCTTTTCT}^\text{P}$$
37

C10
$$_\text{P}\text{PCTTTTCTTCTTCTTTTCP}_\text{P}$$
$$^\text{P}_\text{P}\qquad\qquad\qquad\qquad\quad{}^\text{P}$$
$$\text{PCTTTTCTTCTTCTTTTCP}^\text{P}$$
196

SEQUENCE LISTING

```
<160> NUMBER OF SEQ ID NOS: 17

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:
      synthetically generated DNA oligonucleotide

<400> SEQUENCE: 1
gaaagaaga                                                          10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: random
      synthetically generated oligonucleotides designed
      to bind human telomere repeats
<220> FEATURE:
<221> NAME/KEY: modified_base
<222> LOCATION: (18)
```

```
<223> OTHER INFORMATION: The nucleic acid residue at location 18 is
      modified with 3 adjacent pyrene molecules

<400> SEQUENCE: 2
ccctaaccct aaccctaa                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (1)
<223> OTHER INFORMATION: The nucleic acid residue at location 1 is
      modified with 3 adjacent pyrene molecules

<400> SEQUENCE: 3
ccctaaccct aaccctaa                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (1)
<223> OTHER INFORMATION: The nucleic acid residue at location 1 is
      modified with 3 adjacent pyrene molecules

<400> SEQUENCE: 4
aaccctaacc ctaaccct                                                 18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (17)..(18)
<223> OTHER INFORMATION: The nucleic acid residues at locations 17 and
      18 are modified with 3 adjacent pyrene molecules

<400> SEQUENCE: 5
ccctaaccct aaccctaaa                                                19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (18)
<223> OTHER INFORMATION: The nucleic acid residue at location 18 is
      modified with 6 adjacent pyrene molecules

<400> SEQUENCE: 6
ccctaaccct aaccctaa                                                 18
```

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      synthetically
      generated DNA oligonucleotide
<220> FEATURE:
<221> NAME/KEY: modified_base
<222> LOCATION: (18)
<223> OTHER INFORMATION: The nucleic acid residue at location 18 is
      modified with 1 pyrene molecule

<400> SEQUENCE: 7
ccctaacccT aaccctaa                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (18)
<223> OTHER INFORMATION: The nucleic acid residue at location 18 is
      modified with  1 pyrene molecule

<400> SEQUENCE: 8
ccctaacccT aaccctaa                                                18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (18)
<223> OTHER INFORMATION: The nucleic acid residue at location 18 is
      modified with 2 adjacent pyrene molecules

<400> SEQUENCE: 9
ccctaacccT aaccctaa                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (18)
<223> OTHER INFORMATION: The nucleic acid residue at location 18 is
      modified with 4 adjacent pyrene molecules

<400> SEQUENCE: 10
ccctaacccT aaccctaa                                                18

<210> SEQ ID NO 11
<211> LENGTH: 18
<212> TYPE: DNA
<213> ORGANISM: Artificial Sequence
<220> FEATURE:
```

```
<223> OTHER INFORMATION: Description of Artificial Sequence:
      synthetically generated DNA oligonucleotide
<220> FEATURE:
<221> NAME/KEY: modified_base
<222> LOCATION: (18)
<223> OTHER INFORMATION: The nucleic acid residue at location 18 is
      modified with 5 adjacent pyrene molecules

<400> SEQUENCE: 11
ccctaaccct aaccctaa                                                         18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (1)
<223> OTHER INFORMATION: The nucleic acid residue at location 1 is
       modified with 4 adjacent pyrene molecules
<220> FEATURE:
<221> NAME/KEY: modified_base
<222> LOCATION: (17)
<223> OTHER INFORMATION: The nucleic acid residue at location 17 is
      modified with 7 adjacent pyrene molecules

<400> SEQUENCE: 12 cctaaccta accctaa                                                           17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (1)
<223> OTHER INFORMATION: The nucleic acid residue at location 1 is
      modified with 4 adjacent pyrene molecules

<400> SEQUENCE: 13 accctaacc ctaacct                                                           17

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide
<220> FEATURE:
<221> NAME/KEY: modified_base
<222> LOCATION: (1)
<223> OTHER INFORMATION: The nucleic acid residue at location 1 is
      modified with 5 adjacent pyrene molecules

<400> SEQUENCE: 14
aaccctaacc ctaaccct                                                         18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:
        synthetically generated DNA oligonucleotide
```

```
<220> FEATURE:
<221> NAME/KEY: modified_base
<222> LOCATION: (1)
<223> OTHER INFORMATION: The nucleic acid residue at location 1 is
      modified with 6 adjacent pyrene molecules

<400> SEQUENCE: 15
aaccctaacc ctaaccct                                                 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide

<400> SEQUENCE: 16
ttagggttag ggttaggg                                                 18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:
      synthetically generated DNA oligonucleotide

<400> SEQUENCE: 17
agggttaggg ttagggtt                                                 18
```

NUCLEOSIDE ANALOGS WITH POLYCYCLIC AROMATIC GROUPS ATTACHED, METHODS OF SYNTHESIS AND USES THEREFOR

This invention was made with United States government support under grant number DAAH-04-93-G-0431 awarded by the Army Research Office. The United States government may have certain rights in the invention.

FIELD OF THE INVENTION

The present invention provides fluorescent nucleosides carrying polycyclic aromatic hydrocarbons such as anthracene, phenanthrene, pyrene, stilbene, tetracene or pentacene. The subject nucleosides may be synthesized using a C-glycosidic bond formation method employing organocadmium or organozinc derivatives of the aromatic compounds and coupling with a 1-α-chlororibose or deoxyribose synthon. The α-anomers of the coupling reaction may be epimerized to the β-anomers by acid-catalyzed equilibration. The fluorescent nucleosides act as DNA or RNA base analogs and can be incorporated into nucleic acids. Resultant fluorescently tagged nucleic acids are useful as probes for target nucleic acids in tissues, solutions or immobilized on membranes.

BACKGROUND OF THE INVENTION

A large number of non-natural analogues of DNA nucleosides have been synthesized in recent years. Changing the structure of the base moiety attached to deoxyribose has been a useful strategy for probing structure and function in DNA. For example, a number of base analogues have been used to test the importance of specific hydrogen bonding interactions which may be important for function of the natural nucleic acid bases.[1–3] Using this strategy, the importance of hydrogen bonding in stabilizing DNA and RNA structure, in protein interactions and in the fidelity of enzymatic DNA and RNA synthesis has been examined.

Modified DNA bases have also been synthesized with the purpose of serving as reporter groups in physical and biochemical studies of structure and function. Examples of reporter groups which have been attached to DNA bases include biotin[4] and digoxigenin groups[5], spin-label groups[6], and DNA-cleaving moieties[7]. Among the most prominent classes of reporters used in DNA are fluorescent-tagged DNA bases which can serve as probes in biophysical and biochemical studies[8]. In contrast to placement of such reporter groups at the end of a DNA strand using nonnucleotide linkers, the attachment of a reporter to a DNA base allows for placement and probing within a stretch of DNA. Such a strategy has found considerable practical use in fluorescence-based automated DNA sequencing.[9] An alternative approach to the conjugation of a fluorophore to a natural DNA base is the more direct modification of a DNA base itself to render it fluorescent. A number of modified DNA bases with useful fluorescence properties have been reported recently; among the most widely used nucleosides of this type are 2-aminopurine[10] and ethenoadenosine[11].

DNA may be fluorescently tagged either enzymatically or synthetically. Enzymatic incorporation is carried out by use of nucleoside triphosphates carrying a given fluorophore. Incorporation into DNA by chemical methods is especially common. Chemical methods of incorporating fluorescent reagents into DNA is done by either of two methods: direct incorporation of a label which has been converted to a phosphoramidite derivative or incorporation of an amine into the oligonucleotide, followed by later derivatization with a fluorophore isothiocynate or NHS ester derivative.

The postsynthesis derivatizaton of DNA is typically inefficient, and requires steps beyond those of standard DNA synthesis as well as laborious purification steps. Direct incorporation of a label into DNA is attractive because standard DNA synthesis and purification steps are used. However, currently available reagents are quite expensive due to their cost of synthesis.

Another drawback to currently used fluorescent-tagged nucleic acids is the quenching phenomenon which occurs when multiple fluorescent tags are placed near each other. Thus, a nucleic acid with multiple fluorescent tags is often no brighter or even less bright than a nucleic acid with a single fluorescent tag.

In addition, it is commonly observed that a fluorescent tag is quenched by the act of attaching it to DNA. For example, it has been reported (Netzel, 1989 J. Am. Chem. Soc. 111:6966) that pyrene tags attached to a linker at the end of a DNA strand were quenched greatly (50-fold) in the DNA. Moreover, on binding a complementary sequence, the emission was quenched another ten-fold. This effect necessarily leads to lower sensitivity of detection.

Another limitation of commercially available fluorescent labels include their rapid photobleaching characteristics. As in fluorescence microscopy or blot hybridization, the practical brightness of a label depends on the time of integration of the emission signal. Fluorescein, for example, photobleaches quite rapidly in a DNA oligonucleotide, because of its complex structure (allowing greater reactivity) and because it is exposed to solution where more reactions occur. In addition, a label such as fluorescein is typically attached to DNA by flexible tethers. Measuring protein-DNA binding by time-resolved fluorescence an isotropy is often problematic since the fluorophore tumbles rapidly on its flexible chain.

The present invention overcomes many of the shortcomings associated with labeling nucleic acids. The present invention allows a pyrene, anthracene, phenanthrene, stilbene, tetracene or pentacene-derivatized nucleoside to be inserted within a DNA or RNA strand at any position and remain rigidly stacked within the helix. Because the fluorescent part of the label is situated as if it were a DNA base, the fluorescent groups are stacked neatly in the helix, and if placed adjacent to each other, interact with each other strongly, allowing for intense excimer emission.

The fluorescent nucleoside analogs of the present invention do not photobleach rapidly, making the labeled sample much longer lived and allowing the opportunity for measurements and study over a longer period. Moreover, since the preferred embodiment of the invention provides for α-linkages to the fluorescent moiety, quenching by adjacent β-linked DNA bases is minimized. In addition, the direct attachment of the fluorescent moiety to the sugar residue in the nucleotide chain eliminates the flexible linker typically present in fluorescently labeled nucleic acids. This feature simplifies measurements such as time-resolved fluorescence anisotropy.

SUMMARY OF THE INVENTION

The present invention provides fluorescent nucleoside analogs carrying a polycyclic aromatic hydrocarbon such as anthracene, phenanthrene, pyrene, stilbene, tetracene or pentacene. The polycyclic aromatic hydrocarbon is attached to the C1 (1') position of a sugar moiety such as ribose or deoxyribose by a carbon-carbon bond. The sugar moiety may be a hexose such as glucose or a pentose such as arabinose. In one embodiment of the invention, the aromatic hydrocarbon attached to the C1 carbon of a sugar moiety is phenanthrene. In another embodiment of the invention, the aromatic hydrocarbon attached to the C1 carbon of a sugar moiety is pyrene. In still another embodiment of the invention, the aromatic hydrocarbon attached to the C1 carbon of a sugar moiety is anthracene. In another embodiment of the invention, the aromatic hydrocarbon attached to the C1 carbon of a sugar moiety is stilbene. In another embodiment of the invention, the aromatic hydrocarbon attached to the C1 carbon of a sugar moiety is tetracene. In another embodiment of the invention, the aromatic hydrocarbon attached to the C1 carbon of a sugar moiety is pentacene.

The present invention also provides phosphoramidite derivatives of anthracene, phenanthrene, pyrene, stilbene, tetracene, or pentacene-derivatized nucleosides. The phosphoramidite derivatives are useful in the chemical synthesis of nucleic acids containing phenanthrene, anthracene, pyrene, stilbene, tetracene, or pentacene-derivatized nucleosides.

The present invention also provides intermediates useful in the synthesis of the subject nucleosides and subject phosphoramidite derivatives of anthracene, phenanthrene, pyrene, stilbene, tetracene or pentacene-derivatized nucleosides. The intermediates comprise an adduct of Hoffer's chlorosugar and the corresponding polycyclic aromatic hydrocarbon.

Another aspect of the invention is directed to methods for synthesizing phenanthrene, anthracene, pyrene, stilbene, tetracene or pentacene-derivatized nucleosides and their phosphoramidite derivatives. In another aspect of the invention, methods of preparing fluorescently-labeled DNA or RNA using the subject nucleosides and phosphoramidite derivatives are also provided.

Fluorescently tagged nucleic acids such as DNA and RNA having one or more subject fluorescent nucleosides incorporated within are also provided by the present invention.

The present invention further provides methods of detecting a target nucleic acid through hybridization (such as FISH) of complementary nucleic acid probes employing one or more of the subject fluorescent nucleosides incorporated within.

Both α and β configurations of the anthracene, phenanthrene, pyrene, stilbene, tetracene or pentacene derivatized nucleosides are provided as well as a method for epimerization of the α-anomers to β-anomers.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 6 schematically depicts a synthetic preparation of the compounds of the present invention.

FIG. 13 depicts the structures of complexes of triplex-forming oligonucleotides with the complementary target sequence 5'-dGAAAAGAAGA (SEQ ID NO:1).

FIG. 18 shows the nucleotide sequences of oligonucleotides P1, P2, P3, P5, C6 and C10 where P stands for a pyrene-derived nucleotide. Relative emission intensities are listed at the right.

DETAILED DESCRIPTION OF THE INVENTION

Figure 1A:
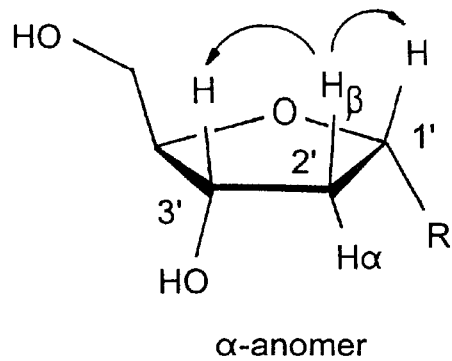
FIG. 1 is an Illustration of qualitivative differences in nuclear Overhauser enhancements observed for alpha-(left) and beta-anomers(right) of compounds 1–6. In alpha anomers, irradiation of the C-2'-β proton gives enhancements in both the C-1' and C-3' protons, while irradiation of the C-2'-α proton gives little or no enhancement for either. In the beta-anomers, irradiation of the C-2'-β proton gives enhancement only in the C-3' proton, while irradiation of the C-2'-α proton gives enhancement only in the C-1' proton.

The present invention provides fluorescent nucleoside analogs having polycyclic aromatic hydrocarbons such as anthracene, phenanthrene, pyrene, stilbene, tetracene, or pentacene attached to a sugar moiety. The aromatic hydrocarbon groups are attached to the C-1 (1') carbon of the sugar moiety in a nucleotide or nucleoside and act as DNA or RNA base analogs. Due to the location of the polycyclic aromatic hydrocarbon on the sugar moiety, the nucleoside analogs of the present invention stack neatly in an RNA or DNA helix and do not interfere with binding properties of surrounding complementary bases.

In accordance with the present invention, the anthracene, phenanthrene, pyrene, stilbene, tetracene, or pentacene may be substituted at various positions on their respective ring structures with one or more alkoxy, alkylamino or halide groups without altering the fluorescent properties of the nucleoside analog. Examples include but are not limited to methoxy, ethoxy, dimethylamino, diethylamino, nitro, methyl, cyano, carboxy, chloro, bromo, iodo, or amino groups.

In addition, the anthracene, phenanthrene, pyrene or other aromatic hydrocarbon may be attached at any available position on their respective ring structures to the C1 (1') position of a sugar moiety by a carbon-carbon bond. Both alpha and beta anomers of the anthracene, phenanthrene, pyrene, stilbene, tetracene or pentacene-derivatized nucleosides are provided by the present invention.

In one embodiment of the invention, the pyrene-derivatized deoxynucleoside has at least one of the following structures:

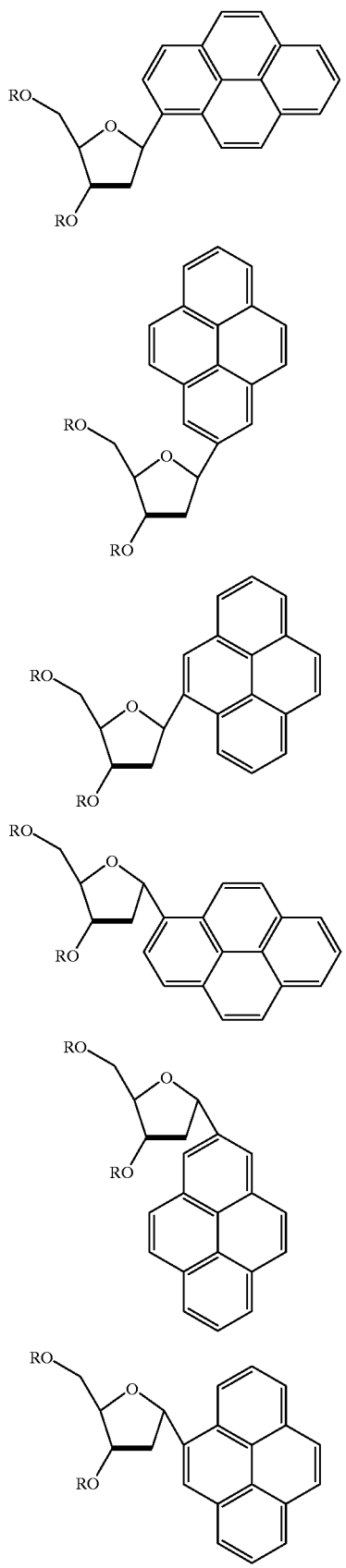

In another embodiment of the invention, the phenanthrene-derivatized deoxynucleoside has at least one of the following structures:
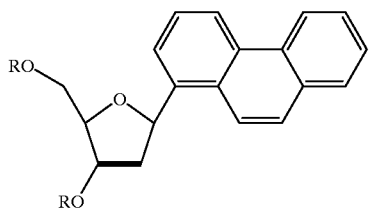
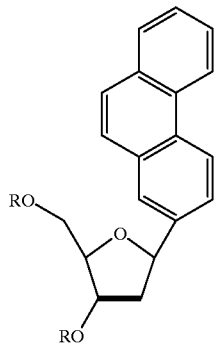
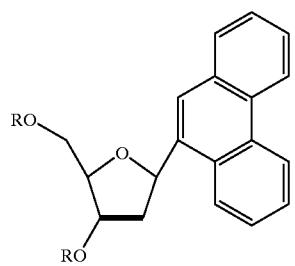
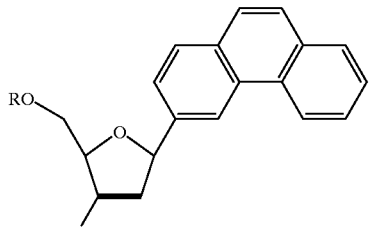
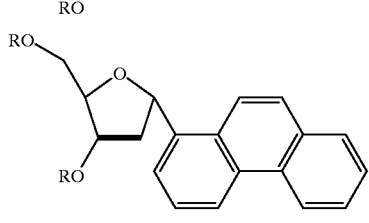
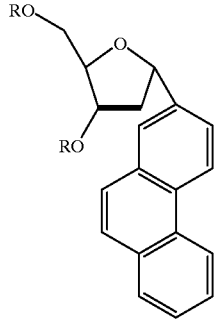
-continued
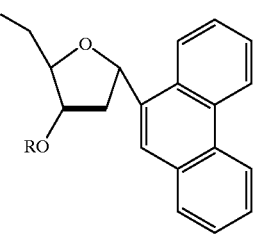
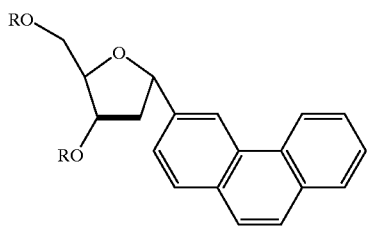
In yet another embodiment of the invention, the anthracene-derivatized deoxynucleoside has at least one of the following structures:
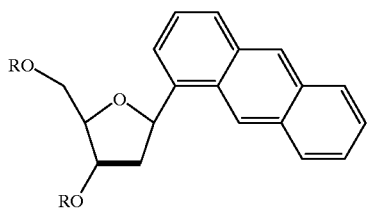
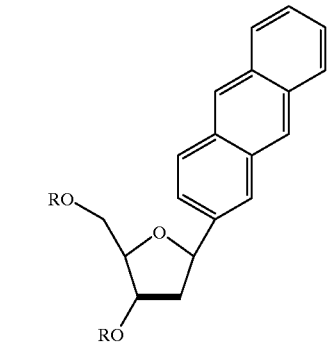
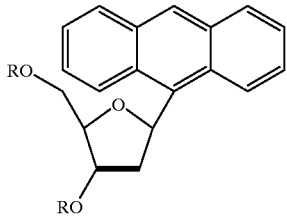
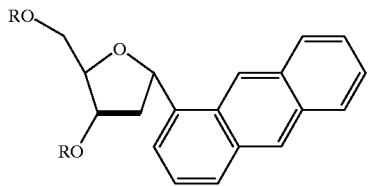

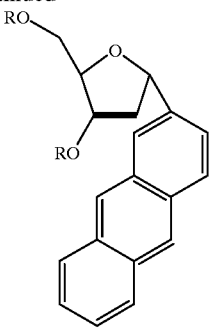
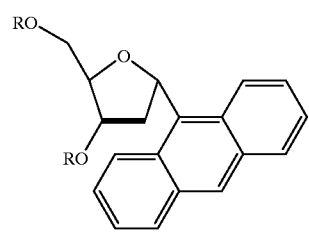
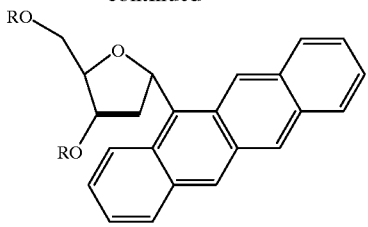
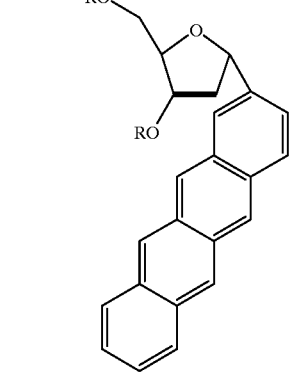
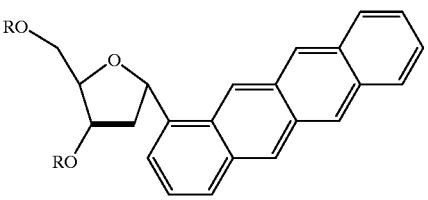
In another embodiment of the invention, the tetracene-derivatives deoxynucleoside has at least one of the following structures:
tetracene isomers
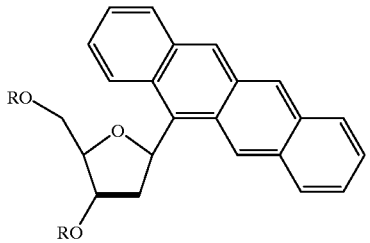
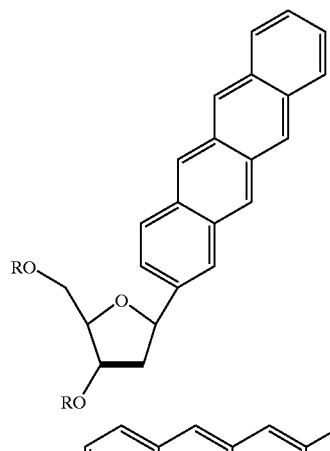
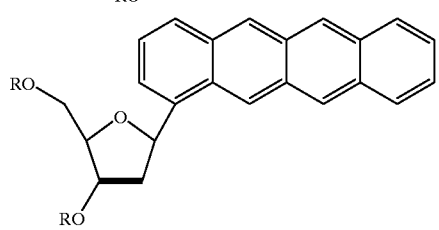
In still another embodiment of the invention, the pentacene-derivatized deoxynucleoside has at least one of the following structures:
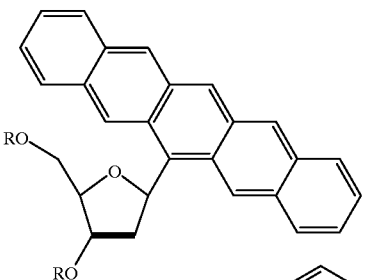
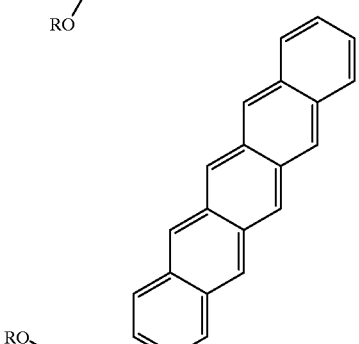
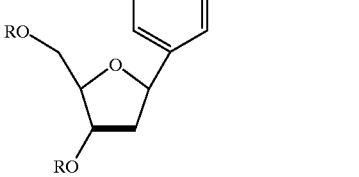

-continued
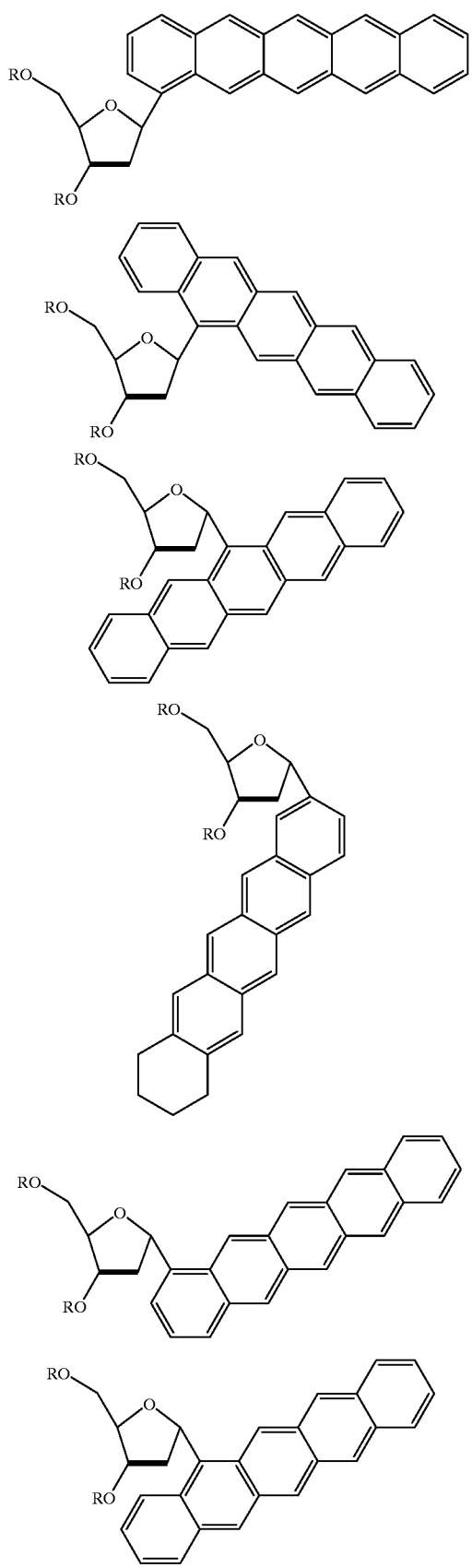
In another embodiment of the invention, the stilbene-derivatives deoxynucleoside has at least one of the following structures:
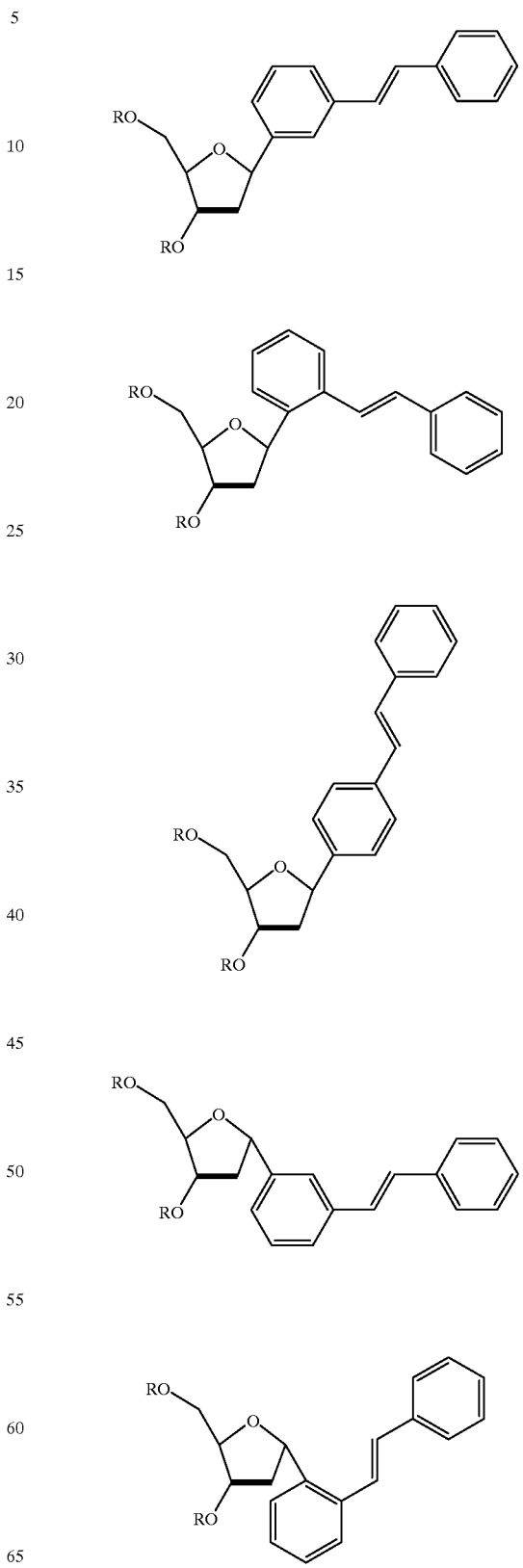

-continued

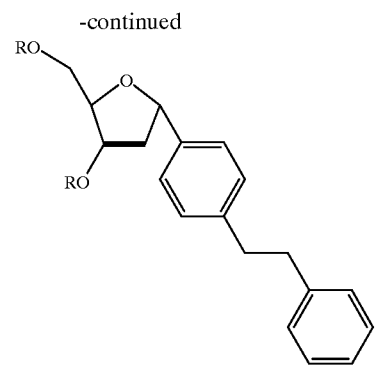

In yet another embodiment of the invention, the phenanthrene-derivatized nucleoside is α-9-phenanthrenyl deoxynucleoside having the structural formula:

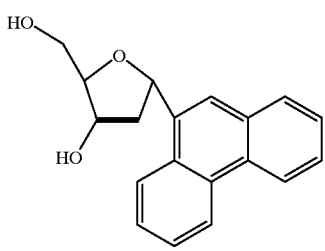

In another embodiment of the invention, the phenanthrene-derivatized nucleoside is β-9-phenanthrenyl deoxynucleoside having the structural formula:

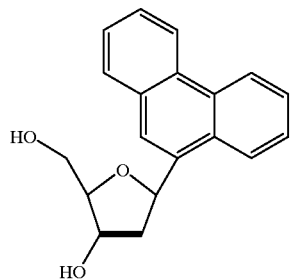

In still another embodiment of the invention, the pyrene-derivatized nucleoside is α-1-pyrenyl deoxynucleoside having the structural formula:

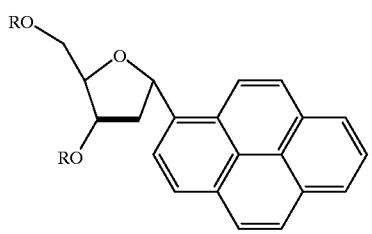

In yet another embodiment of the invention, the pyrene-derivatized nucleoside is β-1-pyrenyl deoxynucleoside having the structural formula:

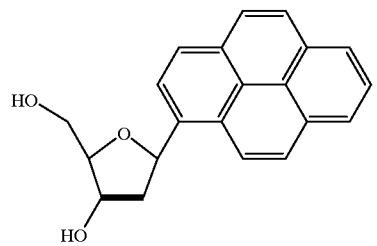

In yet another embodiment in the invention, the anthracene-derivatized nucleoside is α-1-anthracenyl deoxynucleoside having the structural formula:

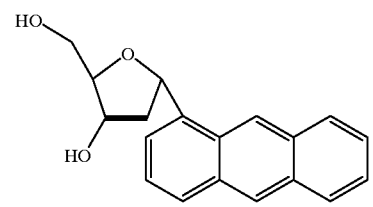

In yet another embodiment of the invention, the anthracene-derivatized nucleoside is β-1-anthracenyl deoxynucleoside having the structural formula:

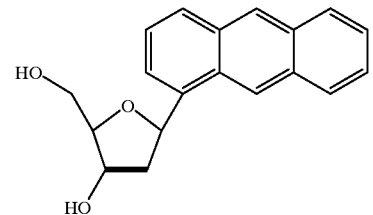

Useful intermediates provided by the present invention include the adduct of Hoffer's chlorosugar and the polycyclic aromatic hydrocarbon such as, for example, the anthracene, phenanthrene, pyrene, stilbene, tetracene, or pentacene-derivatized nucleoside 5'-3'-paratolueyl diester.

Other particularly useful intermediates provided by the present invention include, for example, the pyrene, anthracene, phenanthrene, stilbene, tetracene or pentacene 5'-dimethoxy trityl ether-3'-O-H-phosphorate.

Useful phosphoramidite derivatives provided by the present invention include N,N-diisopropyl-O-cyanoethyl phosphoramidite derivitized at the 3' alcohol of the pyrene, anthracene, phenanthrene, stilbene, tetracene or pentacene derivitized nucleoside.

The subject anthracene, phenanthrene pyrene, stilbene, tetracene or pentacene-derivatized nucleosides, when incorporated into a nucleic acid such as RNA or DNA, provide fluorescence at a range of 450–550 nm with a peak at 483 nm. In accordance with the present invention, it has been surprisingly found that two or more adjacent derivatized nucleosides form bright, long-wavelength excimers while stabilizing nucleic acid helices by their strong base stacking properties. Thus, the multilabel quenching problem associated with other fluorescent nucleoside tags is avoided by the present invention while providing a high sensitivity of detection.

The subject fluorescent nucleosides of the present invention can be synthesized by coupling polycyclic aromatic hydrocarbons to a sugar using a modification of the organocadmium strategy described in Schweitzer and Kool (1995) *J. Am. Chem. Soc.* 117:1863. The disclosure of this article and of all other articles cited in this application are incorporated herein as if fully set forth.

The C-nucleoside coupling involves the reaction of organocadmium or organozinc derivatives of the aromatic species with the well known α-chlorosugar synthon of Hoffer[19]. The steps involved in the glycosidic coupling of anthracene, pyrene, phenanthrene, stilbene, tetracene, or pentacene to a sugar is set forth in FIG. 6 where Ar is an aromatic hydrocarbon selected from the group consisting of anthracene, phenanthrene, pyrene, stilbene, tetracene or pentacene. This coupling results in a mixture of alpha and beta anomers in isolated yields of between about 54–81%. Alpha-anomeric C-nucleosides are the primary reaction products.

Toluoyl protecting groups may be removed in methanolic base. Thus, in accordance with the present invention, free unprotected nucleosides can be produced in as little as two steps: aromatic coupling and ester deprotection.

The alpha-anomers may be converted to the beta configuration by a third step, acid-catalyzed equilibration. A preferred acid catalyzed equilibration reaction uses benzenesulfonic acid in refluxing xylene, in the presence of a small amount of water. The alpha-anomers of the subject nucleoside analogs provide greater fluorescence and may therefore be preferred for fluorescent labeling purposes. The present invention also provides use of a string of the subject nucleoside analogs which can be attached to generally any compound via a chemical bridge such as a thiol group. Methods for joining molecules can be found, for example, in S. L. Beavcage and R. P. Iyer (1993) *Tetrahedron* 49:1925–1963.

The anthracene, phenanthrene, pyrene, stilbene, tetracene or pentacene-derivatized nucleosides of the present invention may be incorporated into an RNA or DNA strand during synthesis by any of a myriad of procedures known for making DNA or RNA. For example, such procedures include enzymatic synthesis and chemical synthesis. Chemical synthesis include solution or solid phase techniques.

Enzymatic methods of RNA oligonucleotide synthesis frequently employ Klenow, T7, T4, Taq or *E. coli* DNA polymerases as described in Sambrook et al. (1989, *Molecular Cloning: A Laboratory Manual*, Cold Spring Harbor Press, NY). Enzymatic methods of FNA oligonucleotide synthesis frequently employ SP6, T3, or T7 RNA polymerase as described in Sambrook et al. Reverse transcriptase can also be used to synthesize DNA from RNA (Sambrook et al.). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by PCR techniques as described, for example, by Saiki et al., 1988, *Science* 239:487.

Chemical synthesis of linear oligonucleotides is well known in the art and can be achieve by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases in addition to the nucleoside base analogs of the present invention are incorporated into the oligonucleotide, and particularly if modified phosphodiester linkages are used, then the synthetic procedures are altered as needed according to known procedures. In this regard, Uhlmann et al. (1990, Chemical Reviews 90:543–584) provide references and outline procedures for making oligonucleotides with modified based and modified phosphodiester linkages.

Synthetic, linear oligonucleotides may be purified by polyacrylamide gel electrophoresis or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn, et al., 1982, *Nuc. Acid. Res.* 10:4671). Sequencing methods are also available for RNA oligonucleotides.

In a preferred method, DNA oligonucleotides are synthesized by automated methods using a DNA synthesizer and β-cyanoethylphosphoramidite chemistry. Extended coupling times (10 minute) are preferably used for anthracene, phenanthrene, pyrene, stilbene, tetracene or pentacene-derivatized nucleoside residues. Oligomers may be purified by prepative denaturing polyacrylamide gel electrophoresis and isolated by methods known in the art such as the crush and soak method.

The subject fluorescent nucleosides of the present invention can be incorporated into a nucleic acid in order to achieve fluorescence labeling. Standard methods may be used to convert the unprotected nucleosides to 5'-dimethoxytrityl-protected derivatives. For example, the unprotected subject nucleosides may be co-evaporated with dry pyridine, then dissolved in pyridine and methylenechloride. A catalytic amount of DMAP, and both diisopropylethylamine and 4,4'-dimethoxytriryl (DMT) chloride is then added and the mixture stirred at room temperature for about eight hours. Hexanes are added and the mixture loaded on a flash silica gel column and the product, 5'-dimethoxytrityl-protected derivatives, eluted. These derivatives may then be converted into cyanoethyl phosphoramidite derivatives for incorporation into a nucleic acid sequence such as DNA or RNA.

The preparation of 3'-O-phosphoramidites from the 5'-dimethoxytrityl-protected anthracene, phenanthrene, pyrene, stilbene, tetracene or pentacene-derivatized nucleosides is achieved by methods well known in the art such as, for example, dissolving the protected nucleoside derivatives in dry methylene chloride and adding diisopropylethylamine and 2-cyanoethyl N,N,-diisopropylchlorophosphoramidite. The reaction mixture is stirred at room temperature for a period of about 4 hours after which hexanes are added. The mixture is then loaded to a flash silica gel column and the product eluted as an oil.

In accordance with the present invention, one or more of the subject nucleosides may be incorporated at various positions in an RNA or DNA sequence. For example, one or more subject nucleosides may be incorporated within a stretch of sequence so that the DNA or RNA fragment is effectively tagged towards the middle of the molecule. One or more subject nucleosides may also be incorporated near or at the end of an RNA or DNA sequence.

In another aspect of the invention, oligonucleotides may be designed to form triplexes with a single stranded target nucleic acid by folding into a hairpin configuration so that a loop of at least about five nucleotides separates the two strands. One or more anthracene, phenanthrene, pyrene, stilbene, tetracene or pentacene-derivatized nucleosides may be incorporated within the loop. This configuration is illustrated in FIG. 13.

In another aspect of the invention one or more anthracene, phenanthrene pyrene, stilbene, tetracene, or pentacene-derivatized nucleosides may be incorporated within a linear nucleic acid molecule, or at either or both the 5' or 3' ends of a linear nucleic acid molecule.

In a preferred embodiment, the subject fluorescent nucleosides are present in more than one position in an RNA or DNA. In a more preferred embodiment, at least two subject nucleosides are placed adjacent to one another within an RNA or DNA sequence. In another preferred embodiment, at least two subject nucleosides are placed adjacent to one another within a loop of a hairpin oligonucleotide.

In another preferred embodiment, the subject nucleosides are incorporated into a circular oligonucleotide. The loop domains which connect two opposing strands and thus enclose a circle have the subject nucleosides incorporated within.

In a more preferred embodiment, at least one subject nucleoside is incorporated into a DNA molecule (hairpin, circle or linear) adjacent to an adenine (A) base. In accordance with the present invention, greater fluorescence intensities may be achieved using three to five pyrenes adjacent to an A. More than five total subject nucleosides may be used within a nucleic acid molecule if groups of less than five of such nucleosides are separated such as in three to five nucleosides separated by an A, followed by three to five more subject nucleosides separated by another A, followed by three to five more subject nucleosides (P3AP3AP3; P4AP4AP4; or P5AP5AP5). Such groups may also be added to one or both ends of a nucleic acid molecule.

In another preferred embodiment, an odd number of subject fluorescent nucleosides is attached to or incorporated into a nucleic acid molecule. Thus, labeling a nucleic acid molecule with three, five or seven subject nucleosides is especially preferred.

The DNA and RNA sequences comprising anthracene, phenanthrene, pyrene, stilbene, tetracene or pentacene-derivatized nucleosides of the present invention are useful for detecting target nucleic acids in tissues, genomic material such as chromatin and chromosomes, solutions or immobilized on membranes. The fluorescently labeled nucleoside derivatives of the present invention are particularly useful when attached to a solid support such as controlled pure glass (cpg). Thus, the DNA and RNA sequences containing anthracene, phenanthrene pyrene, stilbene, tetracene or pentacene-derivatized nucleosides of the present invention hybridize to a target nucleic acid of sufficient complementarity in the detection of such targets by contacting the derivitized probe with the target in a sample to be tested for a time and under conditions sufficient to detectably hybridize the probe with the target. The present nucleoside derivatives are particularly useful in any technique which uses fluorescent-tagged oligonucleotides for detection. A rapidly growing diagnostic technique which involves fluorescence detection is fluorescence in situ hybridization (FISH). The method uses long, enzymatically synthesized DNA strands tagged with multiple fluorescent labels. These are hybridized to fixed chromosomes from a patient's cell, and if the gene in question is present, a colored fluorescent spot is visible on the chromosome by fluorescence microscopy. The method is used to detect whole genes such as the bcr/abl translocated gene in CML, or extra copies of genes in certain genetic diseases.

Small synthetic oligonucleotides are expected to have much higher sequence specificity than long traditional FISH probes. For FISH to work, a probe must be fluorescent-labeled brightly enough to detect under the microscope. Thus, an oligonucleotide must carry the equivalent of several (roughly ~8–40) fluorescent tags. The fluorescent nucleosides of the present invention give greater brightness with multiple labels. This method takes advantage of excimer emission from multiple pyrenes, for example, stacked together.

Specific applications of the subject fluorescent nucleosides in labeling nucleic acids include: fluorescent primers for automated DNA sequencing, fluorescent probes for flow cytometry, fluorescent probes for ELISA-like sandwich assays, fluorophores for measurement of protein-DNA binding, fluorescent primers for detection/identification after PCR, fluorescent probes for in situ hybridization/microscopy (RNA and DNA targets), measurement of cellular uptake of DNA, measurement of distance, orientation and dynamics in nucleic acid structures, and fluorescent probes for Southern/Northern blots and related assays.

Complementarity between nucleic acids is the degree to which the bases in one nucleic acid strand can hydrogen bond, or base pair, with the bases in a second nucleic acid strand. Hence, complementarity can sometimes be conveniently described by the percentage, i.e., proportion, of nucleotides which form base pairs between two strands. As used herein, "sufficient complementarity" means that a sufficient number of base pairs exist between a target nucleic acid and the anthracene, pyrene, phenanthrene, stilbene, tetracene or pentacene labeled nucleic acid of the present invention so that detectable binding is achieved.

When expressed or measured by percentage of base pairs formed, the degree of complementarity can range from as little as about 30–40% complementarity to full, i.e. 100%, complementarity. In general, the overall degree of complementarity between the target and labeled subject nucleic acid is preferably at least about 50%.

The degree of complementarity that provides detectable binding between the subject labeled nucleic acids and a target is dependent upon the conditions under which binding occurs. It is well known that binding, i.e., hybridization, between nucleic acid strands depends on factors besides the degree of mismatch between the two sequences. Such factors include the GC content of the region, temperature, ionic strength, the presence of formamide, and types of counter ions present. The effect that these conditions have upon binding is known to one skilled in the art. Furthermore, conditions are frequently determined by the circumstance of use. Binding conditions can be manipulated in vitro to optimize the utility of the subject fluorescent nucleic acids. A thorough treatment of the qualitative and quantitative considerations involved in establishing binding conditions that allow one skilled in art to design appropriate oligonucleotides for use under the desired conditions is provided by Belz et al., 1983 *Methods Enzymol.* 100:266–285 and by Sambrook et al.

Thus, for the present invention, one of ordinary skill in the art can readily design a fluorescently labeled nucleic acid sequence having one or more fluorescent nucleosides selected from the group consisting of anthracene, phenanthrene, pyrene, stilbene, tetracene and pentacene-derivatized nucleosides which exhibit sufficient complementarity to detectably bind to its target sequence. As used herein, "binding" or "stable binding" means that a sufficient amount of the nucleic acid is bound to its target to permit detection of that binding. In accordance with the present invention, binding can be detected by either physical or functional properties of the subject nucleic acid:target complex.

Binding between a target and a nucleic acid can be detected by any procedure known to one skilled in the art, including both functional or physical binding assays. Binding may be detected functionally by determining whether binding has an observable effect upon a biosynthetic process such as DNA replication, RNA transcription, protein translation or the like.

Physical methods of detecting the binding of complementary strands of DNA or RNA are well known in the art, and include such methods as DNase I or chemical footprinting, gel shift and affinity clavage assays, Northern blotting, dot blotting and light absorption detection procedures. Fluorescence methodologies include spectroscopy, fluorescence spectrophotometry and fluorescence assisted cell sorting (FACS), fluorescence microscopy, and digital imaging camera.

The binding between an oligonucleotide and its target nucleic acid is frequently characterized by the temperature at which 50% of the oligonucleotide is melted from its target. This temperature is the melting temperature ($T_m$). The higher $T_m$ means a stronger or more stable complex relative to a complex with a lower $T_m$.

In accordance with the present invention, observing fluorescence in the 300–900 nm range with the appropriate hybridization and washing conditions indicate binding of a fluoroscently labeled nucleic acid of the present invention to its target sequence.

In accordance with the present invention, binding of anthracene, pyrene, phenanthrene, stilbene, tetracene or pentacene-labeled nucleic acids to a target sequence can be observed by native gel shift experiments where the bound complexes are clearly visible under fluorescent light. For example, a nucleic acid:target complex having a single pyrene-based nucleoside appears deep blue in color while a nucleic acid:target complex having multiple pyrene-based nucleosides appear light blue to white in appearance, indicative of longer wavelength emission.

The following examples further illustrate the invention. For purposes of the following examples, compounds 1–6 and compounds 1a–6a are provided in FIG. 5. Compounds 1–6 are the β form of the molecule as shown and compounds 1a–6a are the α form of the molecule (not shown) in the Figure. All reference to compounds 1–6 and 1a–6a in the text therefore refer to those depicted structurally in FIGS. 5A through 5F.

EXAMPLE 1

Synthesis

The previously described method of C-nucleoside coupling[13] was utilized to generate the new aromatic nucleosides 1–4 (FIG. 5) as their bis-toluoyl esters (FIG. 6). The method involves the reaction of organocadmium derivatives of the aromatic species with the well-known α-chlorosugar synthon of Hoffer[19] (FIG. 6).

Glycosidic Coupling Reaction and Isolation of Major α-epimers as bis-p-toluoyl Esters of 1a–6a.

Dry THF (5 mL) was placed in a round-bottomed flask equipped with a condenser, drying tube and addition funnel. Magnesium turnings (0.3 g, 1.2 mmol) and a few crystals of iodine were added. 1-Bromopyrene (0.35 g, 1.2 mmol) was added to the mixture. Slight heating was needed (40° C.) to drive the reaction to completion. After formation of the Grignard reagent was complete (~1 hr), dry $CdCl_2$ (110 mg, 0.6 mmol) was added and the reaction mixture was continuously heated under reflux for 1 hr. 1'-α-chloro-3',5'-di-O-toluoyl-2'-deoxyribose[19] (0.51 g, 1.3 mmol) was then added to the above mixture in one portion. The solution was stirred at room temperature for 4 hr under an atmosphere of $N_2$. The solution was poured into 10% ammonium chloride (2×50 mL) and extracted with methylene chloride. The organic layers were washed with saturated sodium bicarbonate and brine and dried over anhydrous magnesium sulfate. The solution was filtered, concentrated and purified by flash silica gel chromatography eluting with hexanes-ethyl acetate (9:1). The major product 1a bis-toluoyl ester was obtained as a pale yellow oil (α-epimer, 48% isolated yield): $^1$HNMR ($CDCl_3$, ppm) δ 8.80 (2H, d, J=8.0), 8.72 (2H, d, J=8.0) 8.05 (1H, s), 7.92–8.00 (2H, m), 7.72–7.60 (4H, m), 7.58 (2H, d, J-8.0), 7.32 (2H, d, J-8.0), 6.96 (2, d, J-8.0), 6.16 (1h, dd, J-8.2, 6.0), 5.76 (1H, m), 4.98 (1H, m), 4.75–4.65 (2H, m), 3.30–3.22 (1H, m), 3.50–3.45 (1H, m), 3.44 (3H, s), 3.38 (3H, s); $^{13}$C NMR ($CDCl_3$, ppm) δ 21.3, 21.4, 39.2, 64.5, 76.2, 78.0, 82.5, 122.3, 122.9, 123.2, 123.6, 126.0, 126.3, 126.4, 126.6, 126.8, 127.0, 128.7, 128.8, 128.9, 129.0, 129.2, 129.4, 129.6, 129.8, 130.6, 131.4, 136.2, 143.5, 143.6, 165.8, 166.2; HRMS (FAB, 3-NBA matrix) calculated for $C_{37}H_{31}O_5$(M+1) 554.2093, found 554.2069.

2a bis-toluoyl ester (α-epimer, 43% isolated yield): $^1$H NMR ($CDCl_3$, ppm) δ 8.80 (2H, d, J=8.0), 8.72 (2H, d, J=8.0), 8.05 (1H, s), 7.92–8.00 (2H, m), 7.72–7.60 (4H, m), 7.58 (2H, d, J=8.0), 7.32 (2H, d, J=8.0), 6.96 (2H, d, J-8.0), 6.15 (1H, dd, J=8.2, 6.0), 5.76 (1H, m), 4.98 (1H, m), 4.75–4.65 (2H, m), 3.30–3.22 (1H, m), 3.50–3.45 (1H, m), 3.44 (3H, s), 3.38 (3H, s); $^{13}$C NMR, ($CDCl_3$, ppm) δ 21.3, 21.4, 39.2, 64.5, 76.2, 78.0, 82.5, 122.3, 122.9, 123.2, 123.6, 126.0, 126–3, 126.4, 126.6, 126.8, 127.0, 128.7, 128.8, 128.9, 129.0, 129.2, 129.4, 129.6, 129.8, 130.6, 131.4, 136.2, 143.5, 143.6, 165.8, 166.2; HRMS (FAB, 3-NBA matrix) calculated for $C_3H_{31}O5$ (M+1) 531.2172, found 531.2174.

3a bis-toluoyl ester (α-epimer, 52% isolated yield): $^1$H NMR ($CDCl_3$, ppm) δ 8.05 (2H, d, J=8.0), 7.95 (2H, m), 7.83 (2H, overlapped d), 7.71 (2H, d, J=8.0), 7.55 (3H, m), 7.32 (2H, d, J=8.0), 7.19 (2H, d, J=8.0), 6.10 (1H, dd, J=8.0, 6.0), 5.69 (1H, m), 4.90 (1H, m), 4.76–4.65 (2H, m), 3.28–3.18 (1H, m), 2,52–2.45 (IH, m), 2.48 (3H, s), 2.42 (3H, s); $^{13}$C NMR ($CDCl_3$, ppm) δ 21.4, 21.5, 39.5, 64.5, 76.2, 77.8, 82.2, 122.1, 122.9, 125.1, 125.3, 125.8, 126.6, 127.0, 128.7, 128.8, 128.9, 129.2, 129.4, 129.5, 129.9, 133.6, 137.9, 143.6, 165.8, 166.2; HRMS ((FAB, 3-NBA matrix) calcd for $C_{31}H_{29}O5$ (M+1) 481.2015, found 481.2025.

4a bis-toluoyl ester (α-epimer, 31% isolated yield): $^1$H NMR ($CDCl_3$,ppm) δ 8.02 (2H, d, J=8.0), 7.92–7.97 (4H m), 7.83 (2H, d, J=8.0), 7.52–7.60 (3H, m), 7.32 (2H, d, J=8.0), 7.05 (2H, d, J=8.0), 5.72 (1H, m), 5.62 (1H, dd, J=8.2, 6.0), 4.85 (1H, m), 4.76–4.65 (2H, m), 3.12–3.02 (1H, m), 2,52–2.45 (1H, m), 2.42 (3H, s), 2.38 (3H, s); $^{13}$CNMR (CDCl$_3$, ppm) δ 21.3, 21.4, 40.0, 64.4, 76.3, 80.2, 82.1, 122.1, 122.9, 125.1, 125.3, 125.8, 126.6, 127.0, 128.7, 128.8, 128.9, 129.2, 129.4, 129.5, 129.9. 133.6, 139.9, 143.8, 165.8, 166.3; HRMS (FAB, 3-NBA matrix) calculated for C$_{31}$H$_{29}$O5 (M+1) 481.2043, found 481.2015.

5a bis-toluoyl ester (α-epimer, 13% isolated yield): $^1$H NMR (CDCl$_3$, ppm) δ 8.02 (2H, d, J=8.0), 7.86 (1H, d, J=8-0), 7.45 (1H, s), 7.23–7.28 (5H, m), 6.95 (1H. s), 5.69 (1H, br s), 5.54 (1H, dd, J=8.0, 6.0), 4.81 (1H, br s), 4.69–4.56 (2H, m), 3.07–2.98 (1H, m), 2.43 (6H, s), 1.35 (3H, s); $^{13}$C NMR (CDCl$_3$, ppm) δ 18.3, 19.0. 19.1, 21.4, 39.1, 64.4, 76.3. 77.2, 81.6, 125.9, 126.7, 126.8, 128.8. 128.9, 129.5. 131.1, 131.5, 133.7, 135.0, 137.3, 143.5, 143.6. 165.9, 166.1; HRMS (FAB, 3-NBA matrix) calculated for C$_{30}$H$_{33}$O$_5$ (M+1) 472.2250, found 472.2234.

6a bis-toluoyl ester (α-epimer, 16% isolated yield): $^1$H NMR (CDCl3, ppm) δ 8.0 (2H, d, J=8.0), 7.72 (2H, d, J=8.0), 7.43 (1H, t, J=8.5), 7.27 (2H, d, J=8.0), 7.19 (2H, d, J=8.0), 6.76 (1H, d, J=8.0), 5.61 (1H, br s), 5.57 (1H, dd, J=8.0, 6.0), 4.74 (1H, br s), 4.57, (2H, t J=5.0), 3.02–2.93 (1H, m), 2.43 (3H, S), 2.23 (3H, s); $^{13}$C NMR(CDCl$_3$,ppm) δ 14.0, 20, 21.6, 39.4. 64.5, 74.8, 76.3, 82.5, 103.1 (t) 120.1 (dd), 125.2 (dd), 126.5, 126.8, 128.8, 129.9, 129.3. 129.5, 143.6, 143.8, 158.6, 158.7; HRMS (FAB, 3-NBA matrix) calculated for C$_{28}$H$_{26}$F2O$_5$Na 503.1646, found 503.1636.

Epimerization of 1',2'-dideoxy-1'-α-aryl-3',5'-di-O-toluoyl-D-ribofuranoses and Isolation of β-epimers A solution of 6a-bis-toluoyl ester (780 mg, 1.62 mmol) in toluene (50 mL) was added catalytic amount of benzene-sulfonic acid (~10%), 1 drop of concentrated H$_2$SO$_4$ and 2–4 drops of H$_2$O. The reaction mixture was refluxed under vigorous stirring for 4–6 hrs. The mixture was then poured into 5% aqueous NaHCO$_3$ (50 mL) and extacted with EtOAc (3×50 mL). The combined organic layers were dried over anhydrous MgSO$_4$ and evaporated. Flash colunm chromatography (eluent solution: 8:1 to 2:1 hexanes:EtOAc) of the crude mixmm gave 430 mg of 6-bis-toluoyl ester (β-epimer, 46% isolated yield): $^1$H NMR (CDCl$_3$, ppm) δ 8.0 (4H, 2xd, J=8.0), 7.35–7.25 (5H, m), 6.76 (1H, t, J=10.0), 5.64 (1H, d, J=5.2), 5.46, (1H, dd, J=10.2, 2.3), 4.78 (1H, dd, J=1.9, 11.8), 4.63 (1H, dd, J=1.9, 11.8), 4.54 (1H, m), 2.64 (1H, dd, J=2.6, 11.8), 2.43 (3H, s), 2.46 (3H, s), 2.23 (1H, m); $^{13}$C NMR (CDCl$_3$, ppm) δ 13.8, 22.0 (d), 40.1, 64.9, 74.9, 83.0, 103.0 (t), 120.1 (d), 124.5 (d), 127.3 (d), 128.6, 128.8 (d), 128.9 (d), 144.0 (d), 156.5 (d), 158.0 (d), 155.9 (d), 162.3 (d), 166.1 (d); HRMS (FAB, 3-NBA matrix) calculated for C$_2$H$_{26}$F2O$_5$, 481.1827, found 481.1853.

1 bis-toluoyl ester (β-epimer, 38% isolated yield): $^1$H NMR (CDCl$_3$, ppm) δ 8.36(1H, d, J=7.9), 8.31 (1H, d, J=7.9), 8.20–8.17 (3H, m), 8.13–8.05 (6H, m), 8.02 (2H, d, J=8.0), 7.37 (2H, d, J=8.0 ), 72.6 (2H, d, J-8.0), 6.34 (1H, dd, J=3.6, 10.8), 5.78 (1H, d, J=5.4), 4.84–4.88 (2H, m), 4.78–4.76 (1H, m), 2.94 (1H, dd, J=2.5, 13.9), 2.50 (3H, s), 2.46 (1H, m), 2.40 (3H, s); $^{13}$C NMR (CDCl$_3$, ppm), δ 21.4, 21.5, 41.3, 64.5, 77.1, 77.9, 82.7, 122.0, 122.4, 124.5, 124.8, 125.0, 125.6, 126.8, 126.9, 127.0, 127.2, 127.3, 127.5, 128.9, 129.0, 129.5, 129.6. 130.3, 130.6, 131.1, 133.9, 143.5, 143.9. 166.0, 166.2; HRMS (FAB, 3-NBA matrix) calculated for C$_{37}$H$_{31}$O$_5$ (M+1) 554.2093, found 554.2069.

2 bis-toluoyl ester (β-epimer, 28% isolated yield): $^1$H NMR (CDCl$_3$, ppm) δ 8.78 (1H, d, J=7.9), 8.70 (1H, d, J=7.9), 8.13–8.09 (4H, m), 8.03 (2H, d, J=8.0), 7.84 (1H, d, J=7.9), 7.77–7.60 (4H, m), 7.36 (2H, d, J=8.0), 7.18 (2H, d, J=8.0), 6.60 (1H, dd, J=3.5,10-5), 4.90 (1H, dd, J=1.9, 11.8), 4.84 (1H, dd, J=1.9, 11.8), 2.94 (1H, dd, J=5.1, 13.7), 2.49 (3H, s), 2.44–2.41 (1H, m), 2.38 (3H, s); $^{13}$C NMR (CDCl3, ppm) δ 21.4, 21.5, 40.4, 64.3, 76.9, 77.7, 82.4, 122.1, 122.8, 123.1, 123.4, 126.1, 126.4, 126.5, 126.8, 126.9, 128.7, 128.9, 129.0, 129.4, 129.5, 129.6, 129.8, 130.4, 131.3, 134.7, 143.5, 143.9, 166.0, 166.2; HRMS (FAB, 3-NBA matrix) calculated for C$_{35}$H$_{31}$O$_5$(M+1) 531.2172, found 531.2174.

3 bis-toluoyl ester (β-epimer, 37% isolated yield): 1H NMR (CDCl$_3$, ppm) δ 8.09–8.04 (3H, m), 7.97 (1H, d, J=8.0), 7.91 (1H, overlapped d, J=6.3, 6.2), 7.88 (1H, d, J=8.0), 7.51 (2H, overlapped d, J=6.7, 6.5), 7.46 (1H, d, J,=7.9), 7.34 (2H, d, J=8.0), 7.22 (2H, d, J=8.0), 6.02 (1H, dd, J=3.2, 10.7), 5.71(1H, d, J=5.9), 4.78–4.78 (2H, m), 4.70–4.71 (1H, m), 2.85(1H, dd, J=2.5, 13.8), 2.48(3H,s), 2.47(3H,s),2.39–2.37(1H,m); $^{13}$C NMR(CDCl$_3$, ppm) δ 21.4, 21.5, 40.6, 64.5, 77.0, 77.7, 82.4, 122.1, 122.8, 125.3, 125.4, 125.7, 125.9, 126.8, 126.9, 127.9, 128.6, 128.9, 129.0, 129.5, 130.2, 133.4, 136.3, 143.5, 143.9, 166.0, 166.2; HRMS (FAB, 3-NBA matrix) calculated for C$_{31}$H$_{29}$O5 (M+I) 481.2015, found 481.2025.

4 bis-toluoyl ester (β-epimer, 41% isolated yield): $^1$H NMR (CDCl$_3$, ppm) δ 8.06 (2H, d, J=8.0), 8.02 (2H, d, J=8.0), 7.91–7.77 (4H, m), 7.57–7.48 (3H, m), 7.32 (2H, d, J=8.0), 7.23 (2H, d, J=8.0), 5.70 (1H, d, J=5.7), 5.46 (1H, dd, J=1.6, 10.9), 4.77–4.75 (2H, m), 4.66–4.65 (1H, m), 2.66 (1H, dd, J=2.6, 13.8), 2.48 (3H, s), 2.42 (3H, s); $^{13}$C NMR, (CDCl$_3$, ppm) δ 21.3, 21.4, 41.6, 64.5, 77.1, 80.7, 82.9, 123.5, 124.5, 125.6, 125.9, 126.8, 126.9, 127.4, 127.7. 128.1, 128.9, 129.3, 129.4, 129.5, 132.9, 133.0, 137.9, 143.5, 143.8, 165.9, 166.2; HRMS (FAB, 3-NBA matrix) calculated for C$_{31}$H$_{29}$O$_5$ (M+1) 481.2043, found 481.2015.

5 bis-toluoyl ester (β-epimer, 54% isolated yield): $^1$H NMR (CDCl$_{31}$ ppm) δ 8.02 (4H, 2×d, J=8.0), 7.35–7.23 (5H, m), 6.92 (1H, s), 5.62 (1H, d, J=5.6), 5.42 (1H, dd, J=3.5, 10.8), 4.78 (1H, dd, J=1.9, 11.8), 4.70 (1H. dd, J=1.8, 11.8), 4.55 (1H, m), 2.56 (1H, dd, J=2.5, 14.0), 2.43 (3H, s), 2.46 (3H, s), 2.23 (1H, m); $^{13}$C NMR (CDCl$_3$, ppm) δ 18.2, 19.5, 22.1 (d), 41.0, 65.0, 82.5, 126.2, 127.0 (d); 128.6 (d), 128.8 (d), 132.1 (d), 135.5, 136.2, 1414.0, 144.5, 165.5, 166.0; HRMS (FAB, 3-NBA matrix) calculated for C$_{30}$H$_{32}$O$_5$ 472.2250, found 472.2234.

Deprotection of 1',2'-dideoxy-1'-aryl-3',5'-di-O-toluoyl-β-D-ribofuranoses

A solution of 1 bis-toluoyl ester (360 mg, 0.65 mmol) in methanol (5 mL) was added NaOMe (in methanol, 25%, 0.5 mL, 3 eq). The reaction mixrure was stirred for 4–6 hr. Solid ammonium chloride was added until the pH was 8. The mixture was then poured into water and extracted with EtOAc (3×15 mL). The combined organic) layers were dried over anhydrous MgSO$_4$ and evaporated. Flash column chromatography (eluent; EtOAc) of the crude mixture gave 165 mg of nucleoside 1 (β-epimer, 78%); $^1$H NMR (CDCl$_3$, ppm) δ 8.35 (1H, d, J=8-0), 8.31–8.14 (4H, m), 8.08–8.02 (3H, m), 6.25 (1H, dd, J=2.8, 10.4), 4.62 (1H, m), 4.28 (1H, m), 4.02–3.98 (2H, m), 2.64 (1H, dd, J=1.0, 2.6, 13.4), 2.02 (2H, broad s, 2×OH); $^{13}$C NMR (CDCl$_3$, ppm) δ 44.5, 63.8, 74.3, 78.2, 88.9, 123.3, 123.7, 125.5, 125.6, 125.7, 126.0, 127.9, 128.1, 128.2, 128.3, 128.4, 128.5, 128.6, 131.7, 131.8, 136.5; HRMS (FAB, 3-NBA matrix) calculated for C$_{23}$H$_{20}$O$_3$ 318.1256, found 318.1251.

nucleoside 2, (β-epimer, 74%): $^1$H NMR (CDCl$_3$, ppm) δ 8.78 (1H, d, J=8.0), 8.68 (1H, d, J=8.0), 8.12 (1H, d, J=8.0), 7.90 (2H, m), 7.77–7.62 (4H, m), 5.95 (1H, dd, J=2.8, 10.4), 4.59 (1H, m), 4.22 (1H, m), 4.0 (1H, dd, J=3.2, 13.2), 3.95 (1H, dd, J=3.1, 13.4), 2.62 (1H, ddd, J=1.0, 5.2, 13.4), 2.25 (1H, m), 1.6 (2H, broad s, 2×OH); $^{13}$C NMR (CDCl$_3$, ppm) δ 43.5, 63.8, 74.0, 78.0, 88.5, 123.4, 123.5, 124.0, 124.8, 127.1, 127.3, 127.4, 127.5, 129.6, 130.8, 131.0, 131.6, 132.8, 137.1; HRMS(FAB,3-NBA matrix) calculated for $C_{19}H_{18}O_3$ 294.1256, found 294.1250.

nucleoside 3 (β-epimer, 50%): $^1$H NMR (CDCl$_3$, ppm) δ 8.06 (1H, d, J=8.0), 7.88 (1H, d, J=8.0), 7.80 (1H, d, J=8.0), 7.66 (1H, d. J=8.0), 7.55–7.46 (3H, m), 5.92 (1H, dd, J=2.6, 10.0), 4.52 (1H, m), 4.15 (1H, m), 3.92–3.86 (2H, m), 2.54 (1H, dd, J=2.8, 13.3), 2.18 (1H, m), 2.02 (2H, broad s, 2×OH); $^{13}$C NMR (CDCl$_3$, ppm) δ 43.0, 63.0, 74.0, 77–0, 123.2, 124.0, 125.2, 125.4, 127.0, 127.5, 130.2, 134.8, 138.0; HRMS (FAB, 3-NBA matrix) calculated for $C_{15}H_{16}O_3$ 244.1099, found 244.1105.

nucleoside 4 (β-epimer, 68%): $^1$H NMR (CDCl$_3$, ppm) δ 7.85–7.80 (4H, m), 7.50–7.42 (3H, m), 5.35 (1H, dd, J=2.8, 10.2), 4.43 (1H, m, 4.06 (1H, m), 3.77 (2H. m), 2.6 (2H, broad s, 2×OH), 2.33 (1H, ddd, J=1.0, 5.6, 13.4), 2.02 (1H, m); $^{13}$C NMR (CDCl$_3$, ppm) δ 44.6, 63.9, 74.3, 81.5, 89.1, 125.1, 125.6, 126.6, 128.4, 128.6, 128.9, 134.3. 134.5, 140.4; HRMS (FAB, 3-NBA matrix) calculated for $C_{15}H_{16}O_3$ 244.1099, found 244.1110.

nucleoside 5 (β-epimer, 93%): $^1$H NMR (CDCl$_3$, ppm) δ 7.20 (1H, s), 6.97 (1H, s), 5.38 (1H, dd, J=2.8, 10.4), 4.43 (1H, m), 4.01 (1H, m), 3.82 (2H, m), 2.32 (3H, s), 2.26 (3H, s), 2.24 (3H, s), 1.99 (1H, m), 1.90 (2H, broad s, 2×OH); $^{13}$C NMR (CDCl$_3$, ppm) δ 19.0, 19.5, 19.6, 41.6, 63.0, 74.0, 77.0, 87.0, 126.2, 126.3, 131.2, 131.6. 134.1. 135.2, 137.0; HRMS (FAB, 3-NBA matrix) calculated for $C_{14}H_{20}O_3$ 237.1491, found 237.1484.

nucleoside 6 (β-epimer, 89%): $^1$H NMR (CDCl$_3$, ppm) δ 7.46 (1H, t, J=10), 6.82 (1H, t, J=10), 5.31 (1H, dd, J=2.8, 10.4), 4.32 (1H, m), 3.92 (1H, m), 3.68 (2H, m), 2.22 (3H, s), 1.89 (1H, m), 1.78 (2H, broad s, 2×OH); $^{13}$C NMR (CDCl$_3$, ppm) δ 12.2, 41.9, 62.2, 72.5, 73.2, 87.2, 101.59, 101.9, 102.3, 119.8, 119.9, 120.1, 124.1, 124.3, 128.8, 128.9, 129.0; HRMS (FAB, 3-NBA matrix) calculated for $C_{12}H_{14}F_2O_3Na$ 267.0809, found 267-0812.

Preparation of 5'-O-tritylated β-C-nucleosides

Synthesized nucleoside 1 (165 mg, 0.52 mmol) was co-evaporated with dry pyridine (4 mL) twice and then dissolved in 5 mL of pyridine and 4 mL of methylenechloride. To the above mixture was added catalytic amount of DMAP, diisopropylethylamine (0.14 mL, 1.5 eq) and 4,4'dimethoxytrityl (DMT) chloride (320 mg, 1.8 eq). The mixture was stirred at room temperature for 8 h. Hexanes (5 mL) was added and the mixture was loaded on flash silica gel column (pre-equilbrated with 5% triethylamine in hexanes) and eluted (5:1 Hexanes:EtOAc to 2:1 Hexanes:EtOAc). The product 1 DMT ether was obtained as a yellowish foam in 64% yield (200 mg, 0.32 mmol): $^1$H NMR (CDCl$_3$, ppm) δ 8.34 (2H, overlapped d, J=8.0), 8.24–8.02 (7H, m), 7.56 (2H, overlapped d, J=8.0). 7.45–7.27 (7H, m), 6.86 (4H, d, J=8.0), 6.52 (1H, d, J=6.2), 6.24 (1H, dd, J=2.6, 10.4), 4.60 (1H, m), 4.30 (1H,m ), 3.81 (6H, s), 3.56 (2H, m), 2.64 (1H, m), 2.30 (1H, m). $^{13}$C NMR 400 MHz (CDCl$_3$, ppm) δ 43.9, 55.2, 64.5, 74.5, 77.5, 86.4 (d), 113.2, 122.8, 123.0, 124.8 (d), 125.0, 125.2, 125.9, 126.9, 127.2, 127.5, 127.6, 127.7, 128.0, 128.4, 130.2, 130.3, 130.6 (d), 131.5, 135.5, 136.1, 145.0, 158.5; HRMS (FAB, 3-NBA matrix) calculated for $C_{42}H_{36}O_5$ 620.2564, found 620.2563.

2 DMT ether (280 mg, 59%): $^1$H NMR (CDCl$_3$, ppm) δ 8.78 (1H, d, J=8.0), 8.68 (1H, d, J=8.0), 8.07 (2H, m), 7.8 (1H, d, J=8.0), 7.80–7.24 (12H, m), 6.84 (4H, overlapped d, J=8.0), 5.94 (1H, dd, J=2.9, 10), 4.52 (1H, m), 4.22 (1H, m), 3.8 (6H, s), 3.50 (2H, m), 2.61 (1H, ddd, J=1.0, 5.2, 13.4), 2.25 (1H, m); $^{13}$C NMR 400 MHz (CDCl$_3$, ppm) δ 42.6, 55.1, 64.2, 74.1, 77.1 (obscured by solvent), 85.6, 86.0, 113.1, 122.3, 122.8, 123.2, 124.0, 126.2, 126.4. 126.5 (d), 126.8, 127.8, 128.2, 128.8, 129.7, 129.9, 130.1, 131.5, 136.0 (d), 136.2, 144.9, 155.8; HRMS (FAB, 3-NBA matrix) calculated for $C_{40}H_{36}O_5$ 596.2564. found 596.2563.

3 DMT ether (50 mg, 52%): $^1$H NMR (CDCl$_3$, ppm) δ 8.15 (1H, d, J=8.0), 7.9 (1H, d, J=8.0), 7.8 (1H, d, J=8.0), 7.65 (1H, d, J=8.0), 7.49–7.45 (3H, m), 5.94 (1H, dd, J=2.9, 10), 4.53 (1H, m), 4.25 (1H, m), 3.8 (3H, s), 3.42 (2H, m), 3.02 (3H, s), 2.58 (1H, ddd, J=1.0, 5.2, 13.4), 2.18, (1H, m); $^{13}$C NMR 400 MHz (CDCl$_3$; ppm) δ 42.9, 55.1, 64.3, 74.3, 77.1 (obscured by solvent), 85.8, 86.2, 113.1, 122.2, 123.4, 125.4, 125.5, 125.9, 126.8, 127.7, 127.8, 128.2, 128,7, 130.1, 130.4, 133.6, 136.0, 137.7, 144.9, 158.4; HRMs (FAB, 3-NBA matrix) calculated for $C_{36}H_{34}O_5$ 546.2407, found 546.2406.

4 DMT ether (200 mg, 66%): $^1$H NMR (CDCl$_3$, ppm) δ 7.83–7.94 (4H, m), 7.56–7.27, (11H, m), 6.87 (4H, overlapped d, J=8.0), 5.41 (1, dd, J=2.9, 10), 4.52 (1H, m), 3.82 (6H. s), 3.42 (2H, m), 2.38 (1H, dd, J=2.7, 13.4), 2.21 (1H, m).

5 DMT ether (311 mg, 92%): $^1$H NMR (CDCl$_3$, ppm) δ 7.52 (2H, d, J=8.0), 7.43–7.24 (7H, m), 6.94–6.84 (6H, m), 5.34 (1H, dd, J=2.9, 9.8), 4.42 (1H, m), 4.18 (1H, m), 3.80 (6H, s), 3.40 (2H, m), 2.64 (1H, m), 2.29 (3H, s), 2.23 (3H. s), 2.18 (3H, s), 2.0 (1H, m); $^{13}$C NMR (CDCl$_3$, ppm) δ 19.6, 19.8, 19.9, 43.1, 55.0, 64.0, 75.0, 82.2, 116.2, 125.3, 125.4, 125.6, 125.7, 130.01, 132.1, 132.2, 134.2, 135.2, 136.5, 145.0, 158.2; HRMS (FAB, 3-NBA matrix) calculated for $C_{35}H_{37}O_5$ 538.2719, found 538-2690.

6 DMT ether (350 mg, 88%): $^1$H NMR (CDCl$_3$, ppm) δ 7.46 (1H, d, J=8.0), 7.39–7.24( 5H, m), 6.83 (2H, overlapped d, J=8.0), 6.74 (1H, dd, t=9.8, 8.6), 5.38 (1H, dd, J=2.9, 9.9), 4.42 (1H, m), 4.06 (1H, m), 3.80 (6H, s), 3.38 (2H, m), 2.38 (1H, dd, J=2.5. 13.4). 21 (1H, m); $^{13}$C NMR (CDCl$_3$, ppm) δ 29.4, 42.5, 54.9, 64.3, 73.3, 74.3, 85.65, 102.3, 102.7, 103.0, 112.8, 115.0, 126.5, 127.5, 1127.6, 127.9, 129.1, 129.8, 128.9, 135.0, 145.0. 158.9; HRMS (FAB, 3-NBA matrix) calcd for $C_{33}H_{32}F_2O_5$ 569.2115, found 569.2131.

Preparation of 3'-0-phosphoramidites

The 5'-O-tritylated compound 1 DMT ether (200 mg, 0.32 mmol) was dissolved in 4 mL of dry methylene chloride and this was added diisopropylethylamine (0.22 mL, 1.2 mmol) and 2-cyanoethyl N,N,-diisopropylchlorophosphoramidite (0.11 mL, 0.48 mmol). The reaction mixture was stirred at root temperature for 4h Hexanes (4 mL) was added and the mixture was loaded to the flash silica gel column (pre-equilibrated with 5% triethylamin in hexanes) and eluted. The product was obtained as an oil DMT phosphoramidite 1 (210 mg, 81%): $^1$H NMR (CDCl$_3$, ppm) δ 8.44–8.33 (2H, m), 8.25–8.00 (7H, m), 7.62–7-22 (9H, m), 6.92–6.79 (4H, m), 6.28–6.20 (1H unresolved m), 4.69 (1H, m), 4.45 (1H, m), 4.0–3.2 (12H, m), 2.80 (1H, m), 2.69 (2H,t), 2.32 (1H, m), 1.15 (12H, m); $^{13}$C NMR 400 MHz (CDCl$_3$, ppm) δ 20.3 (m), 24.6 (m), 43.2 (m), 55.2, 58.3 (d), 64.1 (d), 75.8 (d), 76.0 (d), 77.9, 85.6 (d), 86.3, 113.2, 117.7 (d), 122.8 (d), 123.1 (d), 124.8 (d), 125.1, 125.2, 125.9, 126.8, 127.1, 127.5, 127.6 (d), 127.8 (d), 127.9, 128.4, 130.3, 130.7 (d), 131.4, 135.4, 136.1 (d), 145.1, 158.5; HRMS (FAB, 3-NBA matrix) calculated for $C_{51}H_{54}N_2O_6P$ (M+H) 821.3722, found 821.3720.

2 DMT phosphoramidite (280 mg, 77%): 1H NMR (CDCl$_3$, ppm), 8.78 (1H, d, J=8.0), 8.68 (1H, d, J=8.0), 8.07 (2H, m), 7.8 (1H. d, J=8.0), 7.80–7.24 (12H, m), 6.84 (4H, overlapped d, J=8.0), 5.94 (1H, overlapped dd, J=2.9,10), 4.62 (1H, m), 4.40 (1H, m), 3.9 (2H, m), 3.8 (6H, s), 3.50 (2H, m), 3.83 (3H, s), 3.77 (3H, s), 3.66–3.45 (3H, m), 3.42–3.38 (2H, m), 2.82, (2H, t, J=5.6), 2.52 (3H, t, J=5.6), 2.16 (1H, m), 1.20–1.05, (12H, m); $^{13}$C NMR 400 MHz (CDCl$_3$, ppm) δ 20.0 (m), 24.5 (m), 42.0, 43.2 (m), 55.1, 58.4 (m), 63.9 (d), 75.3 (d), 75.8 (d), 77.2 (obsured by solvent), 85.0 (m), 86.2, 113.1, 117.5, 122.4, 123.0 (d), 123.2 (d), 124.1 (d), 126.2. 126.4 (d), 126.6 (d), 126.7 (d), 127.8, 128.3 (d), 128.8 (d), 129.7 (d), 129.9, 130.1 (d), 130.6, 131.6, 136.1 (m), 144.9, 158.4: HRMS (FAB, 3-NBA matrix) calculated for $C_{49}H_{53}N_2O_6PNa$ 819.3537, found 819.3539.

3 DMT phosphoramidite (48 mg, 50%): $^1$H NMR (CDCl$_3$, ppm) δ 8.10 (1H, d, J=8.0), 7.9 (1H, d, J=8.0), 7.8 (1H, d, J=8.0), 7.52–7.24 (9H, m), 6.82 (4H, overlapped d, J=8.0), 5.91 (1H, overlapped dd, 2×isomers), 4.6 (1H, m), 4.38 (1H, m), 3.83 (3H. s), 3.77 (3H. s), 3.66–3.45 (3H, m), 3.42–3.38 (2H, m), 2.82 (2H, t, J=5.6), 2.52 (3H, t, J=5.6), 2.16 (1H, m), 1.20–1.05, (12H, m): $^{13}$C NMR, 400 MHz (CDCl$_3$, ppm) δ 20.3 (m), 24.5 (m), 42.0. 43.1 (m), 55.1, 58.4 (m), 63.9 (d), 75.1 (d), 76.2 (d), 77.1 (obscured by solvent), 85.0 (m), 86.1, 113.0, 122.3 (d), 123.4 (d), 125.4, 125.6 (d), 126.0 (d), 126.8 (d), 127.7, 128.2 (d), 128.6 (d), 130.1 (d), 130.5 (d), 133.6 (d), 136.0 (d), 137.5, 144.9, 158.4; HRMS (FAB, 3-NBA matrix) calculated for $C_{45}H_{52}N_2O_6P$ (M+H) 747.3565, found 747.3563.

4 DMT phosphoramidite (170 mg, 65%): $^1$H NMR (CDCl$_3$, ppm) δ 7.91 (1H, s), 7.83–7.79 (4H, m), 7.56–7.27 (11H, m), 6.87 (4H, overlapped d, J=8.0), 5.39 (1H, dd, J=2.9, 10), 4.58 (1H, m), 4.30 (1H, m), 3.90 (2H, m), 3.83 (3H, s), 3.77 (3H, s), 3.66–3.45 (3H, m), 3.42–3.38 (2H, m), 2.82 (2H, t, J=5.6), 2.52 (3H, t, J=5.6), 2.16 (1H, m), 1.20–1.05 (12H, m)

5 DMT phosphoramidite (380 mg, 89%): $^1$H NMR (CDCl$_3$, ppm) δ 7.54 (2H, 5 overlapped d, J=8.0), 7.45–7.40 (4H, m), 7.36–7.22 (3H, m), 6.98 (1H, s), 6.90–6.82, (4H, m), 5.37 (1H, dd, J=2.9, 10), 4.56 (1H, m), 4.22 (1H, m), 3.82 (6H, s), 3.66–3.45 (3H, m), 3.42–3.38 (2H, m), 2.82 (2H, t, J=5.6), 2.48 (1H, m), 2.29, (3H, s), 2.24 (3H, s), 2.18 (3H, S), 1.99 (1H, m), 1.28 (1H, m), 1.20–1.05 (12H m); $^{31}$P NMR (CDCl$_3$, ppm) δ 148.9, 148.4; HRMS (FAB, 3-NBA matrix) calculated for $C_{44}H_{55}N_2O_6P$ 739.3876, found 739.3870.

6 DMT phosphoramidite (420 mg, 84%): $^1$H NMR (CDCl$_3$, ppm) δ 7.51 (2H, m), 7.42–7.22 (9H, m), 6.84 (4H, overlapped d, J=8.0), 6.78 (1H, dd, J=9.0, 8-6), 5.38 (1H, dd, J=2.9, 10), 4.54 (1H, m), 4.22 (1H, m), 3.82 (6H, s), 3.66–3.45 (3H, m), 3.42–3.38 (2H, m), 2.82 (2H, t, J=5.6), 2.50, (2H, t J=5.6), 2.05 (1H, m), 1.20–1.05 (12H, m); $^{31}$P NMR (CDCl$_3$, ppm) δ 148.9, 148.3; HRMS (FAB, 3-NBA matrix) calculated for $C_{42}H_{49}F_2N_2O_6P$ 769.3194, found 769.3209.

As seen in reactions with benzene derivatives,[13] coupling with the larger polycyclic aromatics yields a mixture of alpha- and beta-anomers in good overall yields (54–81% isolated yields). The major isomer in all four cases is formed with retention of configuration; thus, alpha-anomeric C-nucleosides (the p-toluoyl esters of 1a, 2a, 3a, 4a of FIG. 5) are the primary products. Measured ratios of the two isomers (by NMR integration) ranged from 5:1 (α:β) for the I-naphthyl derivative to 10:1 for the 9-phenanthrenyl derivative. The configuration at the C-1' carbons of all isomers was determined by analysis of H1'–H2' coupling constants for the protected nucleosides, by $^1$H-nuclear Overhauser experiments on the deprotected nucleosides, and by correlation with an x-ray crystal structure of one of the α-anomeric compounds (see below).

Although the desired beta-anomers (the toluoyl esters of 1–4, FIG. 5) could also be isolated from this coupling reaction, the yields were less than ideal. Studies were thus undertaken to find conditions under which the predominant alpha-anomers could be converted to the desired beta-configuration. It was anticipated that acidic conditions might allow epimerization at the C-I position by reversible ring-opening. Experimentation with several sets of conditions revealed that benzenesulfonic acid in reflexing xylene, in the presence of a small amount of water, did indeed result in ready equilibration of the alpha-anomers to mixtures of beta- and alpha-isomers after several hours. Addition of a small amount of water was found to be necessary for the isomerization. 1The equilibration was then carried out for all four alpha-isomers (1a, 2a, 3a, 4a of FIG. 5) as their bis-toluoyl esters. The isomerization was also tested on two previously reported substituted benzene nucleosides (the toluoyl esters 5a, 6a) to test the scope of the reaction. Significantly, the major component of each mixture after equilibration was in all cases the desired beta-anomer (1–6 of FIG. 5). The ratios of beta-to alpha-isomers ranged from 4:1 for the trimethyl-benzene derivative to 2.5:1 for the 1-naphthyl derivative. Isolated yields of the desired beta-anomers after column chromatography ranged from 28–54%. The alpha anomers and mixed fractions could be reisolated and recycled in the isomerization if desired. Interestingly, the deprotected free nucleosides themselves did not undergo any observable isomerization under these conditions, even at extended reaction times.

Figure 7:
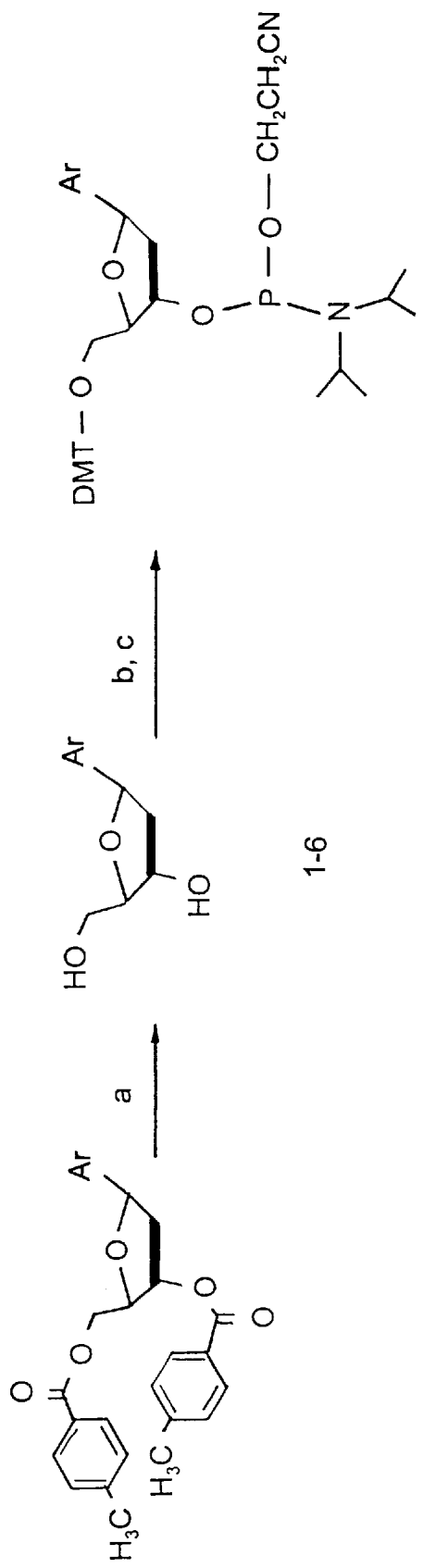
FIG. 7 schematically depicts a synthetic preparation of the compounds of the present invention.
Figure 8:
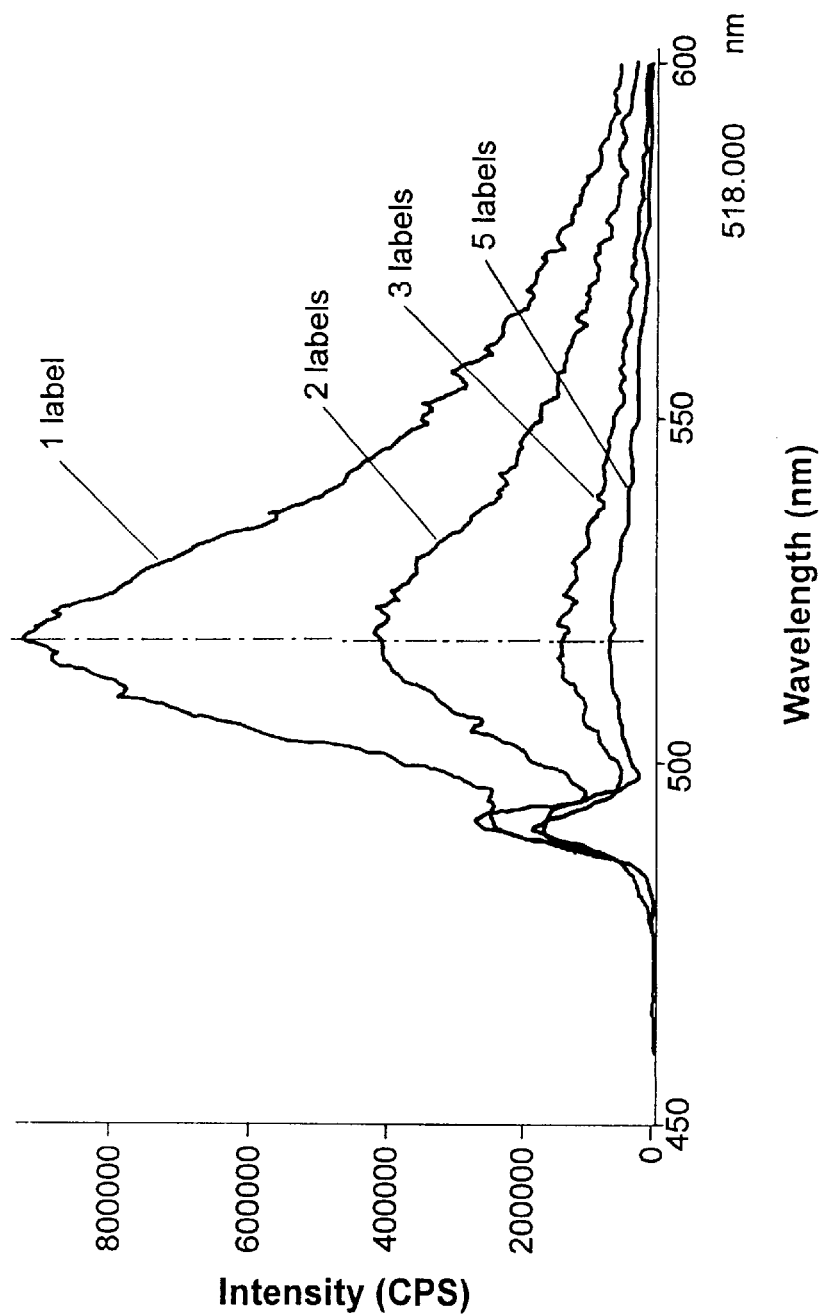
FIG. 8 is the emission spectra of oligos containing 1, 2, 3 and 5 fluoresceins from commercially available phosphoramidite. Strong quenching occurs with multiple labels.

With the new method for epimerization to beta-anomeric configuration in hand, the synthetic scheme made possible the facile generation of the six aromatic C-nucleosides (1–6 of FIG. 5) in generally good yields (FIG. 7). The toluoyl protecting groups were removed in methanolic base with yields ranging from 50–78%. Following this overall scheme, the free unprotected nucleosides were produced in a total of only three steps (aromatic coupling, isomerization, ester deprotection).

EXAMPLE 2

Structural Assignments

Figure 2:
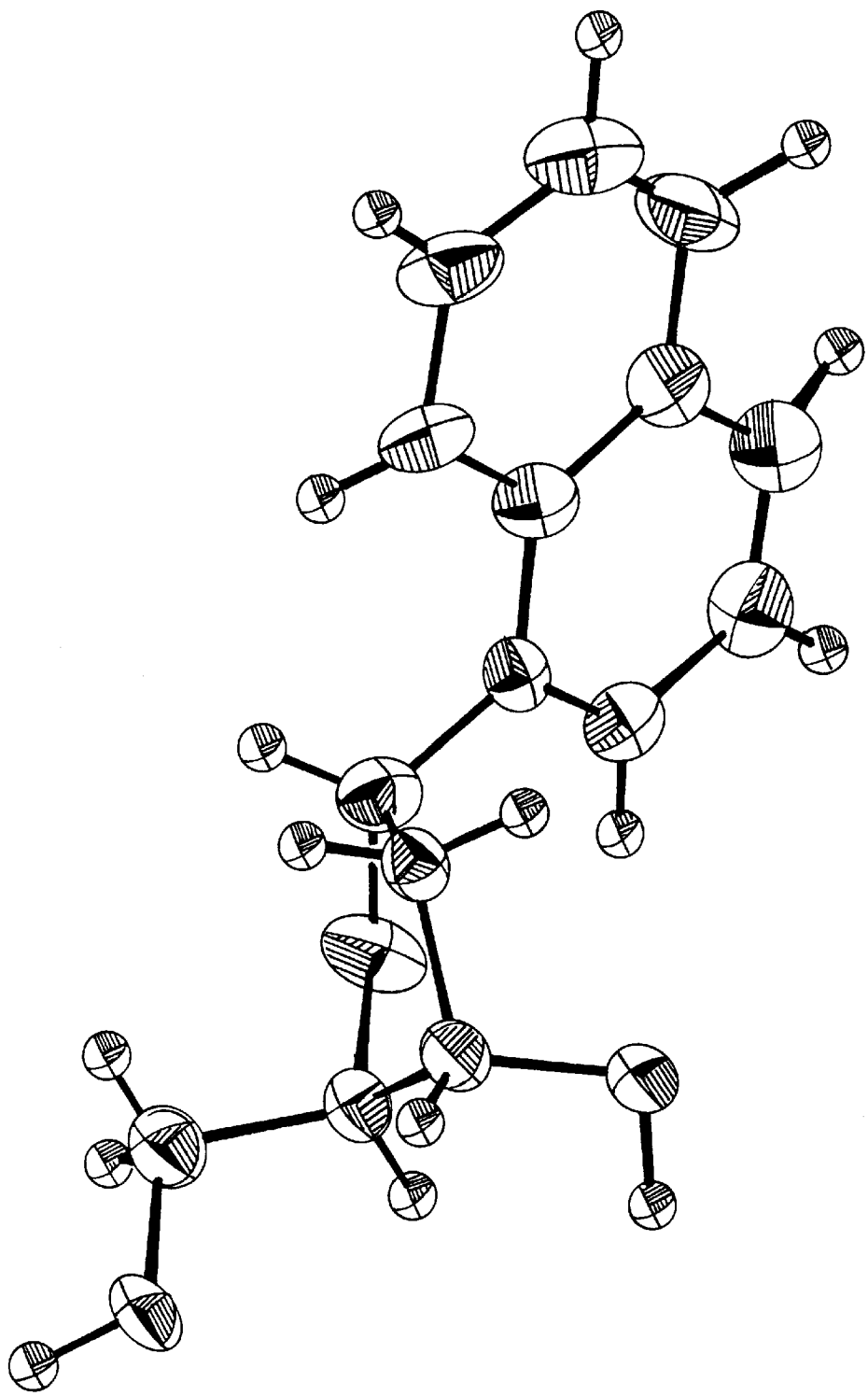
FIG. 2 is an ORTEP drawing of 1-naphthyl nucleoside 3a from single-crystal x-ray structure. The structure has the α-anomeric configuration and a C-3'-exo S-type sugar conformation.

The structural assignment of anomeric configuration for compounds 1–6 and 1a–6a (FIG. 5) was made by $^1$H-NOE studies of all compounds, by examination of coupling constants for H1' and H2' protons, and by correlation with an x-ray crystal structure of the alpha-1-naphthyl nucleoside 3a (FIG. 2). In addition, the compounds were characterized by their $^1$H and $^{13}$CNMR spectra and by high-resolution mass spectrometry.

$^1$H $^{13}$C, and 31P NMR spectra were recorded with a 300 MHZ spectrometer unless otherwise noted, and chemical shifts are given in δ(ppm) using solvent as internal reference, and the coupling constants are in Hertz (Hz). NOE difference spectral were also performed on a 300 MHZ instrument. The mass spectra were performed using electron impact or chemical ionization. All reactions were monitored by thin-layer chromatography (TLC) using EM Reagents plates with fluorescence indicator (SiO$_2$-60, F-254). Flash column chromatography was conducted using EM Science Silica Gel 60 (230–400 mesh). Mass spectral analyses were performed by the University of California, Riverside Mass Spectrometry Facility, Riverside, Calif. All reactions were carried out under a nitrogen atmosphere in dry, freshly distilled solvents under anhydrous conditions unless otherwise specified. The was distilled from sodium metal/benzophenone, methylene chloride was distilled from NaH, and pyridine was distilled from BaO prior to use.

Figure 1B:
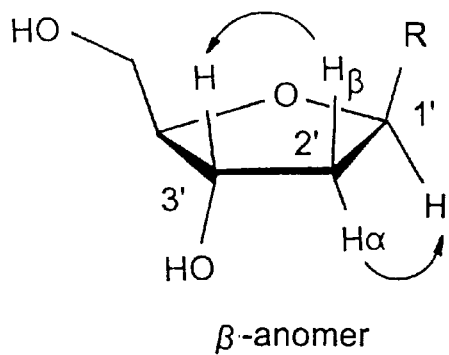

Proton nuclear Overhauser effects were used to examine the geometries of the anomeric isomers of compounds 1–6 (FIG. 5) The approach used was to separately irradiate the H-2' proton resonances situated at δ 1.7–2.7 ppm and observe enhancements at vicinal 1' and 3' protons (see FIG. 1 and Tables 1,2). Although specific assignment of which resonance corresponds to 2'-α and which to 2'-β could not be made a priori, analysis of predicted NOE effects makes possible a simple approach to assignment of stereochemistry at the 1' position. Examination of the structures of alpha- and beta- nucleosides (FIG. 1) shows that for alpha anomers, the 2'-β proton is in close proximity to both the 1' and 3' protons, while the C-2'-α proton is not near either one of these protons. In beta-anomers, on the other hand, the 2'-β proton is near only the 3' proton, while the 2'-α proton is only near the 1' proton. Thus, in an alpha anomer, separate irradiation of each of the C-2' protons should lead to two and zero NOE enhancements at the vicinal protons, while in a beta anomer, these two irradiations would lead to one significant enhancement for each irradiation.

To test this prediction, experiments on naphthyl nucleoside isomers 3 and 3a (Tables 1 and 2) were carried out. The diester of 3a is the principal product of the glycosidic coupling reaction (with the diester of 3 being a minor product). Irradiation of one of the 2' protons of the nucleoside gave significant nuclear Overhauser enhancements of 8% and 7% at the 1' and 3' protons; however, irradiation of the other 2' proton gave no significant enhancement at either 1' or 3' positions. Using the analysis above, this indicates that this compound is an alpha anomer. This assignment was confirmed by a single-crystal x-ray structure obtained for the compound (below). To complete the analysis of the two isomers we carried out the same experiments on the isomeric nucleoside 3, which is the major product after epimerization of 3a. Irradiation of one of the 2' protons gave an 8% enhancement of the 1' proton (and none at the 3' proton), while irradiation of the other 2' proton gave a 5% enhancement of the 3' proton (and none for the 1' proton). Thus, this compound is assigned to the beta configuration. Also consistent with this assignment is a separate experiment in which the 1' proton was irradiated; here we observed 6% enhancement at the 4' proton (Table 1), while the alpha isomer shows no such enhancement (data not shown).

The NOE experiments were then carried out for the isomers of 1, 3, and 4–6 (FIG. 5). The results are shown in Tables 1 and 2. The results were all consistent with the model, in that one isomer of each pair gave two and -zero enhancements of the vicinal protons for the two H-2' irradiations, while the other clearly gave one significant enhancement for each of the two irradiations. The isomers which gave two and zero enhancements were assigned as alpha-anomers, and those with one and one enhancements were assigned to be beta-anomers. Also consistent with these assignments were NOE enhancements in the H-4' positions on irradiation of the H-1' protons for the beta isomers (Table 1) which were absent in the alpha isomers.

These assignments were also internally consistent in that the major isomers obtained from the glycosidic coupling reaction were all of the same anomeric configuration (alpha). Similarly, the major isomers isolated from the epimerization were all of the same anomeric configuration (beta). In addition, all the isomers assigned as alpha had H-1' resonances which qualitatively appeared as pseudo-triplets (they are actually doublets of doublets), having both coupling constants near 6.0–8.0 Hz. The isomers assigned to the beta configuration had H-1' resonances which appeared as nearly evenly spaced doublets of doublets (J~3 and 10 Hz). These H-1'–H-2' coupling constant trends are consistent with a literature report of similar coupling constants for related β-C-nucleoside[18] (although they are reversed relative to observations for β-N-nucleosides).

Also useful in confirmation of these structural assignments was x-ray structural data obtained for 1-naphthyl compound 3a (FIG. 2). A crystal suitable for analysis was obtained by recrystallization from methylene chloride/hexane ($CH_2Cl_2$/hxane).

Measurements were made on an Enraf-Nonius diffractometer with graphite monochromated Mo-Kα radiation. Single crystals of $C_{15}H_{16}O_3$ are monoclinic, space group $P2_{1_a}$(#4), with α=7.806(2) Å, b=6.720(2) Å, and c=11.898 (3)Å, V=615.8(3)Å$^3$, Z=2 with calculated density 1.31 g/cm3. The data was collected at −20(1)° C. using the w/2T scan technique to a maximum 2T of 50.0°. Omega scans of several intense reflections, made prior to data collection, had an average width at half-height of 0.26° with a take-off angle of 2.8°. The counter temperature consisted of a variable horizontal slit with a width ranging from 2.0 to 2.5 mm and a vertical slit set to 2.0 mm. The diameter of the incident beam collimator was 0.7 mm and the crystal to detector distance was 21 cm. A total of 1234 unique absorption-corrected refections were collected, and the structure was solved by direct methods. The non-hydrogen atoms were refined anisotropically, and the hydrogen atoms were included in idealized positions. The final cycle of full-matrix least-square refinement was based on 785 observed reflections and converged (largest parameter shift was 0.01 times its esd) with unweighted and weighted agreement parameters of R=0.043 and $R_w$=0.039. The standard deviation of an observation of unit weight was 1.54. The maximum and minimum peaks on the final difference Fourier map corresponded to 0.14 and −0.15 e−/Å$^3$, respectively. All calculations were performed with the teXsan software package of the Molecular Structure Corporation.

The structure shows the α-configuration and in analogy to natural nucleosides, the naphthalene is in an anti-conformation, with the aromatic group oriented away from the sugar. The deoxyribose ring is in a C-3'-exo (S-type) conformation.

Experimental H'-1' to H-2' coupling constants for the ester of this compound (3a) in CDCI$_3$ were J=8.0 and 6.0 Hz. The corresponding dihedral angles generated from the x-ray structure are found to be 8.1° and 124.5°. Application of the Karplus relationship empirically adjusted for nucleosides[20] predicts J=9.2 and 2.8 Hz, respectively, indicating a small change in ring conformation in solution relative to that in the crystal (or non-ideal match of the empirical relationship of this C-nucleoside). Interestingly, although this compound clearly is an alpha-anomer, the experimentally measured coupling constants are more consistent with those commonly seen for beta-, rather than alpha-, anomers of natural nucleosides.

EXAMPLE 3

Incorporation into DNA

Figure 14:
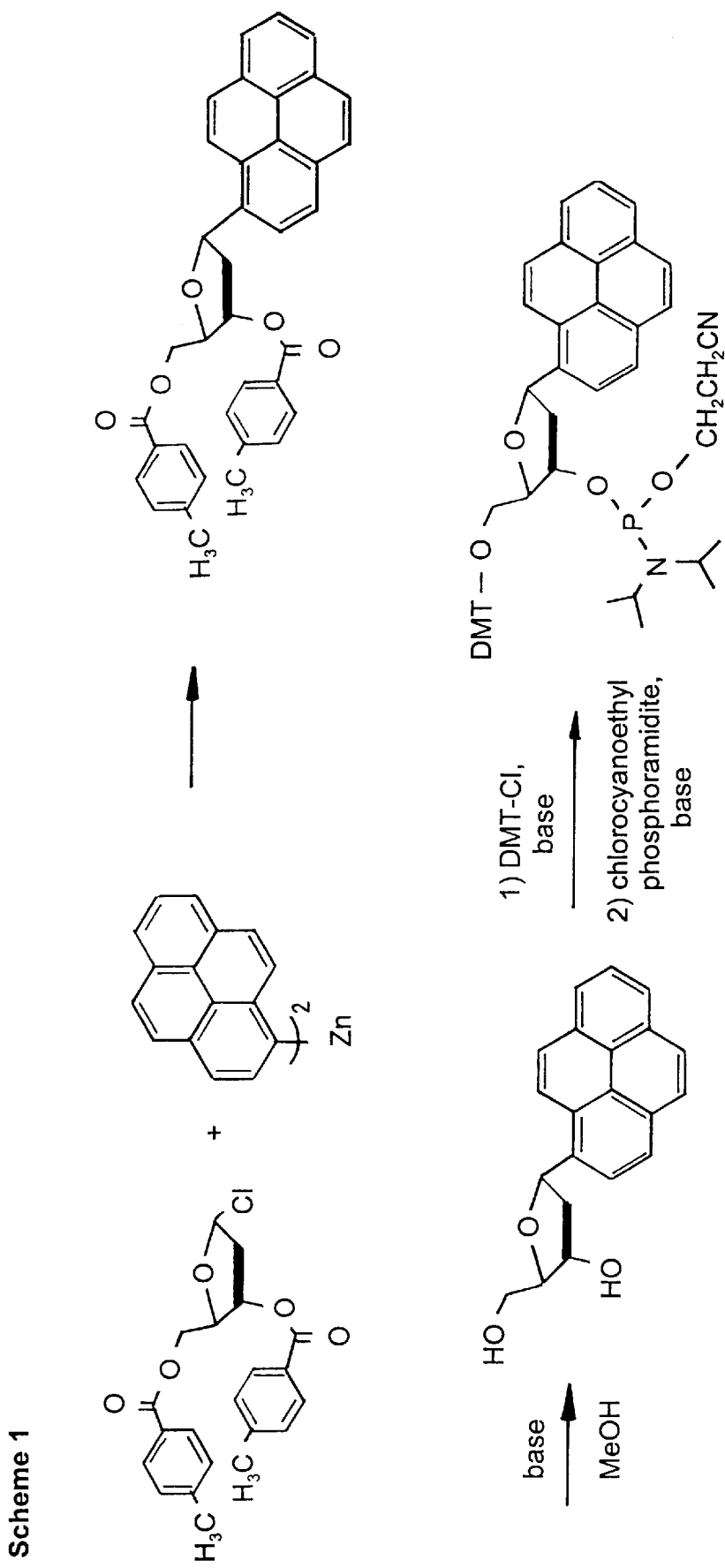
FIG. 14 is a schematic representation of a synthetic method for the preparation of the α-pyrene nucleoside of the present invention.
Figure 15:
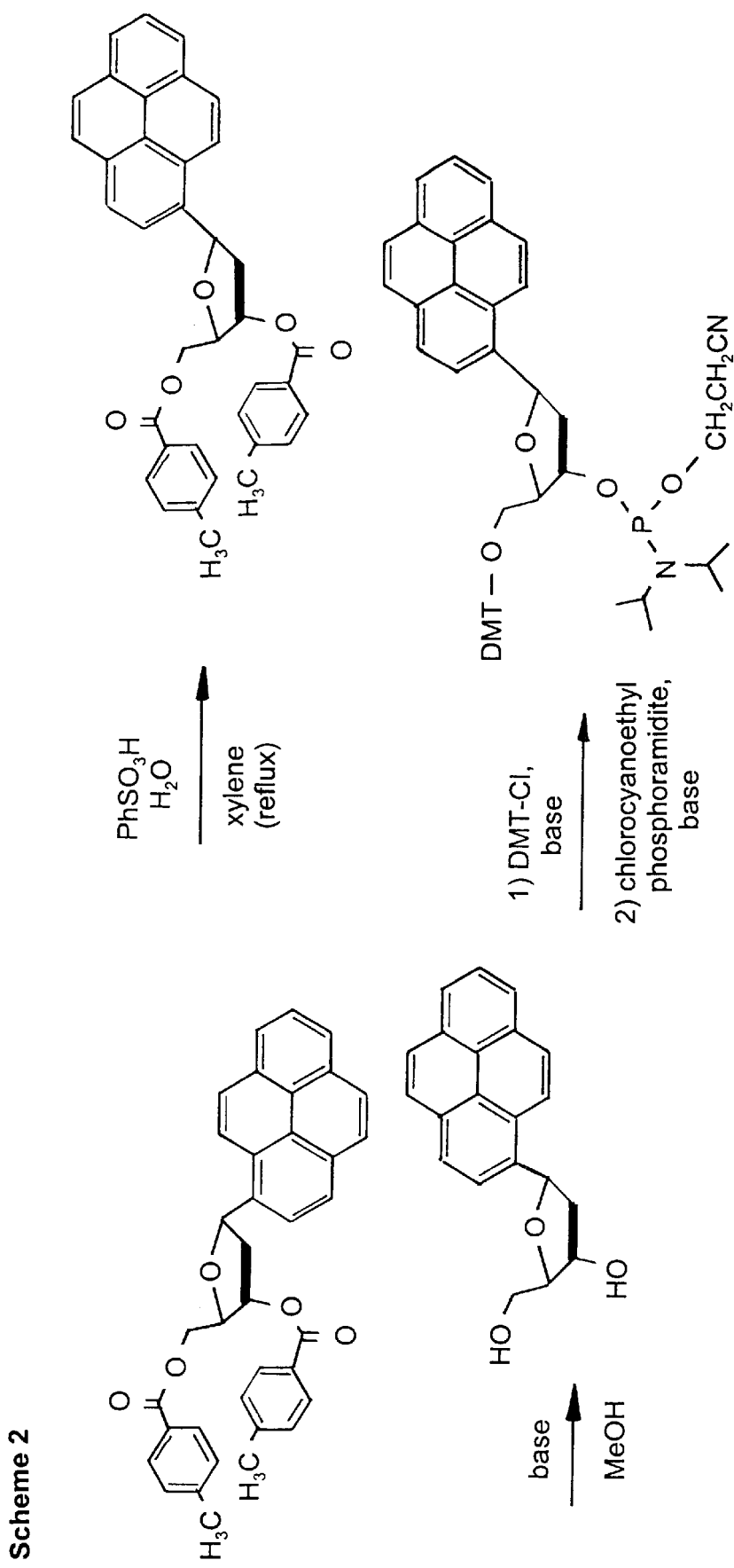
FIG. 15 is a schematic representation of a synthetic method for the preparation of the β-pyrene nucleoside of the present invention.
Figure 16A:
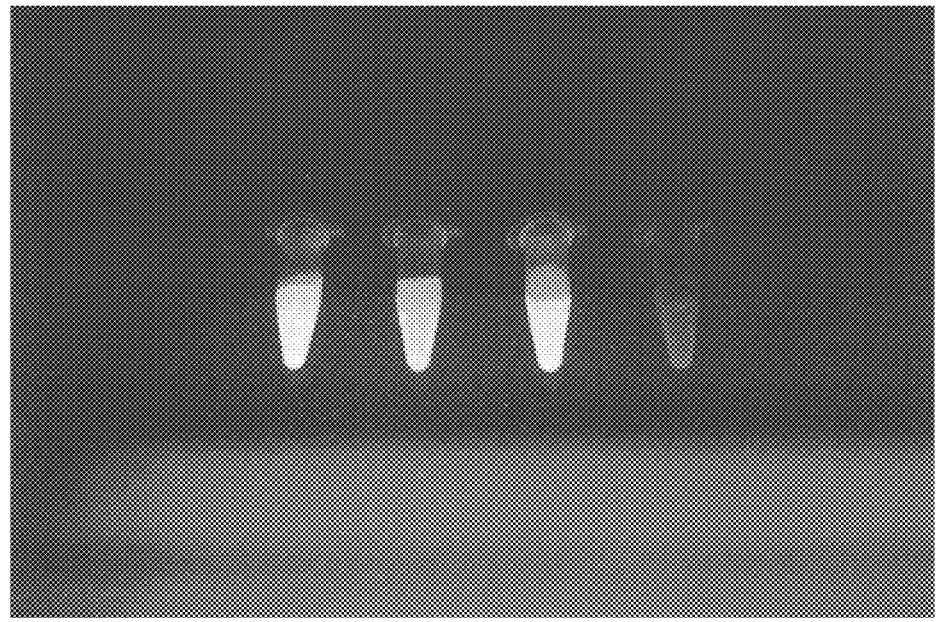
FIG. 16A is a photograph showing fluorescent DNAs in four plastic tubes held over a transilluminator. From right to left, tubes contain fluorescein-labeled oligonucleotides with 1, 2, 3, and 5 fluorescein. The intensity decreases as the number of fluorescein labels increases.
Figure 16B:
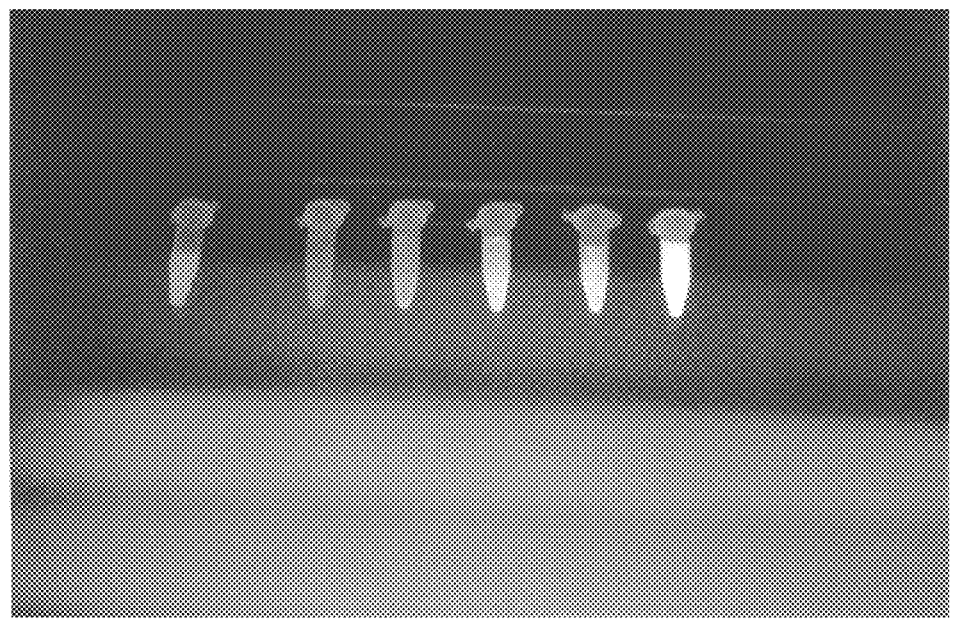
FIG. 16B is a photograph showing α-pyrene-labeled oligonucleotides (aqueous buffer with no deoxygenation) in six plastic tubes held over a transilluminator. The very left tube has one pyrene label at 10× the concentration of the other five tubes and shows the typical blue color of pyrene. The other five tubes are diluted 10-fold and have 1, 2, 3, 6, and 10 labels from left to right.

The β-C-deoxynucleosides 1, 2, and 3 (of FIG. 5) were then carried on with the aim of incorporating them into DNA oligonucleotides by automated solid-phase methods (FIG. 7 and FIGS. 14–15). Standard methods were used to convert the unprotected nucleosides to 5'-dimethoxytrityl-protected derivatives in yields ranging from 59–92% after purification. These were then converted into cyanoethyl phosphoramidite derivatives, which were obtained in 50–89% yields after purification by column chromatography.

DNA oligonucleotides were synthesized on an Applied Biosystems 392 synthesizer using standard β-cyanoethylphosphoramidite chemistry but with extended (10 Minute) coupling cycles for the normal residues. Stepwise coupling yields for the nonnatural residues were all greater than 90% as determined by trityl cation monitoring. Oligomers were purified by preparative 20% denaturing polyacrylamide gel electrophoresis and isolated by the crush and soak method, and were quantitated by absorbance at 260 nm. Molar extinction coefficients were calculated by the nearest neighbor method. Values for olignucleotides containing nonnatural residues were estimated the following way: each of the new nucleotides was measured for its excition coefficient at 260 nm. The molar extinction coefficients for 2 and 3 were found to be 8990, and 154, respectively, and these values were added to the value for the core sequence dCGCGCG.

Figure 3A:
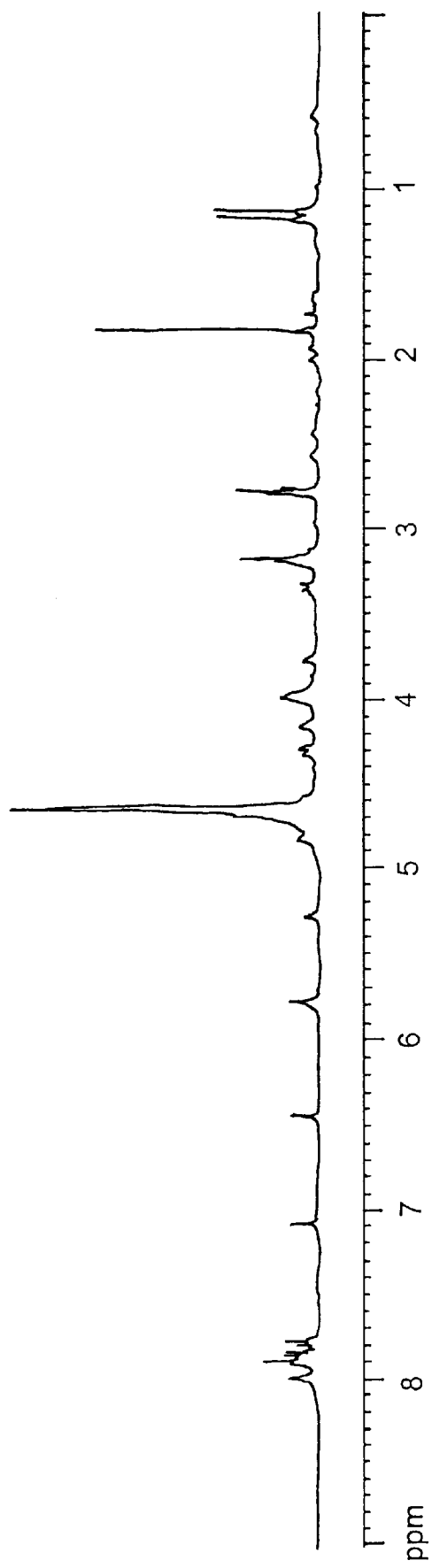
FIG. 3 shows 400 MHz proton NMR spectra for trinucleotides (sequence T-X-T) containing (a) pyrenyl, (b) phenanthryl, and (c) naphthyl nucleosides 1–3 at the X position.
Figure 3C:
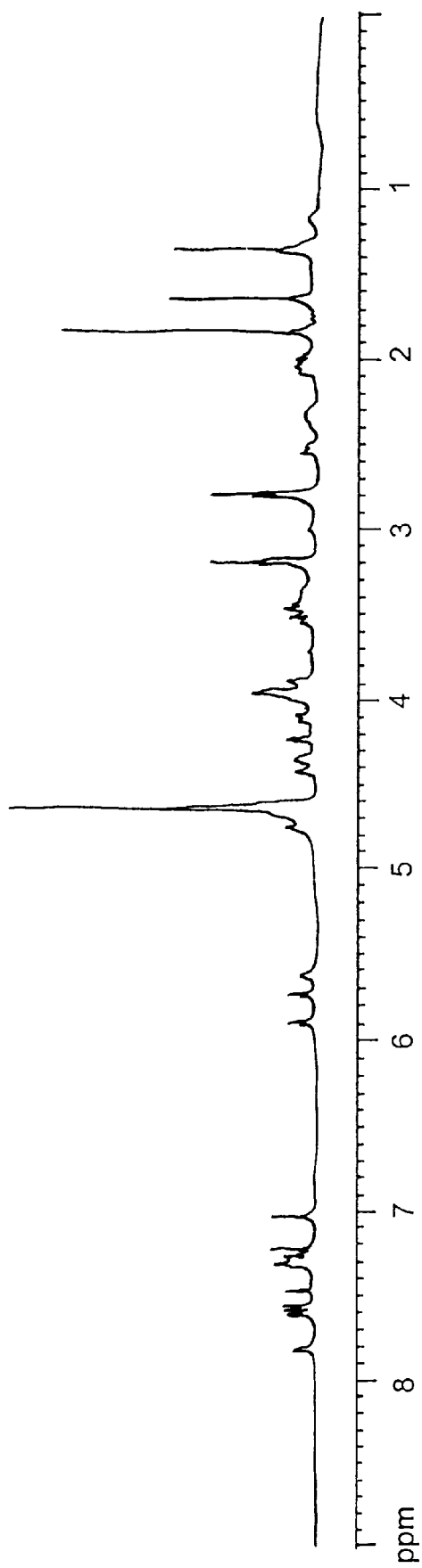

The absorbance of nucleoside 1 in DNA was measured at 350 nm and 0.48 of this value was subtracted from the total absorbance at 260 nm to get the absorbance of the core DNA alone. oligodeoxynucleotides were obtained after purification as the sodium salt. Intact incorporation of residues 1–3 was confirmed by synthesis of short oligomers of sequence T-X-T (where X=1–3). Proton NMR (400 MHz) (FIG. 3) indicated the presence of the intact structures with the expected integration.

The spectra of the crude unpurified oligonucleotides show clear resonances very similar to those of the free nucleosides, and having the expected aromatic integrations relative to anomeric C-1' protons and thymine C-6 protons and C-5 methyl groups. This confirms both the presence of the intact structures (as expected for unreactive aromatic hydrocarbons) as well as the high coupling yields, since di- and mononucleotides which result from incomplete coupling are not seen.

EXAMPLE 4

Fluorescence Properties in DNA

Since polycyclic aromatics such those in the nucleosides 1, 2, and 3 (FIG. 5) have been studied in other contexts as fluorescent probes,[22] the fluorescence properties of oligonucleotides containing these structures in aqueous buffer was examined. Heptamer oligodeoxynucleotides having the sequence 5'-dXCGCGCG, (where X-1, 2 and 3) which are self-complementary and form duplexes with the polycyclic aromatic nucleoside situated at the 5' ends were synthesized. These were purified by preparative denaturing gel electrophoresis.

Fluorescence spectra were recorded on a SPEX-Fluorolog-2 series fluorometer. A xenon lamp was used as the source of radiation. The fluorescence measurements were taken in the right angle mode using 0.1–0.15 µM DNA solutions in a pH 7.0 buffer (10 mM Na-PIPES, 10 mM $MgCl_2$, 100 mM NaCl). Five scans were averaged at 23° C. The excitation slits were set to 6 mm and the emission slits to 2 mm. All emission spectra were corrected using a reference dye (rhodamine-B) to compensate for instrument fluctuations, and also by subtraction of data for buffer alone. Excitation wavelengths of 233, 251 and 341 nm (the absorbance maxima) were used to excite the compounds containing naphthalene, phenanthrene and pyrene, respectively.

Figure 4A:
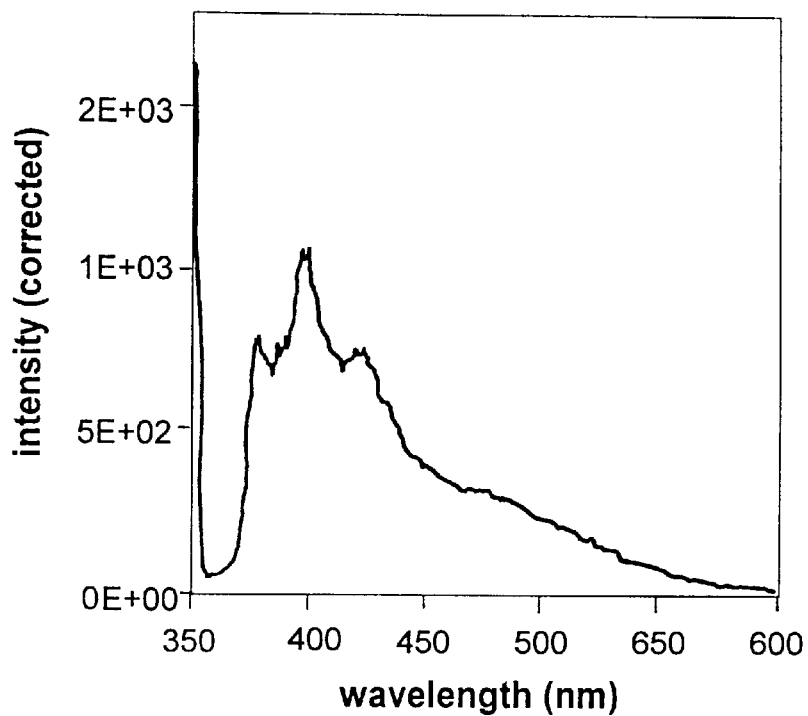
FIG. 4A is a fluorescence emission spectrum for self-complementary heptamer oligonucleotides containing pyrene as the C-nucleosides at the 5'-terminal position. The DNA sequence is 5'XCGCGCG, where X is 1. Excitation is at 341 nm and solutions contain pH 7.0 PIPES (10 mM), 100 mM NaCl, 10 mM $MgCl_2$ and DNA strand concentrations of 0.1 and 0.15 $\mu$M.
Figure 4B:
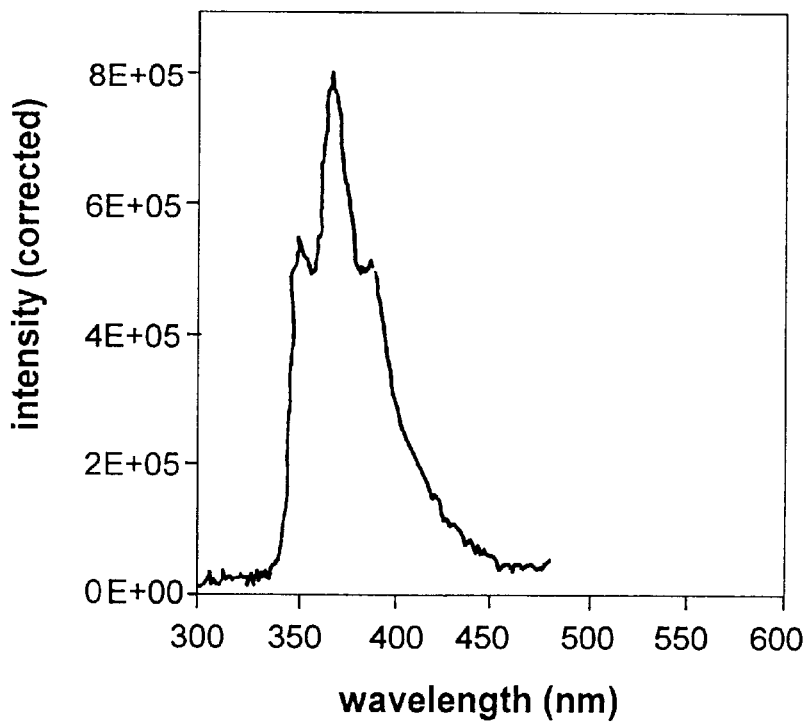
FIG. 4B is a fluorescence emission spectrum for self-complementary heptamer oligonucleotides containing phenanthrene as the C-nucleosides at the 5'-terminal position. The DNA sequence is 5'XCGCGCG, where X is 2. Excitation is at 251 nm. Solutions and DNA strand composition are the same as for FIG. 4A.
Figure 5A:
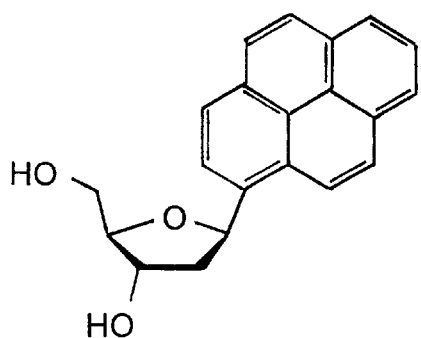
FIGS. 5A through 5F depict the structural formulas of the compounds of the present invention. Compounds 1–6 as shown are the β forms. Compounds 1a through 6a are the α forms of the molecules depicted in the FIGS. 5A through 5F.
Figure 5B:
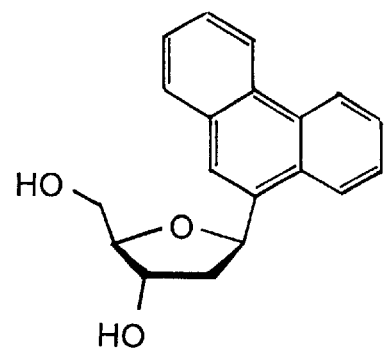
Figure 5C:
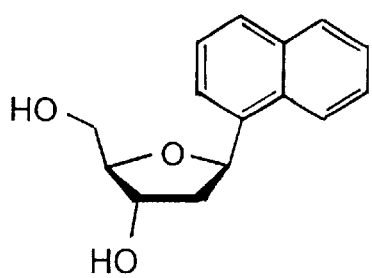
Figure 5D:
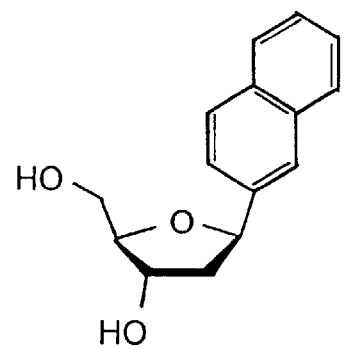
Figure 5E:
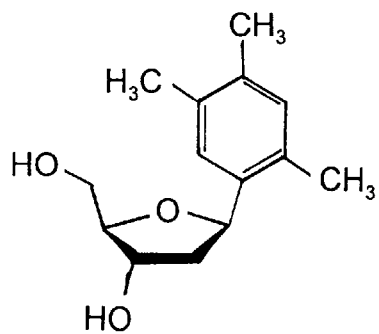
Figure 5F:
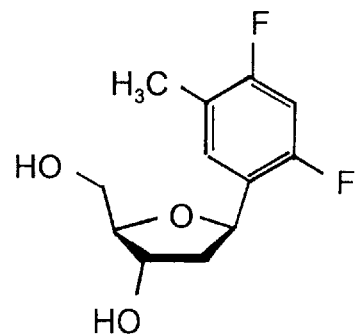

Emission spectra were measured for the three sequences in a pH 7.0 buffer (10 mM PIPES buffer, 100 mM NaCl, 10 mM $MgCl_2$) at 25° C., conditions under which they likely form duplexes. The naphthalene-containing sequence showed no emission detectable above background. The other compounds showed fluorescence emission profiles consistent with published spectra for the polycyclic aromatic parent structures.[22] The phenanthrene-containing oligonucleotide had the most intense emission (FIG. 4), with the strongest peak at 370 nm. The pyrene-modified sequence showed a similar emission profile but with an emission maximum at 395 nm and with peak intensity considerably lower than that for the phenanthrene case, suggesting considerable quenching by the DNA under these conditions and in this sequence.

EXAMPLE 5

Properties of the α-pyrene Nucleoside in DNA

The α-pyrene nucleoside phosphoramidite was incorporated into DNA on an ABI 392 synthesizer on 1-µmole scale. Coupling yields were monitored by trityl response and were high (~92% or greater). Several olignucleotides (FIG. 13) were prepared which were designed to form triplexes with a single-stranded target by folding back. The molecules have five-nucleotide loops composed either of thymine nucleotides or with varying numbers (1, 3, 5) of pyrene nucleotides. These were synthesized without complication and purified by denaturing preparative PAGE gels.

Thermal denaturation experiments were performed as described previously, using a heating rate of 0.5° C./min. Solutions for the thermal denaturation studies contained a 1:1 molar ratio of oligonucleotide probe and its corresponding complementary 18-nt oligomer (1.5 µM each). Solutions were buffered with 10 mM Na.PIPES (1,4-piperazine-bis (ethanesulfonate), Sigma) at pH 7.0. Also present in the denaturation solutions were 100 mM NaCl and 10 mM $MgCl_2$. After the solutions were prepared they were heated to 90° C. and allowed to cool slowly to room temperature prior to the melting experiments. Uncertainty in $T_m$ is estimated at ±0.5° C. based on repetitions of experiments.

The results of binding studies (thermal denaturation) showed that all oligomers bound the single-stranded target well; thus, the new nucleoside does not interfere with binding properties. Separate binding studies were also carried out using longer targets which extend beyond the loop; binding was still tight, and interestingly, the pyrene-tagged compounds showed stronger binding the more pyrenes were present. For example, a complex with the P1 oligomer had a $T_m$ of 35° C. at pH 7.0, while the P3 probe bound with a $T_m$ of 42° C., or 7° C. higher. Binding to the sequence shown above was also demonstrated by native gel shift experiments, and the complexes were clearly visible under fluorescent light. While the single-pyrene version was deep blue in color, the multi-tagged ones were light blue to white in appearance, indicative of longer-wavelength emission. See FIG. 13 for description of P oligonucleotides.

Fluorescence Properties

Steady-state fluorescence spectra were recorded on a SPEX-Fluorolog-2 series fluorometer at room temperature. The source of ratiation was a xenon arc lamp. An excitation wavelength of 341 nm was used, and all excitation and emission slits were set to 2 mm. Fluorescence measurements were taken in the right angle mode. All sample concentrations were 0.1 µM in labeled DNA in a pH 7.0 buffer (10 mM Na.PIPES, 10 mM $MgCl_2$, 100 mM NaCl). The buffer solutions were air-saturated. For the duplex measurements, an equimolar amount of the Watson-Crick complement was added, the mixture heated to 90° C. and slow cooled before remeasuring the fluorescence. All emission spectra were measured using a reference dye (rhodamine-B) to compensate for lamp fluctuations and were corrected by subtraction of data for buffer alone unless indicated otherwise. 1-Pyrenemethylamine hydrochloride was obtained from Alrich.

Figure 9:
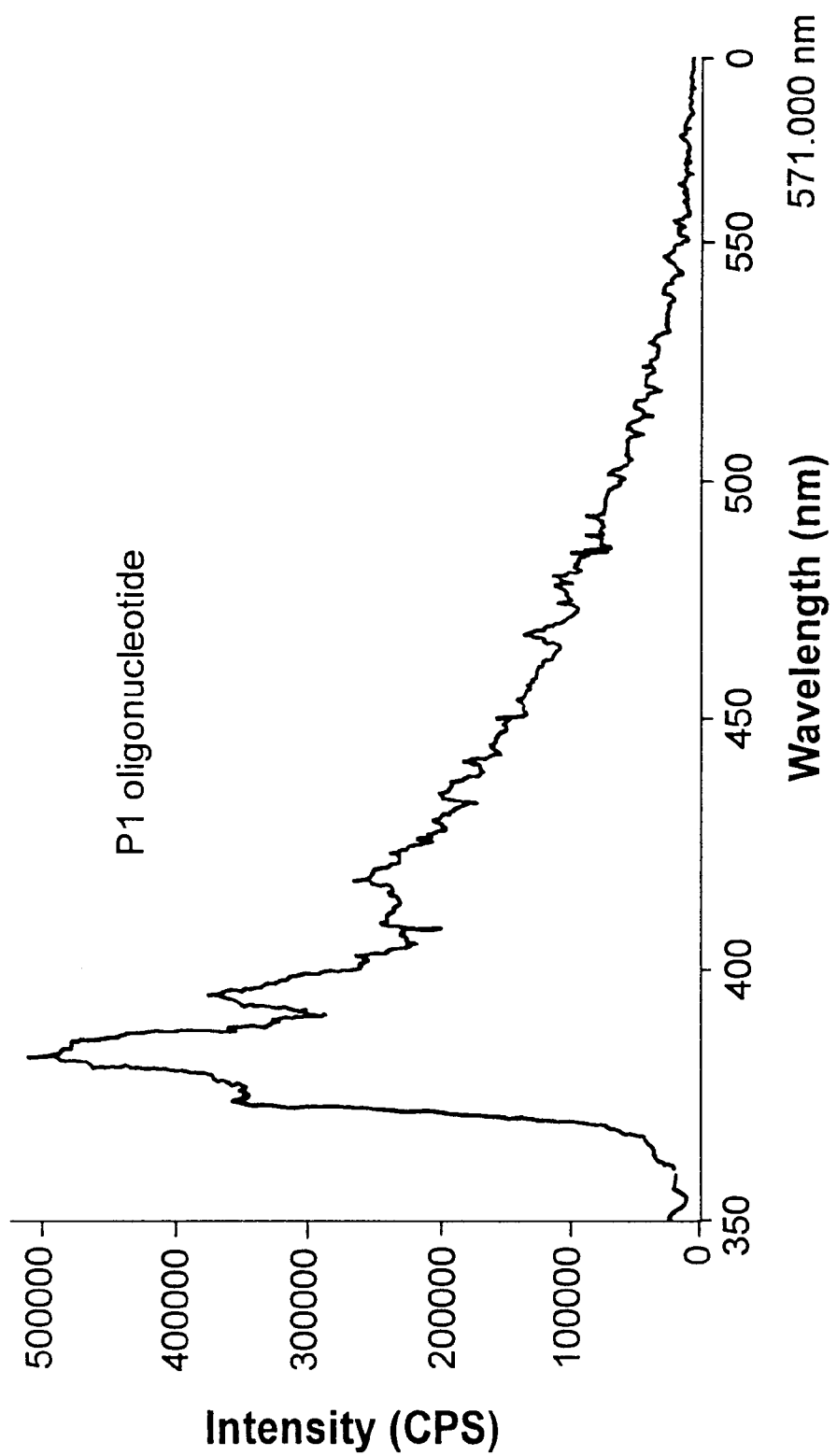
FIG. 9 is the emission spectrum of the oligonucleotide designated P1 in FIG. 13.
Figure 10:
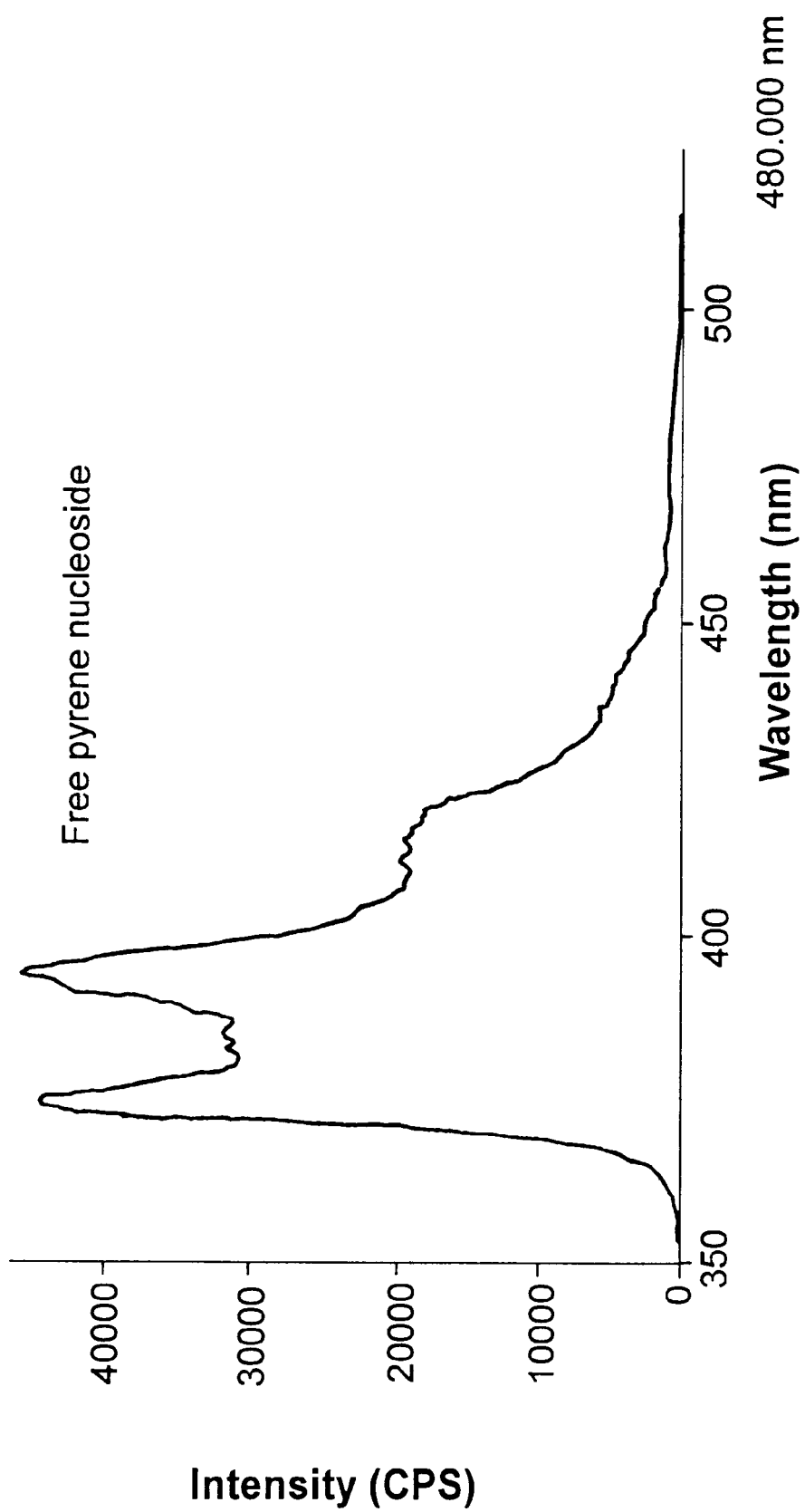
FIG. 10 is the emission spectrum of the free pyrene nucleoside designated P0 in FIG. 13.
Figure 11:
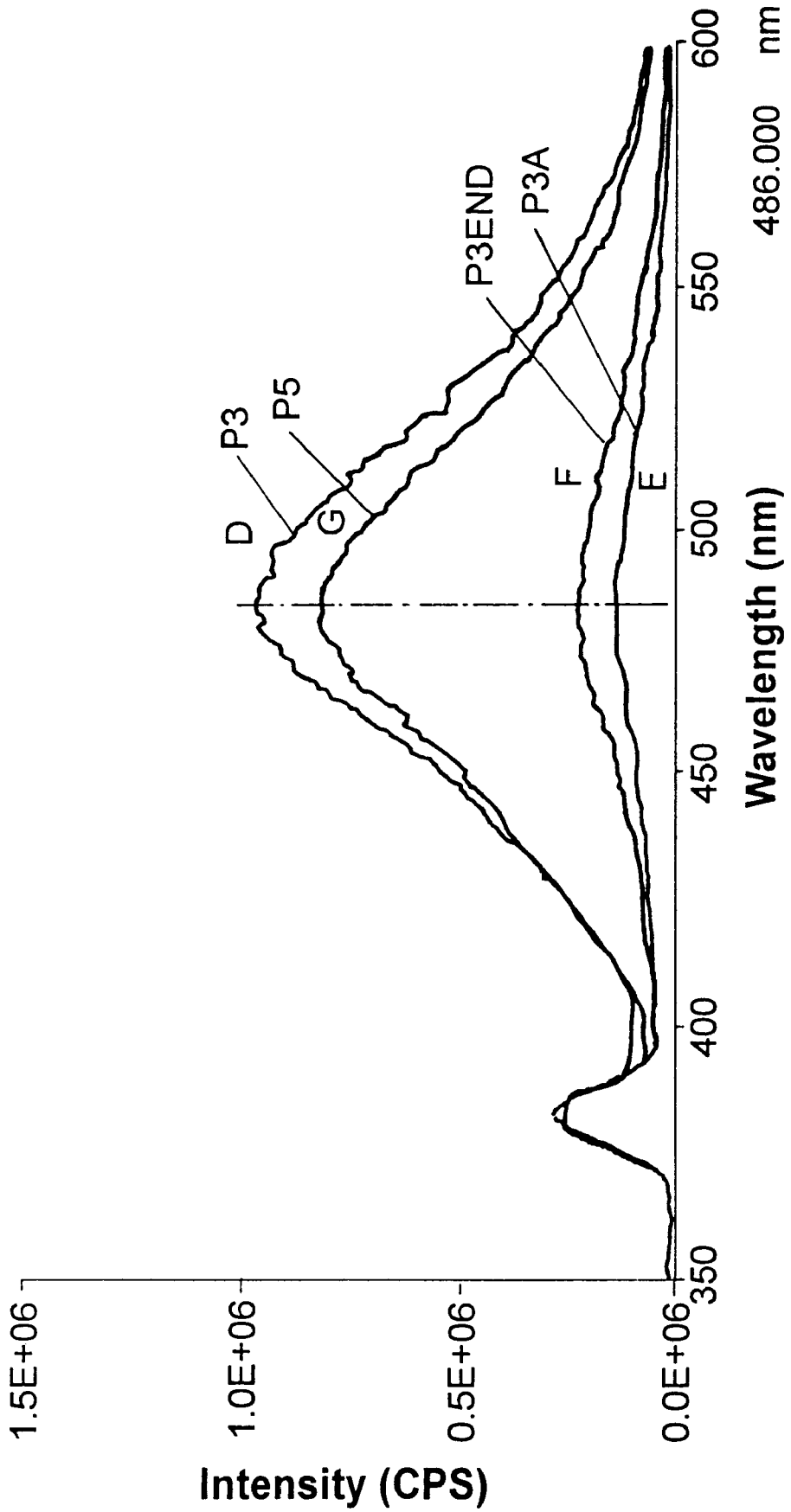
FIG. 11 is the emission spectra of oligonucleotides designated P3, P5, P3END and P3A in FIG. 13.

The singly-tagged oligonucleotide (P1) of FIG. 13 was studied first. The spectrum of oligonucleotide P1 was compared to that of the free nucleoside by itself in water at the same concentration (0.1 µM). The compounds were excited at 341 nm and studied in a pH 7.0 buffer (100 mM NaCl, 10 mM MgCl$_2$, 10 mM Na-PIPES). The spectra are shown in FIGS. 9 and 10.

The free nucleoside shows an emission spectrum very similar to that published for pyrene, with the most intense peak at about 400 nm. The P1 oligonucleotide at the same concentration shows an emission spectrum with less structure and with a tail out to longer wavelengths. Interestingly, the emission intensity of P1 compound is 500,000 at 381 nm, while that of the free nucleoside in water is 50,000. Thus, incorporation of the nucleoside into a DNA strand leads to an increase in emission intensity of about 10 fold.

The multi-tagged oligonucleotides have two unusual characteristics when examined by fluorescence spectroscopy. First, the emission spectra show a clear excimer band at about 450–550 nm (peak at 483 nm). Second, the intensity of the excimer band is more intense than the normal pyrene fluorescence of P1 for the two compounds with three and five labels. Interestingly, when three labels were placed with thymines between (comparing P3 and P3A), the excimer band is much weaker, confirming that excimer requires adjacent placement of the labels. Three pyrenes in a loop gave a stronger excimer band than did three at the end (compare P3 to P3END), indicating greater stacking in the loop (FIG. 13).

All five fluorescent-tagged oligomers were then hybridized to the complementary target DNA. Importantly, the fluorescent emission intensity stayed the same (within 20%) on binding. This compares very favorably to pyrenebutyrate linked to DNA, which is quenched by about 10 fold on binding a complement[30b].

The P3 oligonucleotide was dimerized to circular form following the procedure of Rubin et al. 1995 *Nucleic Acids Res.* 23:3547–3553. This oligonucleotide binds quite tightly and specifically to a 20-nt recognition site in DNA. The emission intensities of the P3 oligomer (containing 3 pyrene nucleosides) were compared to that of the circular P6 oligomer (containing 6 pyrene nucleosides) under identical conditions (See FIG. 13).

Figure 12:
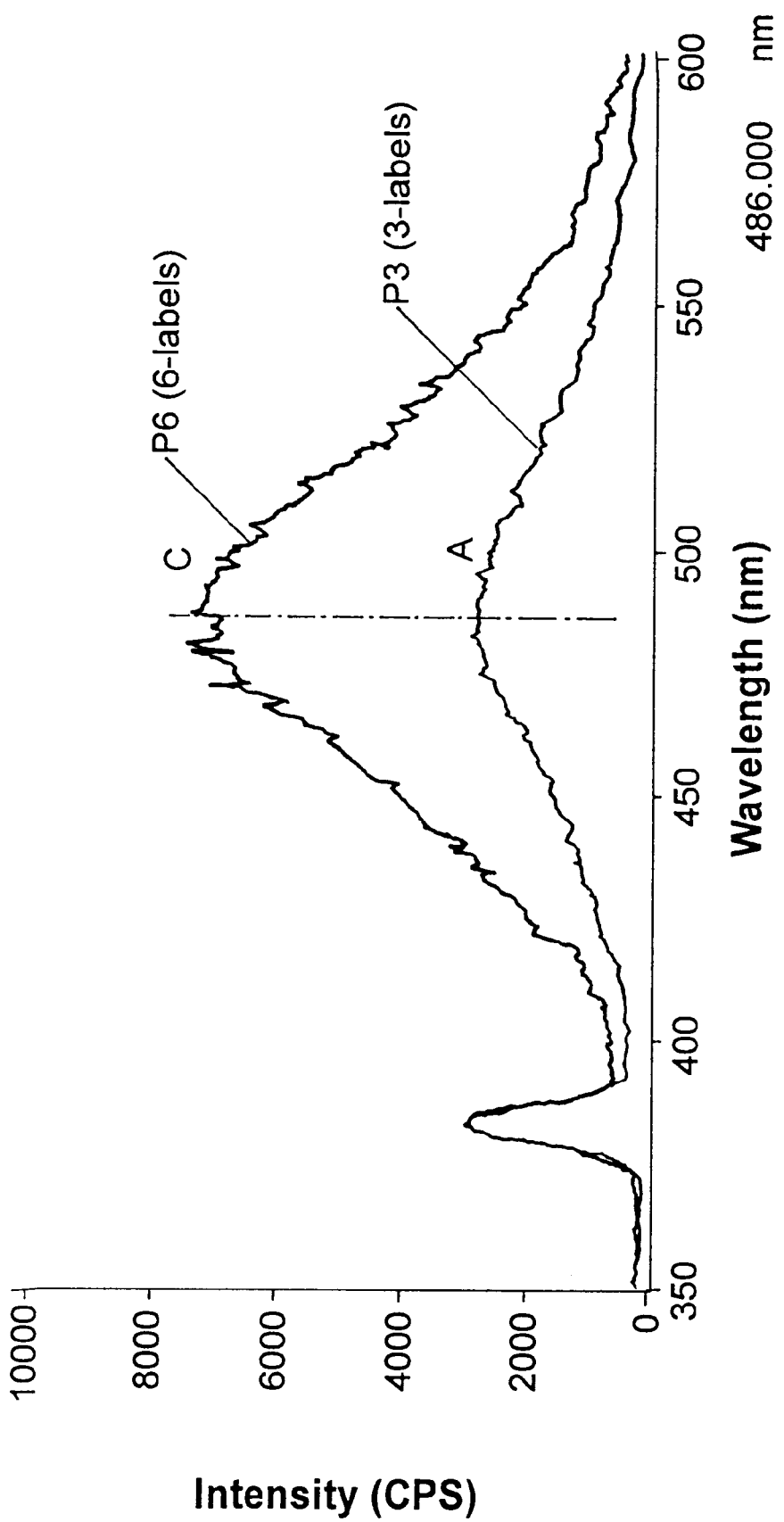
FIG. 12 is the emission spectra of oligonucleotides designated P3 and P6 in FIG. 13.

Results show that the P6 compound has an emission intensity twice that if the P3 oligonucleotide (see FIG. 12). Thus, six pyrene labels are present in this DNA probe with no quenching of fluorescence intensity. The emission intensity of this P6 circle at 483 nm is about four times that of the singly-labeled Pi compound (emission maximum 381 nm), and about forty times than that of the free-pyrene nucleoside in the same buffer.

These reults show that multiple labels can be incorporated into DNA, yielding emission which can be considerably brighter than a single label. In addition, the emission is at longer wavelengths which are more easily visible.

EXAMPLE 6

Substitution in Linear Oligonucleotide Probes

Experiments were performed to optimize multiple alpha-pyrene substitution at the ends of standard DNA probes rather than substitution in loop regions of triplex-forming probes as in Example 5. First evaluated was whether 5'-end or 3'-end substitution was favored, and whether the neighboring base mattered. Experiments were carried out with oligos containing 3 adjacent alpha-pyrenes; these were observed for the florescence emission intensity both unbound and when hybridized. The probes are designed to bind to human telomere repeats. Results are shown below for unbound oligomers (the relative results do not change when they are bound).

| sequence | rel intensity(485 nm) |
|---|---|
| 5'-CCC TAA CCC TAA CCC TAA PPP-3' SEQ ID NO:2 | $1.0 \times 10^7$ |
| 5'-PPP CCC TAA CCC TAA CCC TAA-3' SEQ ID NO:3 | $4.4 \times 10^6$ |
| 5'-PPP AAC CCT AAC CCT AAC CCT-3' SEQ ID NO:4 | $1.0 \times 10^7$ |

Results show that 5' end and 3' end substitution give identical fluorescence intensity. The nature of the adjacent base, however, does make a difference. Comparison of the cases when the adjacent base is A or C shows that the case with A adjacent to a pyrene gave significantly (50% higher) emission intensity.

Next, how best to add additional pyrenes for greater intensity was examined. Results with pyrenes substituted internally in DNA (Example 5) indicated that emission intensity for the excimer increases with three to five adjacent pyrenes, but adding another (six adjacent labels) actually decreases overall intensity. A similar effect is seen with pyrenes incorporated at the end of a linear probe.

Three oligos having multiple pyrenes were compared: one with three adjacent labels (P3), one with six adjacent labels (P6), and one with three labels, then an adenine, then another three labels (P3A3). Of these, P3A3 gave much better intensity than the other two. Thus, yet brighter labels may be possible by using configurations such as P3AP3AP3, or P5APS, or adding such groups at both ends of the probe.

| sequence | rel intensity(485 nm) |
|---|---|
| 5'-CCC TAA CCC TAA CCC TAA PPP-3' SEQ ID NO:5 | $3.8 \times 10^6$ |
| 5'-CCC TAA CCC TAA CCC TAA PPP A PPP-3' SEQ ID NO:6 | $7.2 \times 10^6$ |
| 5'-CCC TAA CCC TAA CCC TAA PPPPPP-3' | $1.1 \times 10^6$ |

EXAMPLE 7

Comparison of Excimer Fluorescence Properties of the Two Isomers

Figure 17:
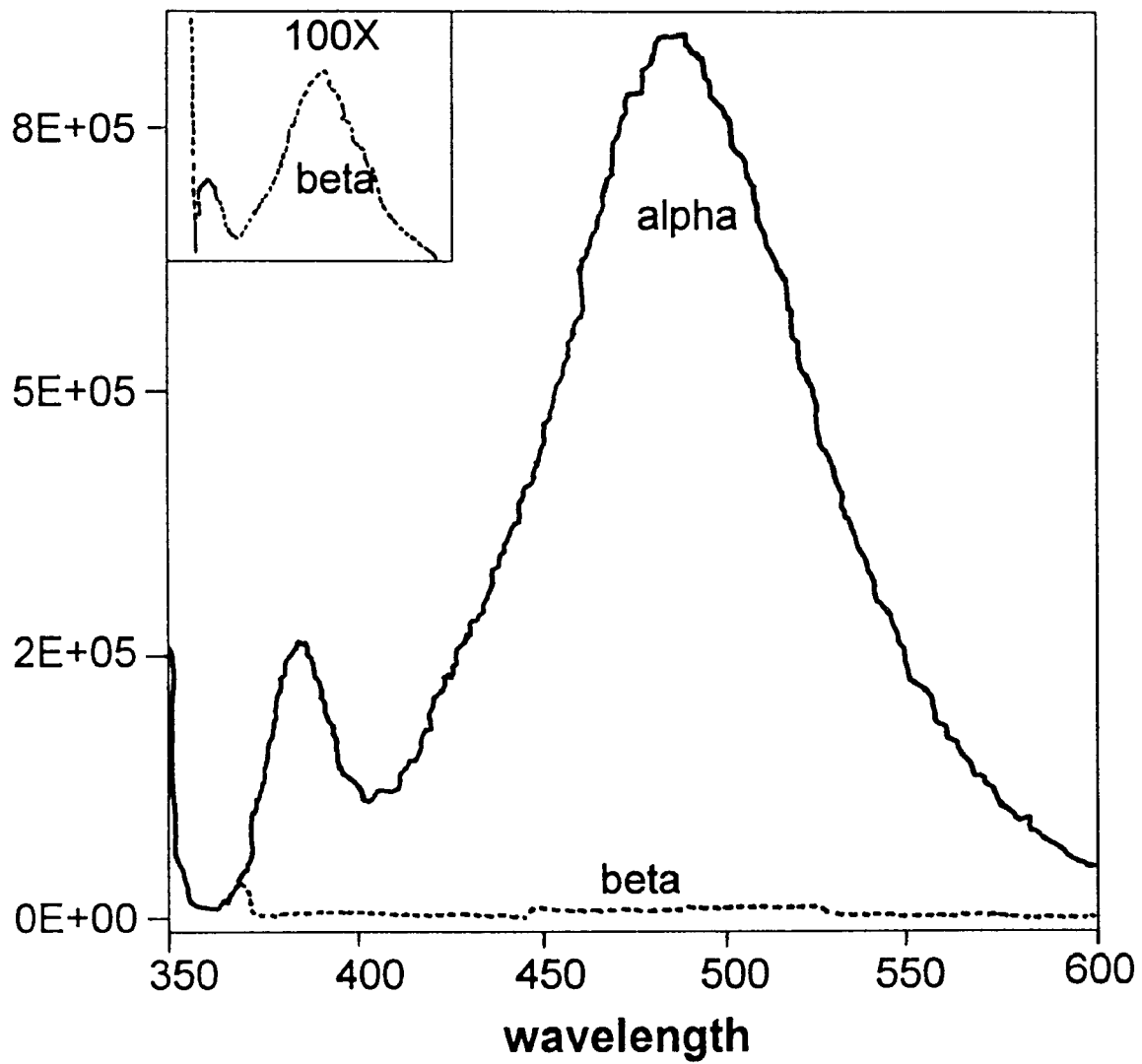
FIG. 17 is a fluorescence emission spectra for oligonucleotides having either three consecutive alpha pyrene residues or three consecutive beta pyrene residues.

The same DNA sequence described in Example 5 was synthesized with three consecutive pyrene residues; one sequence had three alpha isomers, and the other, three beta isomers. Fluorescence emission was measured for both with the same excitation and same solution conditions. Results show that both oligonucleotides show virtually the same emission bands consistent with full excimer formation with loss of pyrene fluorescence. The peak height for the alpha case however, is ~100 times higher than for the beta case (see FIG. 17.)

There is likely to be very little inherent fluorescence difference for the two chromophores alone. The likely reason for the large difference in DNA is that the beta case (which has the same configuration as natural DNA bases) stacks more strongly with neighboring DNA, and that this stacking leads to stronger quenching by neighboring bases.

EXAMPLE 8

Further studies were performed on the following oligonucleotides:

electrophoresis and isolated by the crush and soak method. Molar extinction coefficients of unmodified oligonucleotides were calculated by the nearest neighbor method.[33] Concentrations of oligonucleotides containing pyrene residues were determined in the following way: UV absorbances were measured at 260 nm and 350 nm. The 260 nm values were substituted into Beer's Law, using the calculated extinction coefficient for the DNA portion of the oligonucleotide. A correction factor for pyrene's contribution at 260 nm was taken to be 0.5 times the absorbance at 350 nm. This gave an approximate concentration of the labeled oligomer. To reach a more accurate oligomer concentration, Job's plots were constructed from mixing experiment data carried out with the Watson-Crick complement to the oligonucleotides.

Thermal denaturation experiments. Solutions for the thermal denaturation studies contained a 1:1 molar ratio of oligonucleotide probe and its corresponding complementary 18-nt oligomer (1.5 $\mu$M each). Solutions were buffered with 10 mM Na.PIPES (1,4-piperazine-bis(ethanesulfonate), Sigma) at pH 7.0. Also present in the denaturation solutions were 100 mM NaCl and 10 mM $MgCl_2$. After the solutions were prepared they were heated to 90° C. and allowed to cool slowly to room temperature prior to the melting experiments. The melting studies were carried out as described previously,[14] using a heating rate of 0.5° C./min. Uncertainty in $T_m$ is estimated at ±0.5° C. based on repetitions of experiments.

| Name | # Pyrenes | Sequence |
|---|---|---|
| HT0 | 0 | 5'-CCC TAA CCC TAA CCC TAA SEQ ID NO:7 |
| HT1 | 1 | 5'-CCC TAA CCC TAA CCC TAA P SEQ ID NO:8 |
| HT2 | 2 | 5'-CCC TAA CCC TAA CCC TAA PP SEQ ID NO:9 |
| HT3 | 3 | 5'-CCC TAA CCC TAA CCC TAA PPP SEQ ID NO:10 |
| HT4 | 4 | 5'-CCC TAA CCC TAA CCC TAA PPPP SEQ ID NO:11 |
| HT5 | 5 | 5'-CCC TAA CCC TAA CCC TAA PPPPP SEQ ID NO:12 |
| HT6 | 6 | 5'-CCC TAA CCC TAA CCC TAA PPPPPP |
| HT3A3 | 6 | 5'-CCC TAA CCC TAA CCC TAA PPPAPPP |
| HT7 | 7 | 5'-CCC TAA CCC TAA CCC TAA PPPPPPP |
| HT3B | 3 | 5'-PPP AAC CCT AAC CCT AAC CCT SEQ ID NO:13 |
| HT4B | 4 | 5'-PPPP AAC CCT AAC CCT AAC CCT SEQ ID NO:14 |
| HT5B | 5 | 5'-PPPPP AAC CCT AAC CCT AAC CCT SEQ ID NO:15 |
| HT6B | 6 | 5'-PPPPPP AAC CCT AAC CCT AAC CCT |
| HT3C | 3 | 5'-PPP CCC TAA CCC TAA CCC TAA |
| tel3 | 0 | 5'-TTA GGG TTA GGG TTA GGG SEQ ID NO:16 |
| tel3B | 0 | 5'-AGG GTT AGG GTT AGG GTT SEQ ID NO:17 |

Figure 19A:
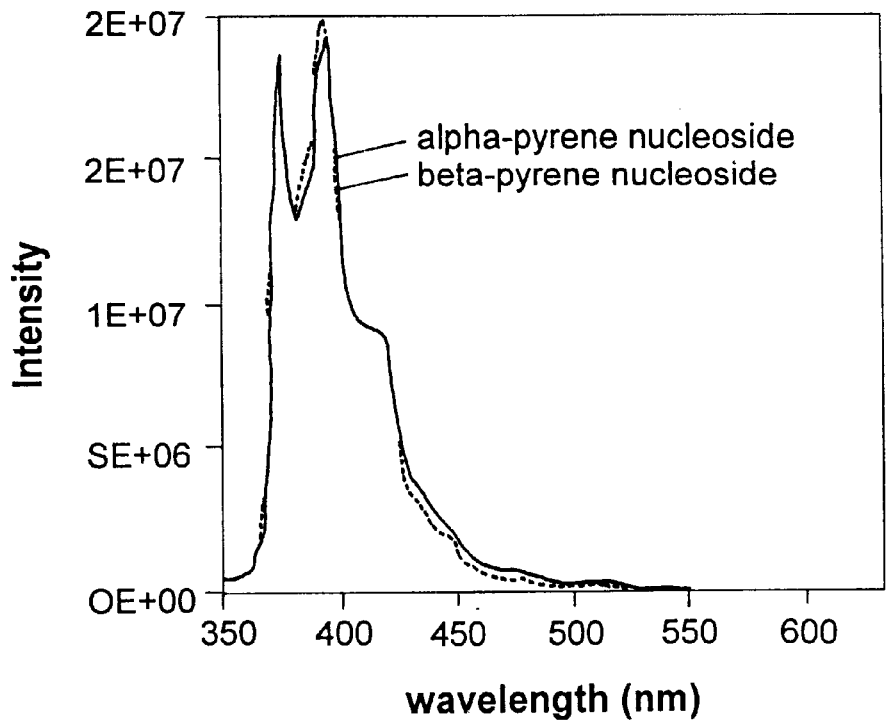
FIG. 19A is an emission spectra for single pyrene alpha- and beta-nucleosides at 0.1 μM in methanol (excitation 348 nm).
Figure 19B:
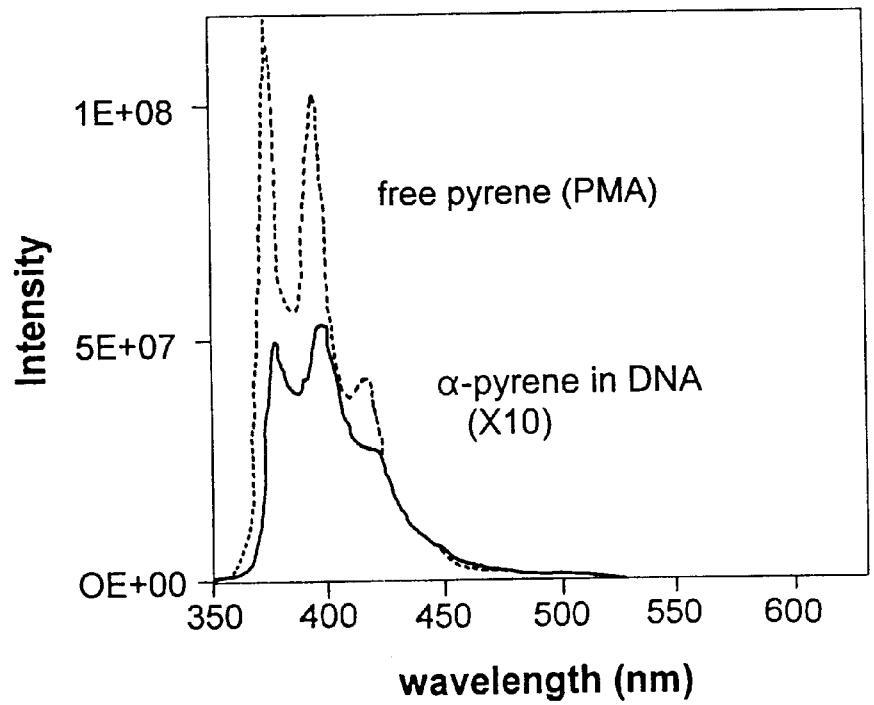
FIG. 19B is an emission spectra for alpha-pyrene in DNA (aqueous buffer) compared to pyrenemethylamine.HCl at the same concentration (intensities for pyrene-DNA are multiplied by 10).

DNA oligonucleotides were synthesized on an Applied Biosystems 392 synthesizer using standard β-cyanoethylphosphoramidite chemistry but with extended (12.5 minute) coupling cycles for the pyrene residues, as described.[31,32] Stepwise coupling yields for the pyrene residues were typically greater than 95% as determined by trityl cation monoriting. A pyrene phosphoramidite concentration of 0.05M in acetonitrile was used, and shown not to compromise coupling efficiency. DNA oligomers were purified by preparative 20% denaturing polyacrylamide gel Fluorescence of single pyrene nucleosides in solution and in DNA. Fluorescence measurements were performed as described in Example 5. The 18mer DNA sequences chosen for labeling are complementary to the human telomere repeat sequence.[34] The fluorescence emission spectra for the free nucleosides of alpha- and beta-pyrene were first measured. They were sparingly soluble in water and so were measured in methanol (FIG. 19A). They were found to have identical emission profiles and intensities, and show three bands between 350–425 nm ($\lambda_{max}$=396 nm), typical of pyrene monomer emission. A single α-pyrene label was incorporated at the oligonucleotide 3' end (sequence HT1, with pyrene adjacent to adenine) and the fluorescence spectrum measured in aqueous buffer (FIG. 19B). The emission profile was found to be essentially identical to that of the free nucleoside and to that of pyrenemethylamine hydrochloride (PMAH). Using PMAH as a model for free pyrene in aqueous buffer, comparison of emission intensities at equal pyrene concentrations shows a ~17-fold decrease in intensity upon incorporation of α-pyrene into this DNA sequence, consistent with previous observations.[30b]

Figure 20:
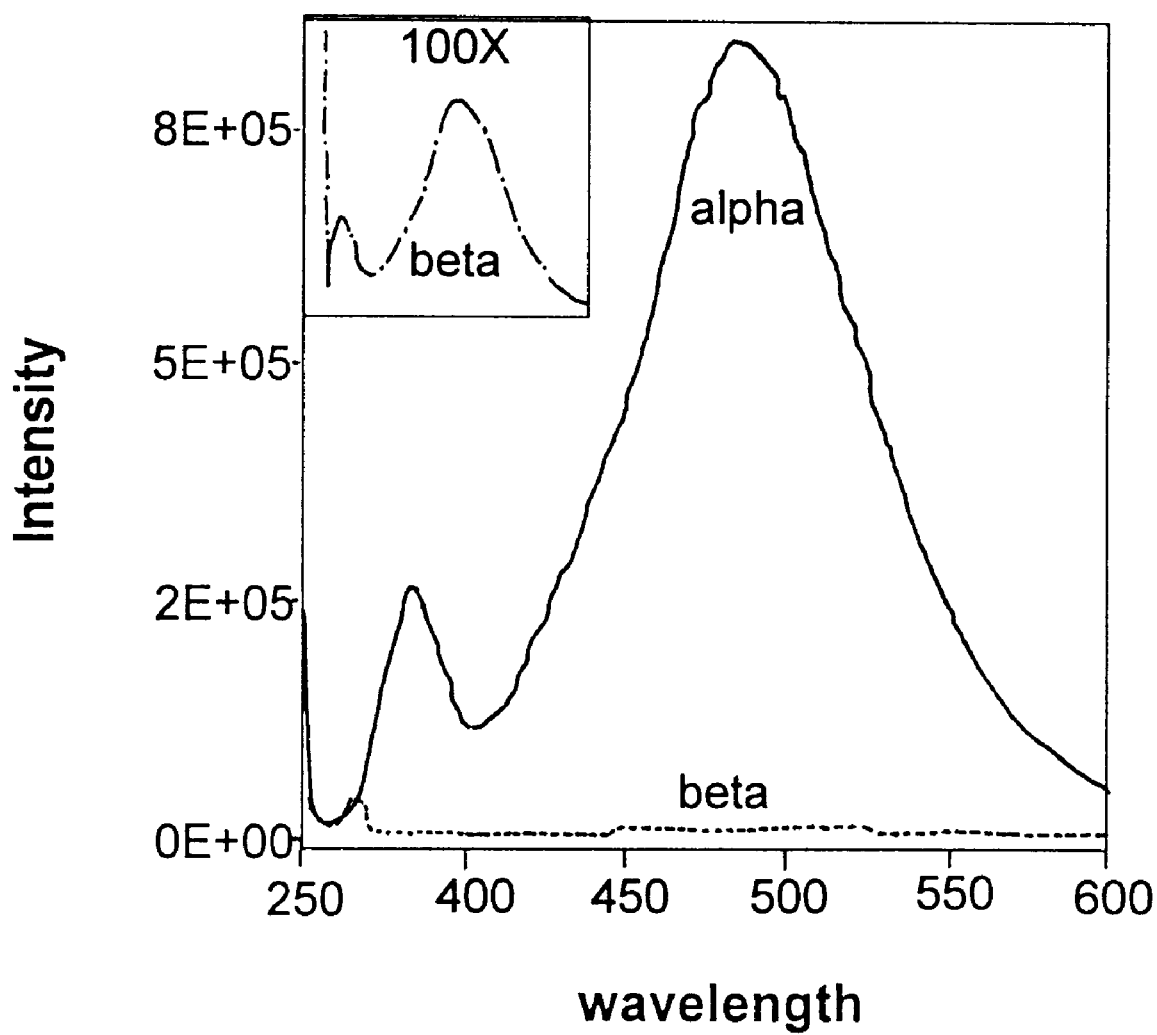
FIG. 20 shows the effect of alpha- vs. beta-isomeric structure on fluorescence intensity, as shown by fluorescence emission spectra of HT3 (three alpha pyrene nucleosides) as compared to the same sequence with three beta pyrene nucleosides. Excitation was at 341 nm; band at 390 nm is due to Raman scattering and is present with buffer alone.

Multiple pyrene substitution in oligodeoxynucleotides. Preliminary studies comparing alpha- and beta-pyrene labels in the same sequence of DNA showed consistently that the beta-pyrene labels gave much lower fluorescence intensity, despite the fact that as free nucleosides the two behave identically. One example of this effect is shown in FIG. 20, which compares emission spectra for a sequence containing three consecutive alpha- or beta- labels. Although emission profiles are virtually the same, with the beta configuration the intensity is about 100 times lower.

Figure 21A:
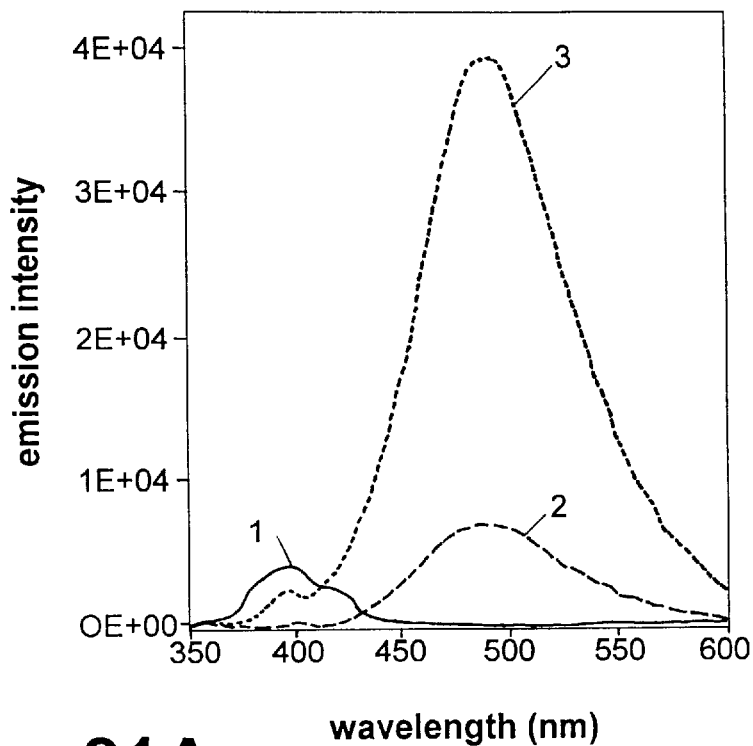
FIG. 21A shows emission spectra for sequences HT1–HT3, containing 1–3 pyrenes.

A series of oligonucleotides carrying 1–7 α-pyrenes at the 3' end (sequences HT1-HT7) and 3–6 α-pyrenes at the 5' end (HT3B-HT6B) was synthesized. The emission spectra are shown for the 3' series in FIG. 21, and the absorption spectra in FIG. 22. The numerical data are given in Table 3. For all cases, when two or more adjacent pyrenes are present in DNA, excimer formation was observed as a broad structureless band between 400 and 600 nm (peak maximum ~489 nm) (FIG. 21A). With two pyrenes there is a very small amount of residual monomer emission seen (excimer/monomer is >20:1), and beyond three labels (FIG. 21B) no monomer emission is detectable. Similar results are observed at the 5' end of the sequence (see Table 3), although for those cases a low-intensity shorter wavelength shoulder was visible on the excimer band at ca. 425–450 nm.

Figure 21B:
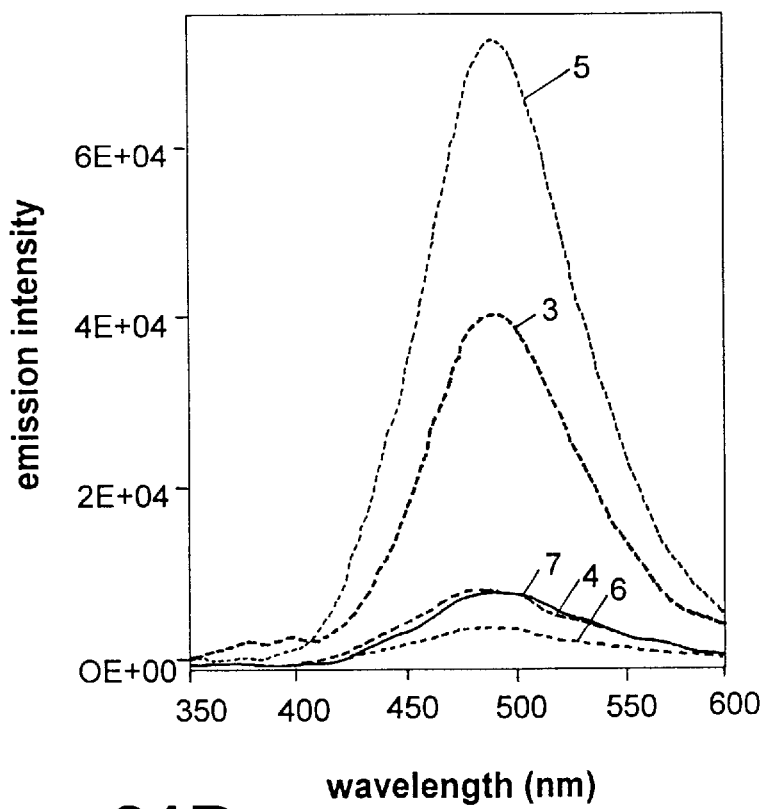
FIG. 21B shows emission spectra for HT3–HT7, with 3–7 adjacent pyrenes. Excitation was at 341 nm with equal DNA strand concentration of 0.1 μM; see Table 1 for numerical data.
Figure 22:
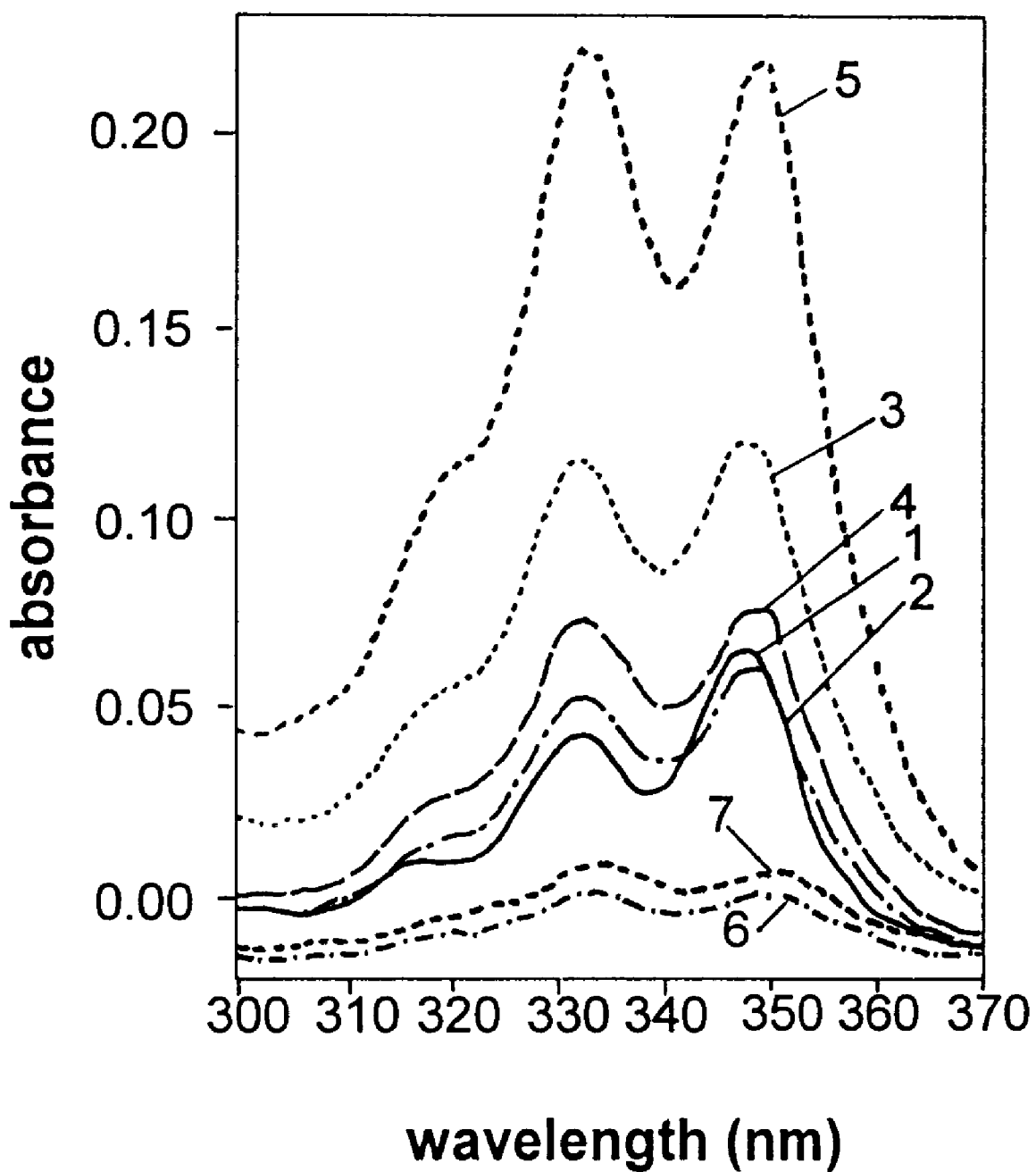
FIG. 22 shows adsorption spectra for oligonucleotides containing 1–7 adjacent alpha-pyrene labels (sequence HT1–HT7). Measurements are carried out at equal pyrene concentrations (2 μM in pyrene), rather than equal DNA strand concentrations, to show differences in molar extinction due to grouping effects.

The emission intensity trends were observed to be generally similar at both ends of the DNA if the neighboring base is the same (Table 3). For both series the emission intensity increases generally and reaches a peak at five labels, after which further increasing the number of consecutive labels actually results in a decrease in overall emission intensity (FIG. 21, Table 3). Interestingly, the relative emission intensities correlate well with the rank order of molar absorptivities of each labeled oligomer (FIG. 22, Table 3). For example, the sequence with six α-pyrenes actually has both a lower molar absorptivity (by nearly 300-fold at 348 nm) and a lower fluorescence emission intensity (by 21-fold) than that with five, despite the greater number of pyrenes. For the HT2-7 series excitation spectra was also measured by monitoring at 489 nm, and the resulting spectra were virtually identical to the absorption spectra in FIG. 22.

Figure 23:
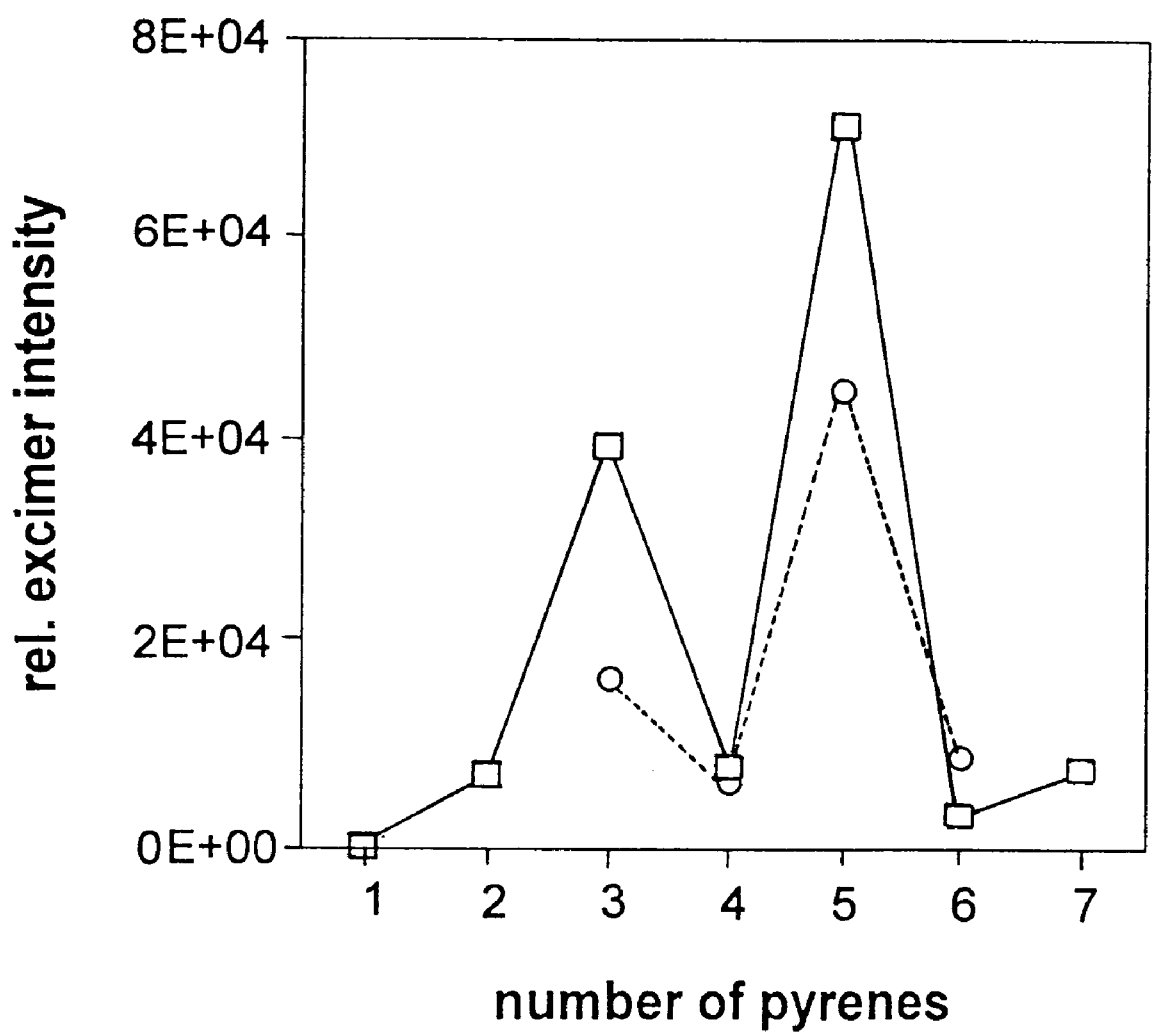
FIG. 23 shows the even/odd effect on excimer fluorescence intensity. Plot of number of pyrenes vs. relative integrated excimer emission intensity for 3' end series (□) (sequences HT1–7) and for 5' end series (○) (HT3B–6B).

Even/odd effects in emission intensity. Viewing the series as a whole, an interesting trend is seen with the number of adjacent pyrenes and the intensity of excimer formation (FIG. 23). Not unexpectedly, three pyrenes are more brightly fluorescent than two, but surprisingly, four are not as bright as three. Five pyrenes yields very bright emission, while six is much less intense. Seven labels again shows a small increase in intensity. In general, an odd number of pyrenes seems to favor more intense excimer emission, whereas an even number produces weak emission (FIG. 21B, Table 3). The same trend was observed for both the 3' and 5' labeled oligomer series. This is further substantiated by examining the fluorescence intensity for two different oligomers each possessing six pyrenes. The one with six adjacent pyrenes is much less fluorescent than the one where they are divided into two groups of three with an adenine in between (HT6 vs. HT3A3, Table 3). Examination of the absorption spectra (FIG. 22) shows that the rank order of absorptivity correlates well with emission intensity. Thus, the even/odd effects are seen at the ground state prior to excitation.

Evidence for preassociation. To determine whether the excimer fluorescence arises from excited-state or ground-state association of pyrenes in these multi-labeled DNAs, several pieces of data was examined. First, measurement of absorption spectra for free pyrene (PMAH) and alpha-pyrenes in DNA (sequences HT1-7) shows that all the DNA-associated pyrenes exhibit a redshift of ~6–9 nm. Free PMAH in buffer has peak maxima at 325 and 342 nm, whereas those of HT1-7 lie at ~331 and 348 nm (Table 3), consistent with stacked species. Second, observation of absorption band broadening by measurement of peak vs. valley ratios, which has also been used to measure degree of preassociation,[14,15] was carried out. For a single pyrene alone a peak:valley ratio of 2.7 was measured, whereas for the multilabeled DNAs the values decreased: for 2,3,4,5 and 7 labels the values were 1.74, 1.29, 1.54, 1.38, and 4.0 respectively. Thus, the most intense excimers also may be the most highly preassociated cases by this measure.

Effect of neighboring bases. The effect of a cytosine versus an adenosine neighboring base was tested (sequences HT3B vs. HT3C). The oligomer where the neighboring base is adenosine was twice as intensely fluorescent as the corresponding oligomer with pyrenes adjacent to a cytosine (Table 3). It is not yet known whether this apparent quenching is due to a lowering of absorptivity or of quantum yield. In any case, this apparent quenching appears to hold for pyrene excimers as well as monomer emission.

Hybridization effects. To test whether addition of pyrene labels affects the ability of the DNA to bind its complement, thermal denaturation studies of the 3' and 5' series with the complementary 18mer DNA. The results are shown in Table 4. In general, there is little effect on melting temperatures ($T_m$) as compared to the unlabeled sequence (HTO). Addition of pyrenes to the 3' end is somewhat stabilizing until six or seven labels are present, in which case the labels are slightly destabilizing. Addition of pyrene labels to the 5' end is somewhat more stabilizing than the 3' end, presumably because stacking is more favorable at the 5' end of a DNA helix.[35]

Also examined was the effect of hybridization on fluorescence emission intensity (Table 3). In general there is very little effect, with intensity decreasing or increasing to a small degree on binding. One notable exception is the sequence containing a single pyrene at the 3' end (HT1): On binding the tel3 sequence there is a 20-fold drop in fluorescence intensity. Examination of the complementary strand shows that thymine is present at the end where the label is situated on the probe strand; it seems likely that the binding of the complement causes pyrene to stack not only on adenine but also on its partner (thymine), which causes strong quenching of the pyrene.

Results with the alpha- and beta-isomeric pyrene free nucleosides show clearly that, as expected, they possess essentially the same fluorescence properties in methanol. However, in a number of different sequences the beta-pyrene exhibits much weaker fluorescence emission than does the alpha-anomeric species. This is true both with single substitution in DNA and with multiply-substituted excimer-emitting species (FIG. 20). Separate studies have established that the beta-substituted pyrene anomer stacks quick strongly with natural beta-oriented DNA strands, while the alpha-substituted case stacks less strongly.[35] Similarly, placement of a single pyrene nucleoside into DNA results in ca. 17-fold lower emission intensity than that for free pyrenemethylamine.HCl in aqueous buffer, also consistent with quenching by covalent attachment to the DNA. Also, an adjacent adenine is less strongly quenching that cytosine or thymine, which has also been observed with other pyrene labels.[30b]

In two different sequence contexts a surprising effect on excimer emission was observed as the number of contiguous pyrenes increases. First, excimer emission intensity tends generally to increase up to five labels and then decreases beyond this number. Second, and even more striking, is that there appears to be an even/odd effect on fluorescence properties. Three and five labels gives strong excimer intensity, while, surprisingly, four or six labels gives much lower intensity (by ca. 6–20 fold). Although intensity drops off strongly beyond five labels, the even/odd effect extends at least through seven labels, which also is somewhat more intense than six labels.

Studies of the absorption and excitation spectra for the series containing one through seven contiguous alpha pyrene yields some information on the origins of this effect. It is clear that the extinction coefficient of a given pyrene-tagged molecule (viewing a group of pyrenes as a single molecular entity) varies with the emission intensity. Thus, the even/odd effects are seen on ground state, and it may not be necessary to invoke special excited-state interactions to explain the effect. Rather, it appears that the ground-state structure or electronic interaction of the multiple pyrene groups may be the primary source of the effects.

TABLE 1

H1'–H2' COUPLING CONSTANTS AND PROTON NOE DATA FOR BETA ISOMERS OF ARYL NUCLEOSIDES 1–6 IN CD$_3$OD.

| Aryl substituent | J values,[a] H1'–H2' | NOE Observed: | Irradiation at: H1' | H2'α | H2'β |
|---|---|---|---|---|---|
| 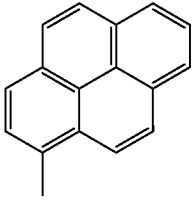 | 3.6, 10.8 Hz | H1' H2'α H3' H4' | —% 7 0 6 | 8% — 0 — | 0% — 0 — |
| 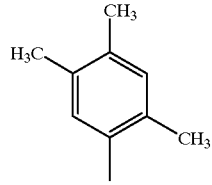 | 3.5, 10.5 Hz | H1' H2'α H3' H4' | —% 8 0 6 | 8% — 0 — | 0% — 12 — |

TABLE 1-continued

H1'–H2' COUPLING CONSTANTS AND PROTON NOE DATA FOR BETA ISOMERS OF ARYL NUCLEOSIDES 1–6 IN CD$_3$OD.

| Aryl substituent | J values,[a] H1'–H2' | NOE Observed: | Irradiation at: H1' | H2'α | H2'β |
|---|---|---|---|---|---|
| 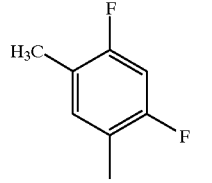 | 3.2, 10.7 Hz | H1' H2'α H3' H4' | —% 7 0 6 | 8% — 0 — | 0% — 5 — |
| 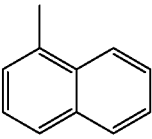 | 2.6, 10.9 Hz | H1' H2'α H3' H4' | —% 7 0 6 | 10% — 0 — | 0% — 12 — |
| 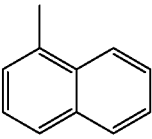 | 2.5, 10.8 Hz | H1' H2'α H3' H4' | —% 9 0 6 | 8% — 0 — | — — — — |
| 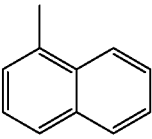 | 2.3, 10.2 Hz | H1' H2'α H3' H4' | —% 9 0 6 | — — — — | — — — — |

[a]Coupling constants are for bis-toluoyl ester derivatives of 1–6 in CDCl$_3$'

TABLE 2

PROTON H1'–H2' COUPLING CONSTANTS AND NOE DATA FOR ALPHA ISOMERS OF ARYL NUCLEOSIDES (COMPOUNDS 3A, 5A, AND 6A) IN CD$_3$OD.

| Aryl substituent | J values,[a] H1'–H2' | NOE Observed: | NOE data: Irradiation at: H1' | H2'α | H2'β | H3' |
|---|---|---|---|---|---|---|
| 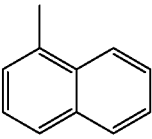 (alpha isomer) | 8.0, 6.0 Hz | H1' H2'α H2'β H3' | —% 0 8 3 | 0% — — 0 | 8% — — 7 | 0% 0 6 — |

TABLE 2-continued

PROTON H1'–H2' COUPLING CONSTANTS AND NOE DATA FOR ALPHA ISOMERS OF ARYL NUCLEOSIDES (COMPOUNDS 3A, 5A, AND 6A) IN CD$_3$OD.

| Aryl substituent | J values,[a] H1'–H2' | NOE Observed: | NOE data: Irradiation at: H1' | H2'α | H2'β | H3' |
|---|---|---|---|---|---|---|
| [4-F, 2-F tolyl structure] (alpha isomer) | 7.6, 7.6 Hz | H1'<br>H2'α<br>H2'β<br>H3' | —%<br>0<br>8<br>— | 0%<br>—<br>—<br>0 | 9%<br>—<br>—<br>8 | 0%<br>0<br>8<br>— |
| [dimethyl tolyl structure] (alpha isomer) | 6.6, 6.6 Hz | H1'<br>H2'α<br>H2'β<br>H3' | —%<br>0<br>6<br>2 | 2%<br>—<br>—<br>4 | 12%<br>—<br>—<br>12 | —%<br>—<br>—<br>— |

[a]Coupling constants are for toluoyl ester derivatives in CDCl$_3$.

TABLE 3

Fluorescence data for pyrene-labeled oligodeoxynucleotides in aqueous buffer[a]

| sequence | # pyrenes | location | absorption λ$_{max}$ | ε$_{348}$ | emission λ$_{max}$ | intensity (rel)[b] |
|---|---|---|---|---|---|---|
| unhybridized | | | | | | |
| HT1 | 1 | 3' end | 331,348 | 3.2E4 | 396 | 1 |
| HT2 | 2 | " | 331,348 | 5.9E4 | 489 | 3.2 |
| HT3 | 3 | " | 333,348 | 1.8E5 | 489 | 18 |
| HT4 | 4 | " | 333,348 | 1.5E5 | 489 | 3.6 |
| HT5 | 5 | " | 335,351 | 5.3E5 | 489 | 31 |
| HT6 | 6 | " | 333,349 | 1.8E3 | 487 | 1.5 |
| HT3A3 | 6 | " | — | — | 484 | 27 |
| HT7 | 7 | " | 333,350 | 1.6E4 | 483 | 3.4 |
| HT3B | 3 | 5' end | — | — | 488 | 7.5 |
| HT4B | 4 | " | — | — | 489 | 2.6 |
| HT5B | 5 | " | — | — | 481 | 17 |
| HT6B | 6 | " | — | — | 475 | 3.0 |
| HT3C | 3 | " | — | — | 486 | 3.9 |
| hybridized | | | | | | |
| HT1•tel3 | 1 | 3' end | — | — | 384 | 0.05 |
| HT2•tel3 | 2 | " | — | — | 490 | 5.3 |
| HT3•tel3 | 3 | " | — | — | 487 | 14 |
| HT4•tel3 | 4 | " | — | — | 490 | 4.4 |
| HT5•tel3 | 5 | " | — | — | 489 | 24 |
| HT6•tel3 | 6 | " | — | — | 489 | 1.2 |
| HT7•tel3 | 7 | " | — | — | 482 | 1.7 |

[a]Conditions: 10 mM PIPES (pH 7.0), 10 mM MgCl$_2$, 100 mM NaCl, 0.1 μM in each strand.
[b]Integrated emission peak area (425–600 nm), relative to that of HT1 (350–425 nm).

TABLE 4

Thermal denaturation data (T$_m$, ° C.) for pyrene-labeled oligonucleotides hybridized to a short complementary sequence (tel3 or tel3B))[a]

| sequence | # pyrenes | location | T$_m$ (° C.) |
|---|---|---|---|
| HT0 | 0 | — | 63.4 |
| HT1 | 1 | 3' end | 65.4 |
| HT2 | 2 | " | 65.9 |
| HT3 | 3 | " | 66.1 |
| HT4 | 4 | " | 66.4 |
| HT5 | 5 | " | 65.8 |
| HT6 | 6 | " | 61.1 |
| HT7 | 7 | " | 60.0 |
| HT3B | 3 | 5' end | 68.3 |
| HT4B | 4 | " | 66.5 |

[a]Conditions: 10 mM PIPES (pH 7.0), 10 mM MgCl2, 100 mM NaCl, 2 μM in each strand.

REFERENCES

1. Santa Lucia, J.; Kierzek, R.; Turner, D. H. *Science* 1992, 256, 217.
2. (a) Smith, S. A.; Rajur, S. B.; McLaughlin, L. W., *Vature Struct. Biol.* 1994, 1, 198. (b) Lesser, D. R.; Kurpiewski, M. R.; Jen-Jacobson, L. *Science* 1990, 250, 776.
3. (a) Kornberg, A.; Baker, T. A. "DNA Replication", 2nd ed., W. H. Freeman: New York, 1992. (b) Echols, H.; Goodman, M. F. *Ann. Rev. Bioch.* 1991, 60, 477. (c) Strazewski, P.; Tamm C. *Angew. Chem. Int. Ed. Engl.* 1990, 29, 36.
4. Kempe, T.; Sundquist, W. I.; Chow, F.; Ho, S. L. *Nucleic Acids Res.* 1985,13,45.

5. Zischler, H.; Nanda, I.; Schafer, R; Scbmid, M.; Epplen, J. T. *Hum. Genet.* 1989,82, 227.
6. (a) Weygand-Durasevic, I.; Susic, S. *Biochim. Biophys. Acta* 1990, 1048, 38. (b) Hustedt, E. J.; Spaltenstein, A.; Kirchner, J. J.; Hopkins, P. B.; Robinson. B. H. *Biochemistry* 1993, 32, 1774.
7. Dreyer, G. B.; Dervan, P. B. *Proc. Natl. Acad. Sci. USA* 1985, 82, 968.
8. Beaucage, S. L.; Iyer, R. P. *Tetrahedron* 1993, 49, 1925.
9. (a) Ansorge, W.; Sproat, B. S.; Stegemann, J.; Schwager, C. J.; *Biochem. Biophys. Methods* 1986, 13, 315. (b) Karger, A. E.; Harris, J. M.; Gesteland, R. F. *Nucleic Acids Res.* 1991, 19, 4955.
10. (a) Ward, D. C.; Reich, E.; Stryer, L. *J. Biol. Chem.* 1969, 244, 1228. (b) Bloom, L. B.; Otto, M. R.; Beechem, J. M.; Goodman, M. F. *Biochemistry* 1993, 32, 11247.
11. (a) Secrist, J. A.; Barrio, J. R.; Leonard, N. J. *Science* 1972, 175,646. (b) Toulme, J. J.; Helene, C. *Biochim Biophys. Acta* 1980, 606, 95.
12. Schweitzer, B. A.; Kool, E. T. *J. Org. Chem.* 1994, 59, 7238.
13. (a) Chaudhuri, N. C.; Kool, E. T. *Tetrahedron Lett.* 1995, 1795. (b) Chandhuri, N. C.; Kool, E. T. ibid, 4910.
14. Schweitzer, B. A.; Kool, E. T. *J. Am. Chem. Soc.* 1995, 117, 1863.
15. Hunter, C. A. *Angew. Chem., Int. Ed. Engl.* 1993.32, 1584.
16. (a) Matsumoto, T.; Katsuki, M.; Suzuki, K. *Tetrahedron Lett.* 1988, 29.6935. (b) Ohrui, H.; Kuzubara, H.; Emoto, S. *Agr. Biol Chem. (Tokyo)* 1972,36, 1651–1653.
17. Klein, R. S.; Kotick, M. P.; Watanabe, K. A.; Fox J. J. *J. Org. Chem.* 1971,36.4113.
18. Millican, T. A.; Mock, G. A.; Chauncey, M. A.; Patel T. P.; Eaton, M. A. W., Gunning, J.; Cutbush, S. D.; Neidle, S.; Mann, *J. Nucleic Acids Res.* 1984, 12, 7435.
19. Hoffer, M. *Chem. Ber.* 1960, 93, 2777.
20. Davies, D. B. *Prog. NMR Spectrosc.* 1978, 12,135.
21. (a) Schulman, S. G. *Molecular Luminescence Spectroscopy*, Wiley: New York, 1990, 1–27. (b) Slavik J. *Fluorescent Probes in Cellular and Molecular Biology*, CRC Press: Boca Raton, 1990, 1–36.
24. Cleve, G.; Hoyer, G.; Schulz, G.; Vorbruggen, H. *Chem. Ber.* 1973, 106, 3062.
25. Robins, M. J.; Robins, R. K. *J. Am. Chem. Soc.* 1965, 87, 4934.
26. (a) Srivastava, P. C.; Robins, P. K.; Takusagawa, F.; Berman, H. M. *J. Het. Chem.* 1981, 18, 1659. (b) Hacksell, U.; Cheng, J. C-Y.; Daves, G. D., Jr. *Nucleosides & Nucleotides* 1986, 5, 287.
28. Sugimoto, N.; Kierzek, R.; Tumer, D. H. *Biochemistry* 1987, 26, 4554.
29. Senior, M.; Jones, R. A.; Breslauer, K. J. *Biochemistry* 1988, 27, 3879.
30. (a) Telser, J.; Cruickshank, K. A.; Morrison, L. E.; Netzel, T. L.; Chan, C. *J. Am. Chem. Soc.* 1989, 111, 7226. (b) Telser J.; Cruickshank, K. A.; Morrison, LF.; Netzel, T. L. *J. Am. Chem. Soc.* 1989, 111, 6966. (c) Lee, H.; Hinz, M.; Stezowski, J. J.; Harvey, R. G. *Tetrahedron Lett.* 1990, 31, 6773. (d) Yamana, K.; Gokota, T.; Ozaki, H.; Nakano, H.; Sangen, O.; Shimidzu, T. *Nucleosides Nuclotides* 1992, 11, 383. (e) Prokhorenko, I. A.; Petrov, A. A.; Gontarev, S. V.; Berlin, Y. A. *BioMed. Chem. Lett.* 1995, 5, 2081. (f) Li, Y.; Bevilacqua P. C.; Mathews, D.; Turner, D. H. *Biochemistry* 1995, 34, 14394. (g) Tong, G.; Lawlor, J. M.; Tregear, G. W.; Haralambidis, J. *J Am. Chem. Soc.* 1995, 117, 12151.
31. Moran, S.; Ren, R. X.-F.; Sheils, C. J.; Kool, E. T. *Nucleic Acids Res.* 1996, 24, 2044.
32. Ren, R. X.-F.; Chaudhuri, N. C.; Paris, P. L.; Rummey IV, S.; Kool, E. T. *J. Am. Chem. Soc.* 1996, 188, 7671.
33. Borer, P. N. in *Handbook of Biochemistry and Molecular Biology*, G. D. Fismann, ed., CRC Press: Cleveland, 1975, p. 589.
34. Moyzis, R. K.; Buckingham, J. M.; Cram, L. S.; Dani, M.; Deaven, L. L.; Jones, M. D.; Meyne, J.; Ratliff, R. L.; Wu, J.-R. *Proc. Natl. Acad. Sci. USA* 1988, 85, 6622.
35. Guckian, G.; Schweitzer, B. A.; Ren, R. X.-F.; Sheils, C. J.; Paris, P. L.; Tahmassebi, D. C.; Kool, E. T. *J. Am. Chem. Soc.* 1996, 118, 8182.

What is claimed is:

1. A nucleoside derivative comprising a pyrene, anthracene, phenanthrene, stilbene, tetracene or pentacene joined to the C-1 atom of a sugar moiety through a carbon-carbon bond in either an α or β configuration wherein said sugar moiety is ribose or deoxyribose.

2. α-9-phenanthrenyl deoxynucleoside.

3. α-1-pyrenyl deoxynucleoside.

4. β-9-phenanthrenyl deoxynucleoside.

5. β-1-pyrenyl deoxynucleoside.

6. A phosphoramidite derivative of the nucleoside derivative of claim 1 wherein the phosphoramidite moiety is jointed to the sugar moiety at the 3' position.

7. The nucleoside derivative of claim 1 wherein the pyrene, anthracene, phenanthrene, stilbene, tetracene or pentacene is derivatized at an available carbon position with a substituent selected from the group consisting of methoxy, ethoxy, dimethylamino, diethylamino, nitro, methyl, cyano, carboxy, chloro, bromo, iodo and amino.

8. A nucleic acid comprising at least one nucleoside derivative according to any one of claims 1–6.

9. A method of synthesizing the nucleoside analog of claim 1 which comprises:
  a. coupling an organocadmium or organozinc derivative of pyrene, anthracene, phenanthrene, stilbene, tetracene or pentacene to the C1 position of Hoffer's α-chlorosugar; and
  b. removing the protecting groups with a methanolic base.

10. A method of synthesizing a phosphoramidite derivative of the nucleoside of claim 1 which comprises:
  a. coupling an organocadmium or organozinc derivative of pyrene, anthracene, phenanthrene, stilbene, tetracene or pentacene to the C1 position of Hoffer's α-chlorosugar;
  b. removing the protecting groups with a methanolic base;
  c. tritilating the 5'-OH with dimeoxytritylchloride in the presence of a base; and
  d. phosphytilating the 3'-OH with a phosphytilating agent.

11. A method of preparing a fluorescently labeled nucleic acid which comprises incorporating a nucleoside analog of any one of claims 1–6 into an RNA or DNA molecule under conditions sufficient to incorporate said nucleoside.

12. A method of detecting a target nucleic acid in a sample to be tested which comprises contacting the target nucleic acid with a nucleic acid probe comprising a nucleoside derivative of any one of claims 1–6 for a time and under conditions sufficient to permit hybridization between said target and said probe; and detecting said hybridization.

13. α-1-anthracenyl deoxynucleoside having the following structural formula:

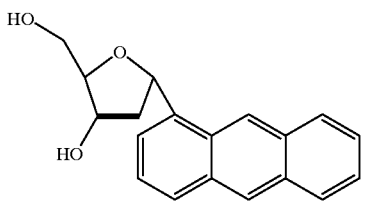

14. β-1-anthracenyl deoxynucleoside having the following structural formula:

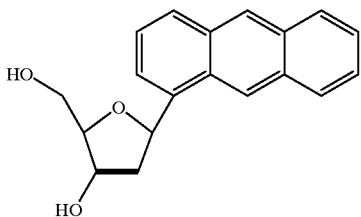

15. The phosphoramidite derivative of claim 6 wherein the phosphoramidite derivative is N,N-diisopropyl-O-cyanoethyl phosphoramidite derivatized at the 3' alcohol of the pyrene, anthracene, phenanthrene, stilbene, tetracene or pentacene derivatized nucleoside.

16. The nucleic acid of claim 8 wherein the nucleoside derivative is incorporated adjacent to an adenine base.

17. A nucleic acid comprising at least three to five nucleoside derivatives selected from the group consisting of a pyrene, anthracene, phenanthrene, stilbene, tetracene and pentacene joined to the C-1 atom of a sugar moiety through a carbon-carbon bond in either an α or β configuration wherein said sugar moiety is ribose or deoxyribose and wherein said nucleoside derivative is incorporated adjacent to an adenine base.

18. The nucleic acid of claim 8 comprising at an odd number of nucleoside derivatives.

19. The nucleic acid according to claim 8 comprising at least three, five, or seven nucleoside derivatives.

20. The method of claim 12 wherein the method of detecting a target nucleic acid is by fluorescence in situ hybridization.

* * * * *